US012646594B2

(12) United States Patent
Minas et al.

(10) Patent No.: US 12,646,594 B2
(45) Date of Patent: Jun. 2, 2026

(54) METHODS AND APPARATUS FOR MANAGING A HYDROGEN STORAGE AND DISTRIBUTION SYSTEM

(71) Applicant: General Electric Company, Schenectady, NY (US)

(72) Inventors: Constantinos Minas, Slingerlands, NY (US); Lisa Tang, Niskayuna, NY (US)

(73) Assignee: General Electric Company, Evendale, OH (US)

(*) Notice: Subject to any disclaimer, the term of this patent is extended or adjusted under 35 U.S.C. 154(b) by 222 days.

(21) Appl. No.: 18/072,340

(22) Filed: Nov. 30, 2022

(65) Prior Publication Data

US 2024/0177810 A1    May 30, 2024

(51) Int. Cl.
*G16C 20/70* (2019.01)
*F17C 13/00* (2006.01)
(Continued)

(52) U.S. Cl.
CPC .............. *G16C 20/70* (2019.02); *F17C 13/00* (2013.01); *F17C 13/02* (2013.01); *F17C 13/023* (2013.01);
(Continued)

(58) Field of Classification Search
CPC ........ G16C 20/70; G01M 3/26; G01M 3/226; G01M 3/3254; G01M 3/186; F17C 13/12;
(Continued)

(56) References Cited

U.S. PATENT DOCUMENTS

| | | | | | |
|---|---|---|---|---|---|
| 5,517,537 A | * | 5/1996 | Greene | .................. | G01M 3/24 |
| | | | | | 376/405 |
| 6,519,041 B1 | * | 2/2003 | Berthold | ................. | G01M 3/38 |
| | | | | | 356/477 |

(Continued)

FOREIGN PATENT DOCUMENTS

| | | | | |
|---|---|---|---|---|
| CA | 2714125 | | 2/2012 | |
| CN | 209085657 U | * | 7/2019 | ......... B62D 15/0215 |

(Continued)

OTHER PUBLICATIONS

Translation of CN113720537.*

(Continued)

*Primary Examiner* — Helen C Kwok
(74) *Attorney, Agent, or Firm* — Hanley, Flight & Zimmerman, LLC

(57) ABSTRACT

Methods, apparatus, systems, and articles of manufacture are disclosed for managing a hydrogen storage and distribution system. An example apparatus disclosed herein includes an apparatus comprising memory and one or more processors to execute instructions to detect, via hydrogen concentration data, an elevated hydrogen concentration at a hydrogen storage system, determine a mass flow rate of a leak associated with the elevated hydrogen concentration based on the hydrogen concentration data and a location of a sensor associated with the hydrogen concentration data, and mitigate the leak by sending a signal to one or more controllable features of the hydrogen storage system based on the determined mass flow rate.

17 Claims, 22 Drawing Sheets

(51) Int. Cl.

| | |
|---|---|
| *F17C 13/02* | (2006.01) |
| *F17C 13/12* | (2006.01) |
| *G01M 3/18* | (2006.01) |
| *G01M 3/22* | (2006.01) |
| *G01M 3/26* | (2006.01) |
| *G01M 3/32* | (2006.01) |

(52) U.S. Cl.
CPC ............. *F17C 13/12* (2013.01); *G01M 3/186* (2013.01); *G01M 3/226* (2013.01); *G01M 3/26* (2013.01); *G01M 3/3254* (2013.01); *F17C 2221/012* (2013.01); *F17C 2250/032* (2013.01); *F17C 2250/0443* (2013.01); *F17C 2250/0452* (2013.01); *F17C 2250/0694* (2013.01); *F17C 2260/044* (2013.01); *F17C 2265/06* (2013.01)

(58) Field of Classification Search
CPC ........ F17C 13/02; F17C 13/00; F17C 13/023; F17C 2250/033; F17C 2250/0443; F17C 2250/0452; F17C 2250/0694; F17C 2250/0404; F17C 2250/07
See application file for complete search history.

(56) References Cited

U.S. PATENT DOCUMENTS

| | | | |
|---|---|---|---|
| 7,345,590 B2 | 3/2008 | Nakano et al. | |
| 8,950,195 B2 | 2/2015 | Watts | |
| 9,932,124 B2 | 4/2018 | Kamath et al. | |
| 10,753,677 B2 | 8/2020 | Suraganda Narayana et al. | |
| 10,948,471 B1* | 3/2021 | MacMullin | G01N 33/0047 |
| 2002/0125131 A1* | 9/2002 | Babes-Dornea | G01N 33/005 |
| | | | 204/415 |
| 2003/0063702 A1* | 4/2003 | Kruger | G21C 19/307 |
| | | | 376/260 |
| 2003/0164202 A1* | 9/2003 | Graham | B60S 5/02 |
| | | | 141/98 |
| 2007/0277593 A1* | 12/2007 | Salem | G01M 3/228 |
| | | | 73/40.7 |
| 2009/0308489 A1* | 12/2009 | Hirakata | F17C 13/025 |
| | | | 141/37 |
| 2013/0213479 A1* | 8/2013 | Oates | F17D 1/02 |
| | | | 137/605 |
| 2014/0026597 A1 | 1/2014 | Epstein et al. | |
| 2014/0123624 A1* | 5/2014 | Minto | F23N 1/00 |
| | | | 60/39.281 |
| 2014/0174105 A1 | 6/2014 | Gerstler et al. | |
| 2016/0334353 A1* | 11/2016 | Potyrailo | G02B 6/00 |
| 2017/0097274 A1* | 4/2017 | Thorpe | G01C 15/00 |
| 2017/0130902 A1* | 5/2017 | Oates | F17C 13/02 |
| 2018/0058972 A1* | 3/2018 | Zhang | G01M 15/14 |
| 2020/0355552 A1* | 11/2020 | Kreitinger | G01M 3/38 |
| 2022/0009648 A1 | 1/2022 | Clarke et al. | |
| 2022/0292895 A1* | 9/2022 | Ren | G08B 21/182 |
| 2023/0029650 A1* | 2/2023 | Tayebi | F01D 21/003 |
| 2023/0335990 A1* | 10/2023 | Aghatehrani | H02J 3/12 |

FOREIGN PATENT DOCUMENTS

| | | | | |
|---|---|---|---|---|
| CN | 113720537 A | * | 11/2021 | |
| CN | 113720537 B | * | 9/2022 | G01M 3/04 |
| WO | 2004027369 | | 4/2004 | |
| WO | 2019099567 A1 | | 5/2019 | |
| WO | 2022093289 | | 5/2022 | |

OTHER PUBLICATIONS

European Patent Office, "Extended European Search Report," issued in connection with European Patent Application No. 23212135.0, dated May 3, 2024, 10 pages.

European Patent Office, "Communication pursuant to Article 94(3) PC," issued in connection with European Patent Application No. 23212135.0, dated Mar. 25, 2026, 9 pages.

* cited by examiner

START

1400

SELECT ENVIRONMENTAL PARAMETER(S) — 1402

SELECT LEAK LOCATION PARAMETER(S) — 1404

SELECT LEAK FLOW RATE PARAMETER(S) — 1406

RUN FLUID DYNAMICS SIMULATION USING SELETED PARAMETERS — 1408

GENERATE MODEL DATA SET BY RECORDING SIMULATED HYDROGEN CONCENTRATIONS AT SENSOR LOCATIONS — 1410

SAVE MODEL DATA SET TO DATABASE — 1412

GENERATE ANOTHER MODEL DATA SET? — 1414

END

METHODS AND APPARATUS FOR MANAGING A HYDROGEN STORAGE AND DISTRIBUTION SYSTEM

FIELD OF THE DISCLOSURE

This disclosure relates generally to gas storage systems and, more particularly, to methods and apparatus for managing a hydrogen storage and distribution system.

BACKGROUND

Hydrogen storage systems include pressured and/or cooled hydrogen in liquid or gaseous forms. Hydrogen storage systems often include a number of components that contain and move hydrogen to other components of the system. Hydrogen storage systems can be used in power generation, in chemical manufacturing, among other applications.

BRIEF DESCRIPTION OF THE DRAWINGS

A full and enabling disclosure of the preferred embodiments, including the best mode thereof, directed to one of ordinary skill in the art, is set forth in the specification, which makes reference to the appended Figures, in which.

Figure 1A:
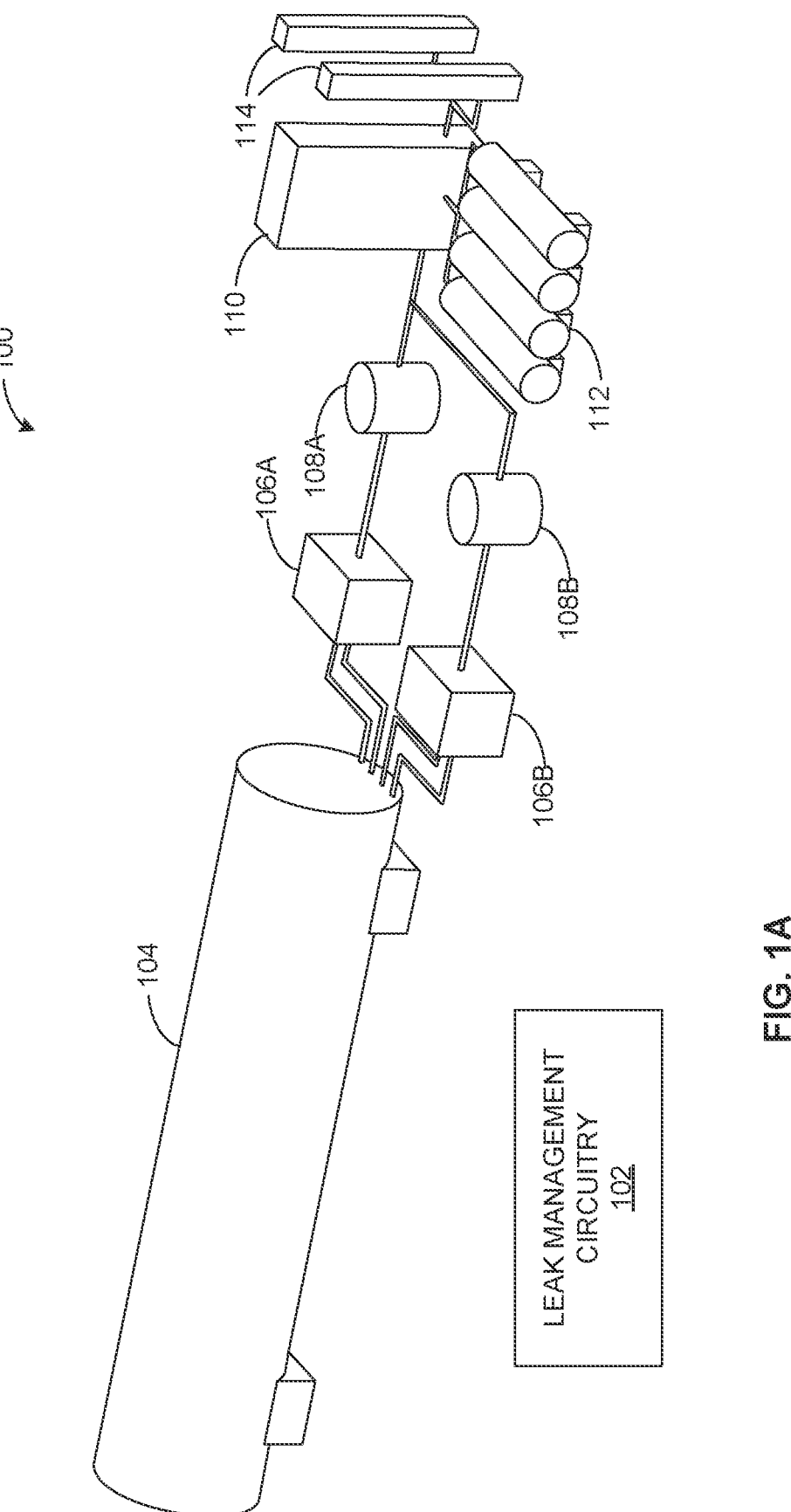
FIG. 1A is a perspective view of a hydrogen storage system in which the teachings of this disclosure may be implemented.

In general, the same reference numbers will be used throughout the drawing(s) and accompanying written description to refer to the same or like parts. The figures are not to scale. Instead, the thickness of the layers or regions may be enlarged in the drawings. Although the figures show layers and regions with clean lines and boundaries, some or all of these lines and/or boundaries may be idealized. In reality, the boundaries and/or lines may be unobservable, blended, and/or irregular.

DETAILED DESCRIPTION

Some existing hydrogen ($H_2$) leak detection systems in hydrogen storage, distribution, and/or fueling facilities can detect hydrogen leaks and can automatically shut down the hydrogen flow but cannot identify the source of the leak and quantify the flow rate of the leak. An example process disclosed herein can quantify a leak and identify the location of a leak in hydrogen facilities using data from hydrogen sensors and hydrogen leak simulations. In some such examples disclosed herein, sensors are dispersed in a hydrogen facility and collect hydrogen concentration data. In some such examples disclosed herein, such hydrogen concentration data is compared to the expected hydrogen concentration data for a variety of leak locations, and severities. In some examples disclosed herein, if the sensor data is similar to the data associated with a simulated leak scenario, the leak location and leak quantification is identified via the modeled leak location and the leak quantification of the similar scenario. Another example process disclosed herein can also identify the location and flow rate of a leak in hydrogen facilities using data from fixed hydrogen sensor (s), hydrogen leak simulation(s), and mobile sensor platform (s). In some examples disclosed herein, after the stationary sensors detect a leak, the mobile sensor platforms can be deployed to identify a location of the source of the leak.

As used herein, unless otherwise stated, the term "above" describes the relationship of two parts relative to Earth. A first part is above a second part, if the second part has at least one part between Earth and the first part. Likewise, as used herein, a first part is "below" a second part when the first part is closer to the Earth than the second part. As noted above, a first part can be above or below a second part with one or more of: other parts therebetween, without other parts therebetween, with the first and second parts touching, or without the first and second parts being in direct contact with one another.

As used in this application, stating that any part (e.g., a layer, film, area, region, or plate) is in any way on (e.g., positioned on, located on, disposed on, or formed on, etc.) another part, indicates that the referenced part is either in contact with the other part, or that the referenced part is above the other part with one or more intermediate part(s) located therebetween.

As used herein, connection references (e.g., attached, coupled, connected, and joined) may include intermediate members between the elements referenced by the connection reference and/or relative movement between those elements unless otherwise indicated. As such, connection references do not necessarily infer that two elements are directly connected and/or in fixed relation to each other. As used herein, stating that any part is in "contact" with another part is defined to mean that there is no intermediate part between the two parts.

Unless specifically stated otherwise, descriptors such as "first," "second," "third," etc., are used herein without imputing or otherwise indicating any meaning of priority, physical order, arrangement in a list, and/or ordering in any way, but are merely used as labels and/or arbitrary names to distinguish elements for ease of understanding the disclosed examples. In some examples, the descriptor "first" may be used to refer to an element in the detailed description, while the same element may be referred to in a claim with a different descriptor such as "second" or "third." In such instances, it should be understood that such descriptors are used merely for identifying those elements distinctly that might, for example, otherwise share a same name.

As used herein, "approximately" and "about" modify their subjects/values to recognize the potential presence of variations that occur in real world applications. For example, "approximately" and "about" may modify dimensions that may not be exact due to manufacturing tolerances and/or other real world imperfections as will be understood by persons of ordinary skill in the art. For example, "approximately" and "about" may indicate such dimensions may be within a tolerance range of +/−10% unless otherwise specified in the below description. As used herein "substantially real time" refers to occurrence in a near instantaneous manner recognizing there may be real world delays for computing time, transmission, etc. Thus, unless otherwise specified, "substantially real time" refers to real time+/−1 second. As used herein, two quantities are "substantially the same" and/or substantially equal if the two quantities are within 5% of each other.

As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

As used herein, "processor circuitry" is defined to include (i) one or more special purpose electrical circuits structured to perform specific operation(s) and including one or more semiconductor-based logic devices (e.g., electrical hardware implemented by one or more transistors), and/or (ii) one or more general purpose semiconductor-based electrical circuits programmable with instructions to perform specific operations and including one or more semiconductor-based logic devices (e.g., electrical hardware implemented by one or more transistors). Examples of processor circuitry include programmable microprocessors, Field Programmable Gate Arrays (FPGAs) that may instantiate instructions, Central Processor Units (CPUs), Graphics Processor Units (GPUs), Digital Signal Processors (DSPs), XPUs, or microcontrollers and integrated circuits such as Application Specific Integrated Circuits (ASICs). For example, an XPU may be implemented by a heterogeneous computing system including multiple types of processor circuitry (e.g., one or more FPGAs, one or more CPUs, one or more GPUs, one or more DSPs, etc., and/or a combination thereof) and application programming interface(s) (API(s)) that may assign computing task(s) to whichever one(s) of the multiple types of processor circuitry is/are best suited to execute the computing task(s).

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc., may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, or (7) A with B and with C. As used herein in the context of describing structures, components, items, objects and/or things, the phrase "at least one of A and B" is intended to refer to implementations including any of (1) at least one A, (2) at least one B, or (3) at least one A and at least one B. Similarly, as used herein in the context of describing structures, components, items, objects and/or things, the phrase "at least one of A or B" is intended to refer to implementations including any of (1) at least one A, (2) at least one B, or (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, or (3) at least one A and at least one B. Similarly, as used herein in the context of describing the performance or execution of processes, instructions, actions, activities and/or steps, the phrase "at least one of A or B" is intended to refer to implementations including any of (1) at least one A, (2) at least one B, or (3) at least one A and at least one B.

As used herein, singular references (e.g., "a", "an", "first", "second", etc.) do not exclude a plurality. The term "a" or "an" object, as used herein, refers to one or more of that object. The terms "a" (or "an"), "one or more", and "at least one" are used interchangeably herein. Furthermore, although individually listed, a plurality of means, elements or method actions may be implemented by, e.g., the same entity or object. Additionally, although individual features may be included in different examples or claims, these may possibly be combined, and the inclusion in different examples or claims does not imply that a combination of features is not feasible and/or advantageous.

In recent years, hydrogen-based systems have increased in popularity. Hydrogen-based storage, fueling, and/or distribution systems can be used to power and/or supply industry (e.g., a precursor in ammonia production, steel production, a precursor in methanol production, fossil fuel refining, etc.), vehicles (e.g., automobiles, gas turbine aircraft, etc.) and/or grid power. Generally, hydrogen must be highly pressurized and/or cryogenically cooled to be useful in such applications and can be stored as either a liquid or a gas. Liquid hydrogen (LH2) storage tanks are lighter than tanks filled with gaseous hydrogen (GH2) due to the reduced tank volume needed to store liquid hydrogen versus gaseous hydrogen. Liquid hydrogen requires temperature regulation to minimize heat transfer and allow the liquid hydrogen to remain cold, thereby avoiding the vaporization of the hydrogen over time. Given the high pressure of the stored hydrogen, the extremely low temperature of the hydrogen, and the high flammability of hydrogen, leaks from tanks and/or other components of hydrogen storage systems (e.g., pumps, valves, heat exchangers, pipe junctions, etc.) can be problematic. Additionally, the cost of compressing hydrogen to the high-pressure of fuel tanks is comparatively high, making leaks financially costly to hydrogen stores and consumers.

Existing hydrogen leak detection and safety systems for hydrogen storage, distribution, and fueling facilities include hydrogen sensors, which enable such systems to detect hydrogen leaks and shut down the system to prevent further leaking. However, such systems cannot identify the source of the leak and quantify the leak of the hydrogen lost from the leak. As used herein, "quantifying" of a leak (e.g., the quantifications of a leak, etc.) refers to determining the flow rate of hydrogen through the leak. As used herein, the term "severity" also refers to the flow rate of hydrogen through a leak (e.g., a first leak with a higher mass flow rate than a second leak has a greater severity, etc.). Because existing systems cannot identify the source of leaks, such leaks must be manually identified via inspection by technicians and often involve re-engaging the system to find the leak. The manual inspection of hydrogen systems can take a comparatively large amount of time (e.g., time for a technician to arrive at the system, time for a technician to find the leak, etc.) and a technician must engage the system to detect the leak.

Examples disclosed herein mitigate the above-referenced deficiencies by using data from an array of hydrogen sensors in a hydrogen storage system, ambient environment data, and model data of fluid dynamics simulations of hydrogen leaks to quantify and identify location of leaks in a hydrogen storage system. Examples disclosed herein compare data from multiple hydrogen concentration sensors to fluid flow model data sets of hydrogen leak scenarios to determine the similarity of the hydrogen concentrations of the scenario and the received sensor data. In some examples disclosed herein, if the hydrogen concentration sensor data and scenario concentration data satisfy a similarity threshold, a leak location and flow rate can be identified based on the modeled leak location and flow rate of the scenario. In some examples disclosed herein, ambient environmental conditions (e.g., wind speed, wind direction, temperature, humidity, etc.) can be used to filter (e.g., down select or otherwise reduce, etc.) scenarios. Examples disclosed herein make leak identification and repair safer, more accurate, and more efficient. In some examples disclosed herein, a mobile sensor platform can be deployed to the leak location to identify an exact leak location. In some such examples disclosed herein, the mobile sensor platform can be mounted on a drone. Examples disclosed herein can be used in outdoor hydrogen storage facilities (e.g., industrial applications, vehicle refueling systems, etc.) and/or internal hydrogen storage systems (e.g., vehicle fueling systems, etc.).

For the figures disclosed herein, identical numerals indicate the same elements throughout the figures.

Figure 1B:
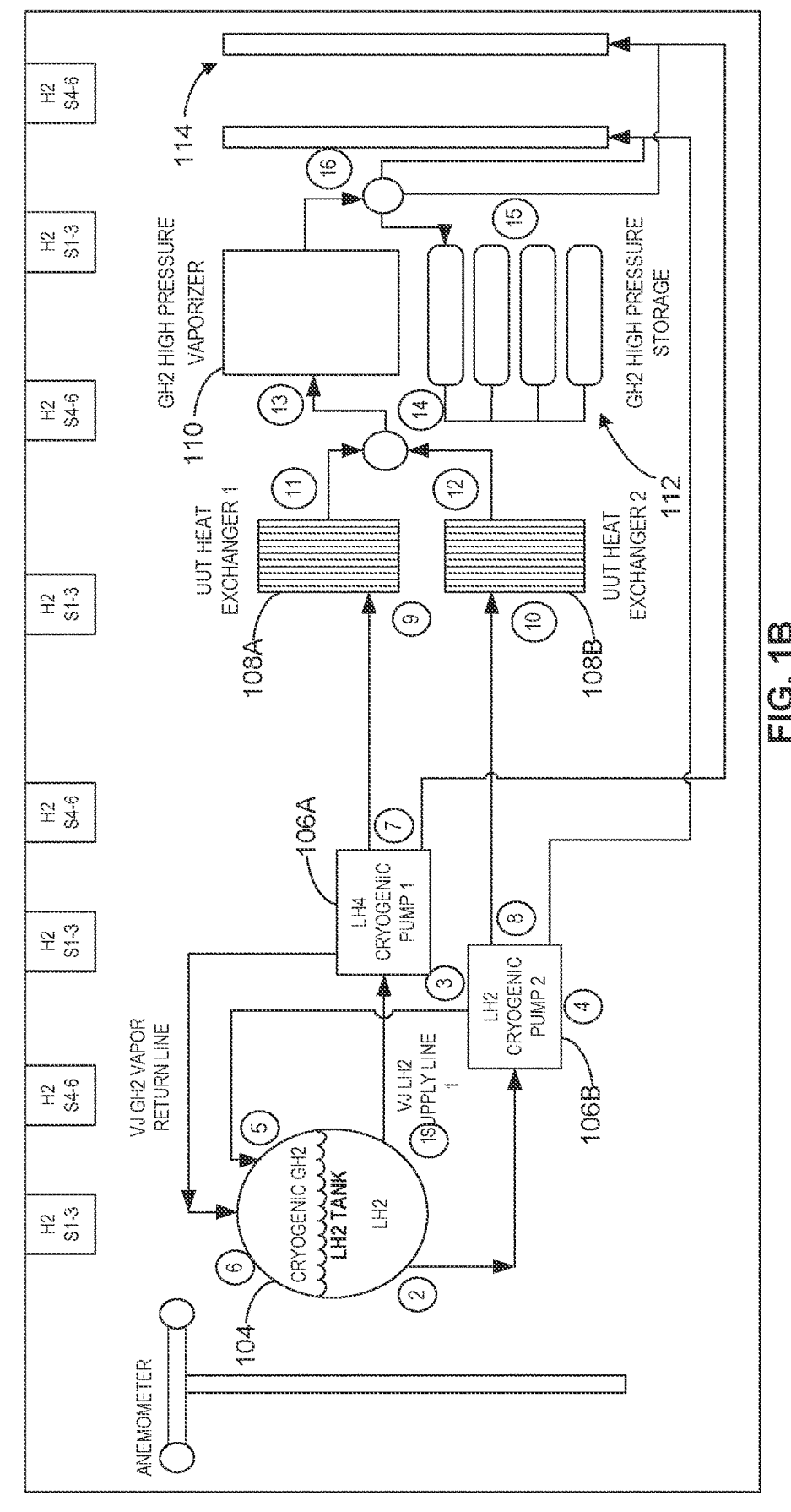
FIG. 1B is a schematic view of a hydrogen storage system of FIG. 1B.

FIG. 1A is a perspective view of an example hydrogen storage system 100 in which the teachings of this disclosure may be implemented. FIG. 1B is a schematic view of a hydrogen storage system 100 of FIG. 1B. In the illustrated examples of FIGS. 1A and 1B, the hydrogen storage system 100 includes an example hydrogen tank 104, an example first pump 106A, an example second pump 106B, an example first heat exchanger 108A, an example second heat exchanger 108B, an example vaporizer 110, an example gaseous hydrogen tank array 112, and example vent stacks 114. As used herein, the hydrogen tank 104, the pumps 106A, 106B, the heat exchangers 108A, 108B, the vaporizer 110, the gaseous hydrogen tank array 112, the vent stacks 114, and the piping extending therebetween are referred to as components of the hydrogen storage system 100. In other examples, the hydrogen storage system 100 can include any other suitable components.

The hydrogen storage system 100 is a system that stores hydrogen for use as a power source, a chemical precursor, and/or any other suitable purpose. The hydrogen storage system 100 includes components that enable the storage of highly compressed gases and the distribution of such to other components (e.g., to fill other tanks, to fill vehicles, etc.). Although the hydrogen storage system 100 shown in FIG. 1A is a hydrogen storage system in an example open environment (e.g., outside, etc.), the embodiments described herein may also be applicable to hydrogen storage systems in other environments (e.g., inside a building, inside a vehicle, etc.). As used herein, vehicles include trains, automobiles, fixed-wing aircrafts, including unmanned aerial vehicles (UAV), rotary-wing aircraft, and/or any other suitable type of aircraft. In some such examples, the hydrogen storage system 100 can be used to provide hydrogen fuel that will be combusted in one or more powerplant(s) (e.g., a gas turbine engine, etc.) of the vehicle. It should also be appreciated that the hydrogen storage system 100 can have many other configurations.

The hydrogen tank 104 is a mechanical structure that contains compressed hydrogen ($H_2$). The example hydrogen tank 104 can contain hydrogen in various states, including liquid, gaseous, and cryo-compressed states. In the illustrated example of FIGS. 1A and 1B, the hydrogen tank 104 is a liquid hydrogen tank. Additionally or alternatively, the hydrogen tank 104 can include multiple tanks (herein referred to as a tank bank or a tank array, etc.). The pumps 106A, 106B are configured to provide a flow of hydrogen from the hydrogen tank 104 in a liquid phase from the hydrogen tank 104 to the heat exchangers 108A, 108B, the vaporizer 110, and the gaseous hydrogen tank array 112. In some examples, operation of the pumps 106A, 106B can be modulated (e.g., increased, decreased, etc.) to effectuate a change in a volume of the hydrogen flowing from the hydrogen tanks 104. The pumps 106A, 106B can be any suitable pumps configured to provide a flow of liquid hydrogen fuel. In some examples, the pumps 106A, 106B are cryogenic pumps.

The heat exchangers 108A, 108B are physical structures and are located downstream of the pumps 106A, 106B and are configured to convert a portion of the hydrogen flowing therethrough through from the liquid phase to a gaseous phase. In some examples, the heat exchangers 108A, 108B can use any suitable medium to increase the temperature of the hydrogen flowing there through, including water, refrigerants, glycol mixes, liquid nitrogen, air, and/or any other suitable heat exchange mediums. In some examples, the heat exchangers 108A, 108B can be implemented by one or more double-pipe heat exchangers, one or more shell and tube heat exchangers, one or more plate heat exchangers, and/or any other suitable heat exchangers.

The vaporizer 110 transfers liquid hydrogen into gaseous hydrogen for storage in the gaseous hydrogen tank array 112. In some examples, the vaporizer 110 can include a heat exchanger to vaporize the hydrogen. In other examples, the vaporizer 110 can vaporizer the hydrogen in any suitable fashion. The gaseous hydrogen tank array 112 stores hydrogen in a gaseous phase. The gaseous hydrogen tank array 112 can be configured to store the first portion of hydrogen fuel at an increased pressure to reduce a necessary size of the gaseous hydrogen tank array 112 (e.g., for vehicle-based applications, etc.). For example, the gaseous hydrogen tank array 112 can be configured to store the first portion of hydrogen fuel at a pressure from about 100 bar up to about 1,000 bar. The gaseous hydrogen tank array 112 can be configured to store the hydrogen at a temperature within about 50° C. of an ambient temperature, or between about −50° C. and about 50° C. In some examples, the gaseous hydrogen tank array 112 is configured as a plurality of tanks to reduce an overall size and weight that would otherwise be needed to contain the desired volume of the first portion of hydrogen fuel in the gaseous phase at the desired pressures.

The vent stacks 114 vent hydrogen into the surrounding atmosphere. For example, the vent stacks 114 can vaporize hydrogen that leaks through the valves that control the flow of hydrogen through the hydrogen storage system 100. The leak management circuitry 102 identifies the locations of the leak in the hydrogen storage system 100 by comparing hydrogen concentration(s) in the environment around the hydrogen storage system 100 to the predicted hydrogen concentrations associated with simulated hydrogen leaks. An example sensor configuration to determine the hydrogen concentration(s) in the ambient environment to the hydrogen storage system 100 is described below in conjunction with FIGS. 4A and 4B. In some examples, the leak management circuitry 102 can filter the quantity of predicted hydrogen concentration data sets to which the sensed hydrogen concentration data is to be compared based on environmental data (e.g., wind speed, wind direction, temperature, humidity, etc.) received from sensors in the environment around the leak management circuitry 102. An example implementation of the leak management circuitry 102 is described below in conjunction with FIG. 6.

In some examples, after quantifying the leak and identifying the location of the leak, the leak management circuitry 102 can isolate a leak and/or take other mitigation efforts. As used herein, the phrase "isolating a leak" refers to preventing hydrogen from flowing to the potential leak location without stopping the operation of the hydrogen storage system 100. The leak management circuitry 102 can isolate a leak by selectively disabling redundant components of the hydrogen storage system 100 (e.g., one of the pumps 106A, 106B, etc.) and/or by closing the valve on a redundant hydrogen line (e.g., not illustrated, etc.) running between components. The ability to isolate a leak without disabling the hydrogen storage system 100 enables the hydrogen storage system 100 to continue to safely function after identifying the leak, which is advantageous in situations where the continuous function of the hydrogen storage system 100 is needed for operation (e.g., if the hydrogen storage system 100 supplies hydrogen for the operation of an aircraft and/or a spacecraft, etc.). In some examples, if the leak management circuitry 102 determines it is not possible to isolate the leak, the leak management circuitry 102 can disable the hydrogen storage system 100 (e.g., by stopping all flow of hydrogen between components of the hydrogen storage system 100, etc.).

Figure 2:
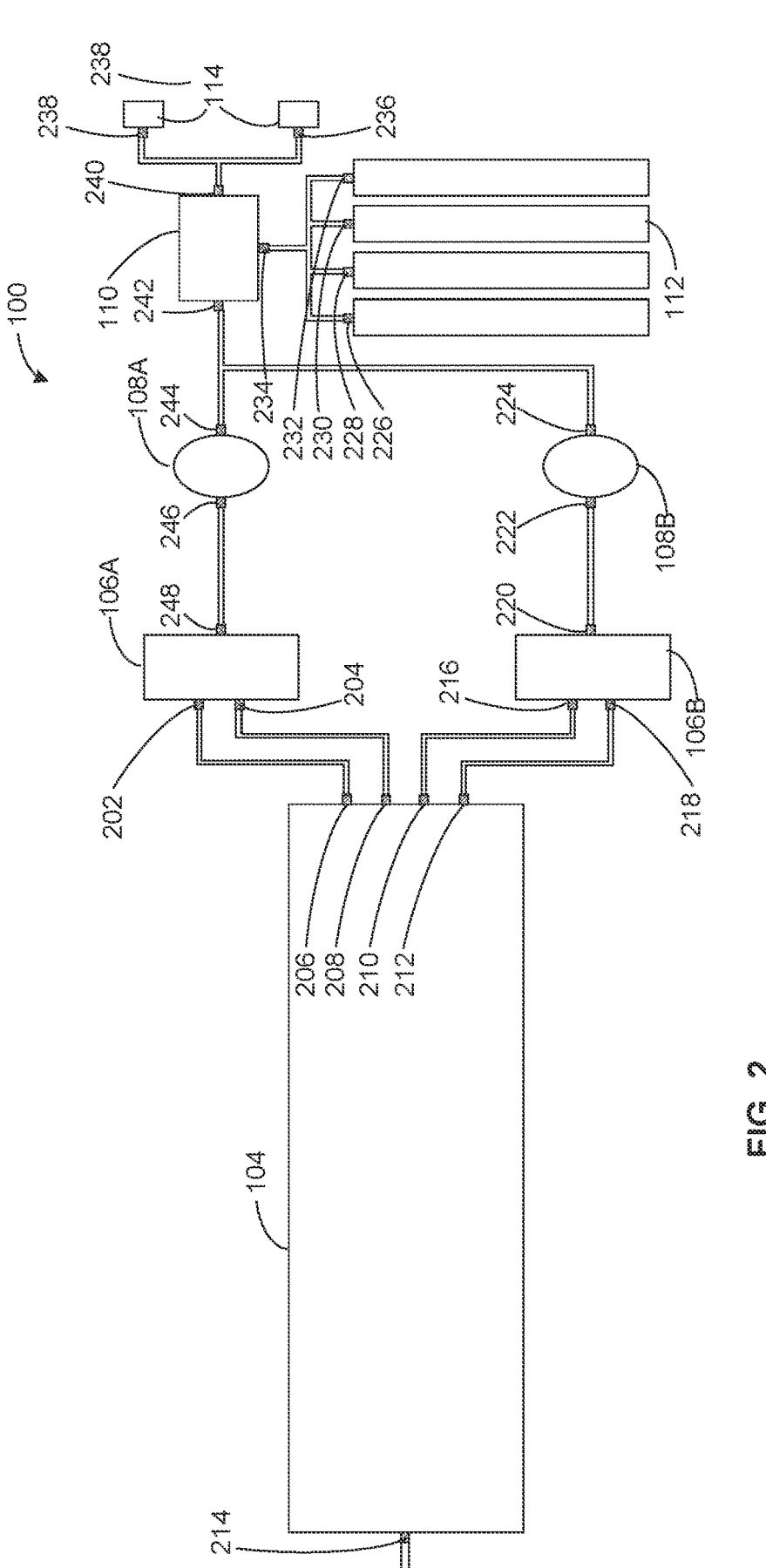
FIG. 2 is a top view of the hydrogen storage system of FIGS. 1A and 1B depicting potential leak locations.

FIG. 2 is a top view of the hydrogen storage system 100 of FIGS. 1A and 1B depicting potential leak locations. In the illustrated example, the hydrogen storage system 100 includes an example first potential leak location 202, an example second potential leak location 204, an example third potential leak location 206, an example fourth potential leak location 208, an example fifth potential leak location 210, an example sixth potential leak location 212, an example seventh potential leak location 214, an example eighth potential leak location 216, an example ninth potential leak location 218, an example tenth potential leak location 220, an example eleventh potential leak location 222, an example twelfth potential leak location 224, an example thirteenth potential leak location 226, example fourteenth potential leak location 228, an example fifteenth potential leak location 230, an example sixteenth potential leak location 232, an example seventeenth potential leak location 234, an example eighteenth potential leak location 236, an example nineteenth potential leak location 238, an example twentieth potential leak location 240, an example twenty-first potential leak location 242, an example twenty-second potential leak location 244, an example twenty-third potential leak location 246, and example twenty fourth potential leak location 248.

The potential leak locations 202-246 are locations that are likely to have leaks during operation of the hydrogen storage system 100. In some examples, due to the low molecular volume of hydrogen (e.g., the $H_2$ molecules, etc.), leaks of hydrogen are common in any components that seal separate gaseous and/or vaporous hydrogen from the surrounding atmosphere. As such, the potential leak locations 202-246 are disposed at the junction between components of the hydrogen storage system 100. In some such examples, due to the high density of the hydrogen stored in the hydrogen storage system 100 and the low molecular volume of hydrogen, hydrogen leaks at the potential leak locations 202-246 can be difficult to identify visually.

Figure 3:
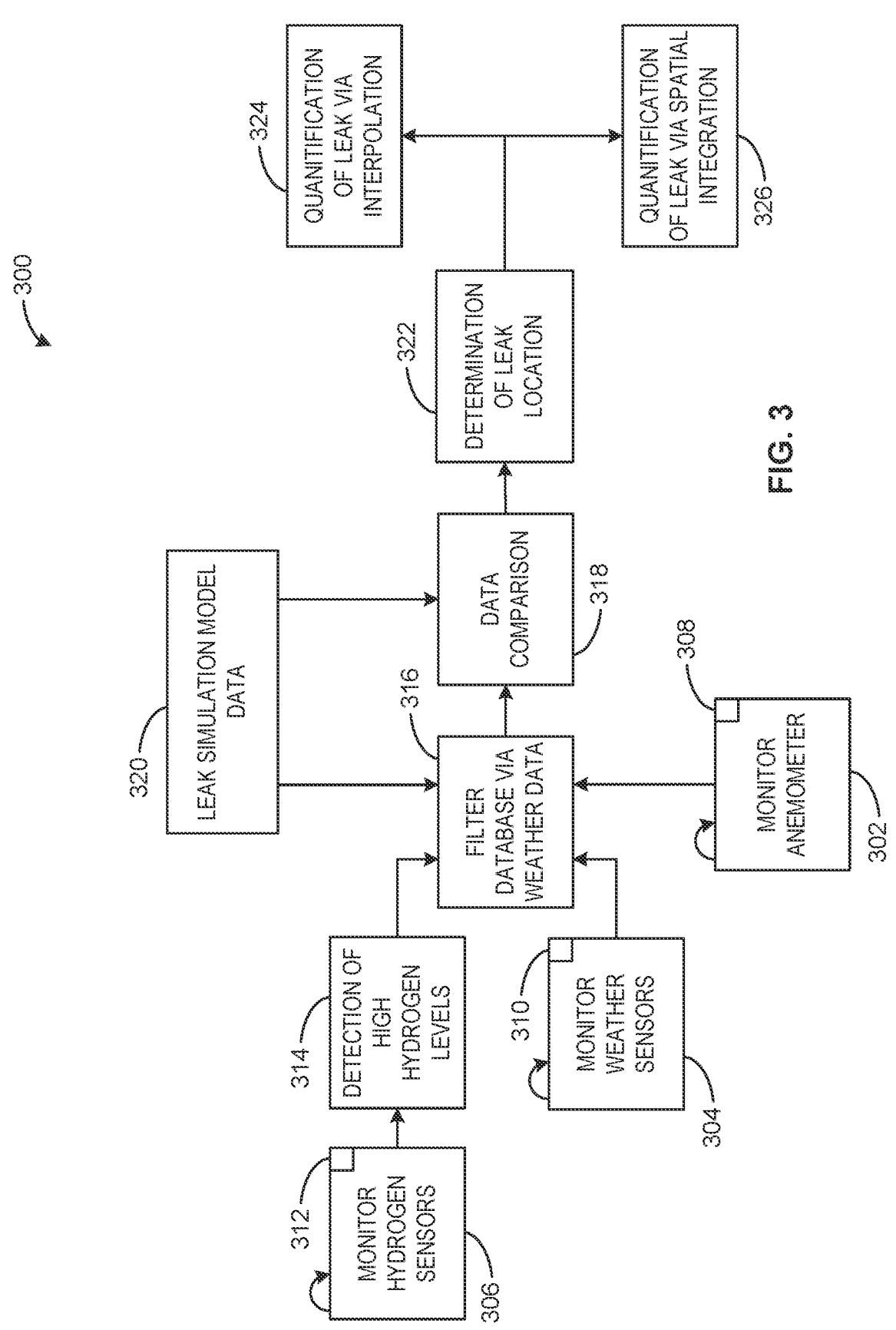
FIG. 3 is a process diagram of a leak detection process that can be used with the hydrogen storage system of FIGS. 1A-2.

FIG. 3 is a process diagram of an example leak detection process 300 that can be used with the hydrogen storage system of FIGS. 1A-2. In the illustrated example of FIG. 3, the example leak detection process 300 includes an example anemometer monitoring subprocess 302, an example weather sensor monitoring subprocess 304, and an example hydrogen sensor monitoring subprocess 306, which monitors example anemometer data 308, example temperature and humidity data 310, and example hydrogen concentration data 312. In the illustrated example of FIG. 3, the leak detection process 300 includes an example detection subprocess 314 and example filtering subprocess 316. The leak detection process 300 includes an example data comparison subprocess 318, which compares the collected data (e.g., the anemometer data 308, the humidity data 310, the hydrogen concentration data 312, etc.) with an example leak simulation model data 320. After conducting the data comparison subprocess 318, the leak detection process 300 includes an example leak identification subprocess 322, an example first leak quantification subprocess 324, and an example second leak quantification subprocess 326.

Figure 4A:
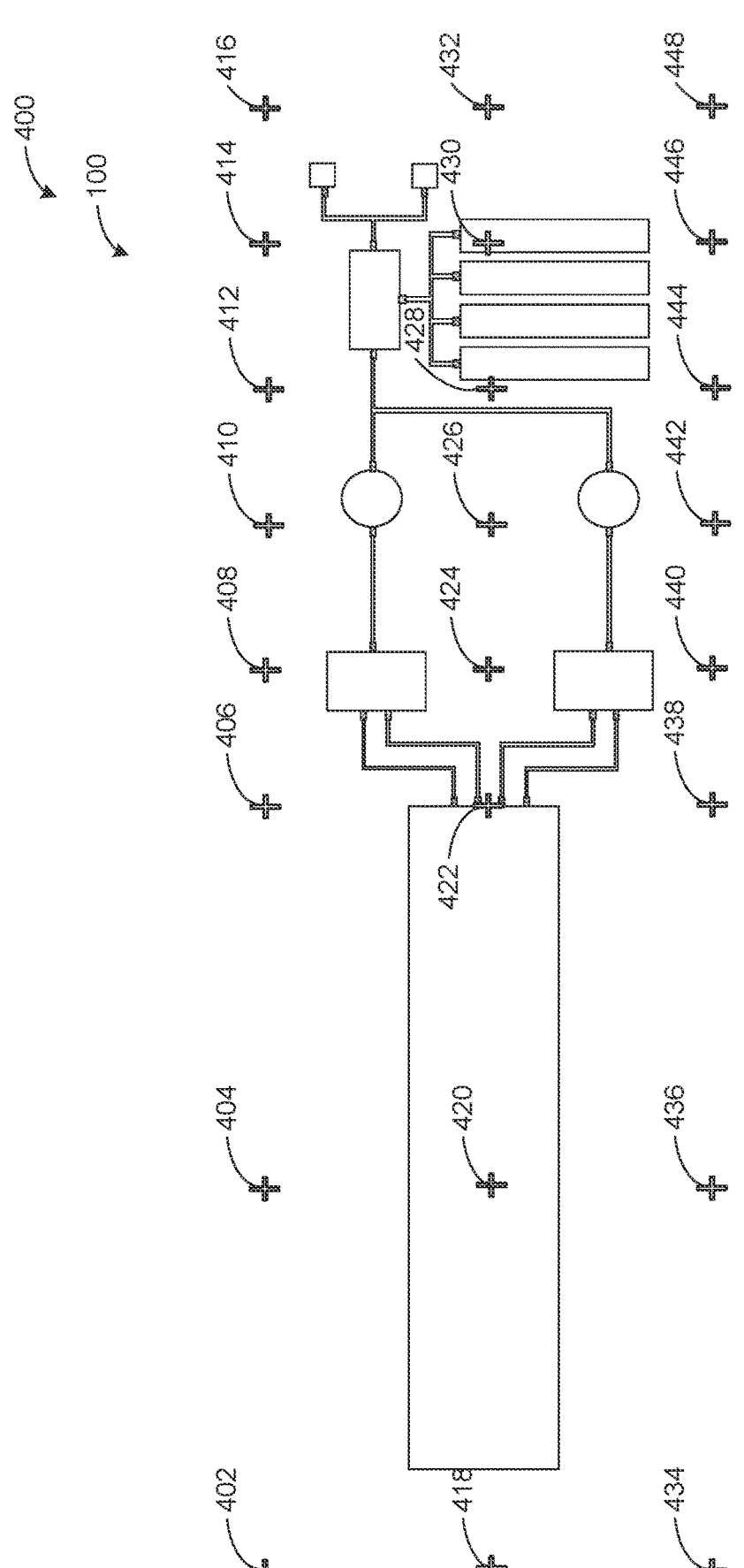
FIG. 4A is a top view of a hydrogen storage system of FIGS. 1A-2 depicting an example sensor layout that can be used in conjunction with the leak detection process of FIG. 3.
Figure 4B:
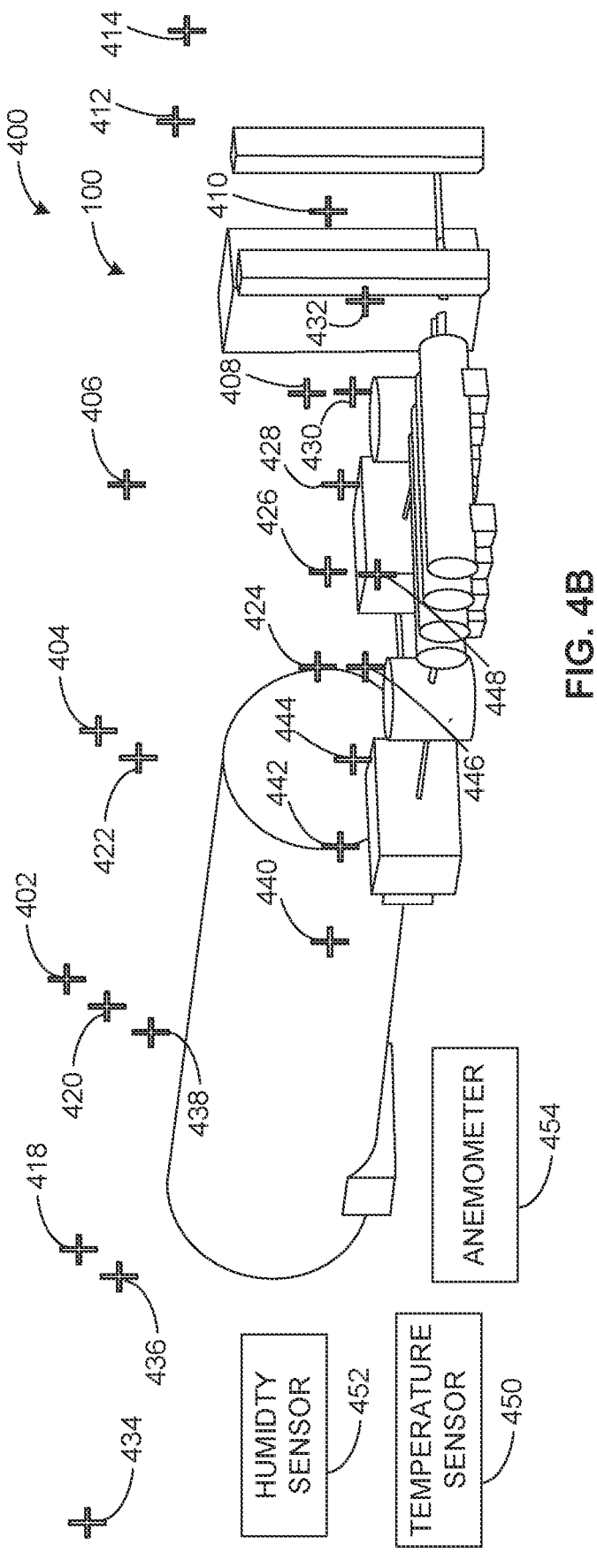
FIG. 4B is a perspective view of a hydrogen storage system of FIGS. 1A-2 showing the sensor layout of FIG. 4A.

The anemometer monitoring subprocess 302 accesses (e.g., collects, receives, etc.) the anemometer data 308 (e.g., receives sensor readings at a predetermined interval, receives a continuous sensor output, etc.) from an anemometer associated with the hydrogen storage system 100 of FIG. 1 (e.g., the anemometer 454 of FIG. 4B, etc.). The anemometer data 308 is data reflective of the wind speed and direction in the area around the hydrogen storage system 100. In some examples, the anemometer data 308 can be received via an anemometer disposed at the hydrogen storage system 100. Additionally or alternatively, the anemometer data 308 can be accessed from a weather service associated with the geographic location of the hydrogen storage system 100. Additionally or alternatively, the anemometer data 308 can be estimated based on historic data associated with the geographic location of the hydrogen storage system 100 (e.g., if the geographic location of the hydrogen storage system 100 has predictable wind speed and severities, etc.).

The weather sensor monitoring subprocess 304 accesses (e.g., collects, receives, etc.) the hydrogen concentration data 312 (e.g., receives sensor readings at a predetermined interval, receives a continuous sensor output, etc.) from sensors associated with the hydrogen storage system 100 of FIG. 1 (e.g., the temperature sensor 450 of FIG. 4B, the humidity sensor 452, etc.). The temperature and humidity data 310 is data reflective of the ambient environment and humidity of the hydrogen storage system 100. The temperature and humidity data 310 can be collected via sensors disposed in and/or proximate to the hydrogen storage system 100. Additionally or alternatively, the temperature and humidity data 310 can be accessed from a weather service associated with the geographic location of the hydrogen storage system 100. In some examples, the temperature and humidity data 310 can be estimated based on historic data associated with the geographic location of the hydrogen storage system 100. While the weather sensor monitoring subprocess 304 is described as collecting the temperature and humidity data 310 in FIG. 3, in other examples, the weather sensor monitoring subprocess 304 can access any other suitable ambient weather conditions (e.g., air pressure, presence/proportion of particular gases in the ambient air, presence/proportion of particular particulates in the ambient air, etc.).

The hydrogen sensor monitoring subprocess 306 accesses (e.g., collects, receives, etc.) the hydrogen concentration data 312 (e.g., receives sensor readings at a predetermined interval, receives a continuous sensor output, etc.) from sensors associated with the hydrogen storage system 100 of FIG. 1 (e.g., the sensors 402-448 of FIGS. 4A and 4B, etc.). The hydrogen concentration data 312 is data indicative of the concentration of hydrogen at various locations in and around the hydrogen storage system 100. For example, the hydrogen concentration data 312 can be a series of discrete values corresponding to the output of a plurality of hydrogen concentration sensors (e.g., a part per million (ppm) of hydrogen, a percentage of hydrogen in ambient air by mass, a percentage of hydrogen by volume, etc.). In some examples, the hydrogen concentration data 312 can be arranged in a matrix, a vector, and/or any other data structure. In other examples, the hydrogen concentration data 312 can be formatted as a function (e.g., a function that receives a location as an inputs and outputs a hydrogen concentration, etc.). An example configuration of hydrogen sensors is described below in conjunction with FIGS. 4A and 4B.

The detection subprocess 314 includes a detection of an elevated hydrogen concentration at one or more of the sensors being monitored by the hydrogen sensor monitoring subprocess 306. For example, the detection subprocess 314 can involve a detection of hydrogen concentration data at one or more of the sensors above the expected ambient hydrogen concentration. In other examples, the detection subprocess 314 can involve an elevated hydrogen level at multiple sensors and/or for a prolonged period of time. In some examples, the detect subprocess 314 can be modified and/or disabled for hydrogen concentration sensors near the vent stacks 114 if the vent stacks 114 are currently venting hydrogen from the hydrogen storage system 100.

The leak simulation model data 320 includes records of simulated hydrogen leaks. For example, a computational fluid dynamics simulation can simulate a hydrogen leak by modeling the hydrogen storage system 100 (e.g., the surfaces of the component of the hydrogen environment, etc.) and simulating a hydrogen leak at one of the potential leak locations 202-246 at a given flow rate (e.g., 0.5 kilograms per second, 1 kilogram per second, 10 kilograms per second, etc.). In some such examples, the leak simulation model data 320 can model ambient conditions corresponding to the wind speed and direction, the ambient humidity (e.g., 0% humidity, 25% humidity, 75% humidity, etc.), and the ambient temperature (e.g., 0 degrees Celsius, 20 degrees Celsius, etc.). After simulating these parameters, the computational fluid dynamics simulation can determine the steady-state and/or transient hydrogen concentrations at locations corresponding to the hydrogen concentration data 312. Example operations that can be used to generate the leak simulation model data 320 are described below in conjunction with FIG. 14.

The filtering subprocess 316 filters the leak simulation model data 320 based on the collected the anemometer data 308 and the temperature and humidity data 310. For example, the data comparison subprocess 318 can only compare instances of the leak simulation model data 320 that have the same modeled wind, temperature, and humidity data as the collected anemometer data 308 and the temperature and humidity data 310. The data comparison subprocess 318 compares the collected hydrogen concentration data 312 to the leak simulation model data 320. In other examples (e.g., the filter subprocess 316 is not conducted, the filtering subprocess 316 is inconclusive, etc.), the data comparison subprocess 318 can compare each data set of the leak simulation model data 320 to the collected hydrogen concentration data 312. In some such examples, the data comparison subprocess 318 can compare instances of the leak simulation model data 320 that are similar to the collected hydrogen concentration data 312 (e.g., satisfy a similarity threshold, etc.).

The leak identification subprocess 322 identifies the location of the source of the leak based on the instance of the leak simulation model data 320 that the data comparison subprocess 318 identified. For example, the leak identification subprocess 322 can identify the leak location as the modeled leak location associated with the identified instance. The first leak quantification subprocess 324 quantifies the leak based on the flow rate of the leak associated with the identified instance. In other examples, the leak identification subprocess 322 can include any alternative or additional processes. For example, the first leak quantification subprocess 324 can interpolate a flow rate of the leak based on the received hydrogen concentration data 312 and an identified instance of the leak simulation model data 320. The subprocesses 322, 324 are described in conjunction below with FIG. 7.

The second leak quantification subprocess 326 uses a comparatively dense array of hydrogen concentration sensors (e.g., collected by the hydrogen sensor monitoring subprocess 306 of FIG. 3, etc.). In some examples, the second leak quantification subprocess 326 can be conducted by estimating a hydrogen flow rate through a surface defined by the hydrogen concentration sensors (e.g., via integrating the hydrogen flow rate over the surface defined by the hydrogen concentration sensors, etc.). In some examples, the second leak quantification subprocess 326 can involve a greater density of hydrogen concentration sensors than the first leak quantification subprocess 324. For example, the second leak quantification subprocess 326 used in conjunction with the hydrogen storage system 100 of FIGS. 1A and 1B could involve the use of approximately one thousand hydrogen sensors. The subprocesses 326 are described in conjunction below with FIG. 8.

FIG. 4A is a top view of a hydrogen storage system 100 of FIGS. 1A-2 depicting an example sensor configuration 400. FIG. 4B is a perspective view of a hydrogen storage system 100 of FIGS. 1A-2 showing the sensor layout of FIG. 4A. The example sensor configuration 400 includes a first hydrogen concentration sensor 402, a second hydrogen concentration sensor 404, a third hydrogen concentration sensor 406, a fourth hydrogen concentration sensor 408, a fifth hydrogen concentration sensor 410, a sixth hydrogen concentration sensor 412, a seventh hydrogen concentration sensor 414, an eighth hydrogen concentration sensor 416, a ninth hydrogen concentration sensor 418, a tenth hydrogen concentration sensor 420, an eleventh hydrogen concentration sensor 422, a twelfth hydrogen concentration sensor 424, a thirteenth hydrogen concentration sensor 426, a fourteenth hydrogen concentration sensor 428, a fifteenth hydrogen concentration sensor 430, a sixteenth hydrogen concentration sensor 432, a seventeenth hydrogen concentration sensor 434, an eighteenth hydrogen concentration sensor 436, a nineteenth hydrogen concentration sensor 438, an twentieth hydrogen concentration sensor 440, a twenty-first hydrogen concentration sensor 442, a twenty-second hydrogen concentration sensor 444, a twenty-third hydrogen concentration sensor 446, and a twenty fourth hydrogen concentration sensor 448. In the illustrated example of FIG. 4B, the sensor configuration also includes an example temperature sensor 450, an example humidity sensor 452, and an example anemometer sensor 454.

In the illustrated examples of FIGS. 4A and 4B, the sensor configuration 400 includes the hydrogen concentration sensors 402-448 arranged in a grid (e.g., matrix, etc.) around each of the components of the hydrogen storage system 100. In the illustrated example of FIGS. 4A and 4B, the hydrogen concentration sensors 402-448 are generally positioned above the components of the hydrogen storage system 100 due to the tendency of hydrogen to rise in air. In the illustrated example of FIGS. 4A and 4B, the hydrogen concentration sensors 402, 404, 406, 418, 420, 434, 436 are positioned above the hydrogen tank 104; the hydrogen concentration sensors 408, 424, 440 are positioned above the pumps 106A, 106B; the hydrogen concentration sensors 410, 426, 442 are positioned above the heat exchangers 108A, 108B; the hydrogen concentration sensors 412, 414, 428, 430, 444, 446 are positioned above the vaporizer 110 and the gaseous hydrogen tank array 112; and the hydrogen concentration sensors 416, 432, 448 are positioned above the vent stacks 114. In other examples, any other suitable number of hydrogen sensors can be disposed adjacent to and/or above each of the components of the hydrogen storage system 100.

In the illustrated examples of FIGS. 4A and 4B, the sensor configuration 400 is such that the hydrogen concentration sensors 402, 404, 406, 412, 414 418, 420, 422, 434, 436, 438 are disposed in a first plane (e.g., a first plane at a first vertical displacement from the ground, etc.), and the hydrogen concentration sensors 408, 410, 424, 426, 428, 430, 432, 440, 442, 444, 446, 448 are disposed in a second plane (e.g., a second plane at a second vertical displacement from the ground, etc.). In other examples, the sensor configuration 400 can include sensors disposed in any other suitable configuration based on the properties of the hydrogen storage system 100 including, but not limited to, the location of high-frequency potential leaks in the hydrogen, the layout of the hydrogen storage system 100, the components of the hydrogen storage system 100, the enclosure of the hydrogen storage system 100 (e.g., if the hydrogen storage system 100 is inside a building, if the hydrogen storage system 100 is inside a vehicle, etc.).

The determine the relative concentration of hydrogen in the gas (e.g., air, etc.) in the ambient air surrounding each of the respective ones of the hydrogen concentration sensors 402-448. In some examples, each of the hydrogen concentration sensors 402-448 outputs an electrical parameter (e.g., a voltage, a current, etc.) that corresponds to a particular concentration of hydrogen around the corresponding one of the hydrogen concentration sensors 402-448. In some examples, the hydrogen concentration sensors 402-448 can be implemented by one or more optical sensors (e.g., a palladium-based sensor, an optical fiber surface plasmon resonance (SPR), etc.), one or more electrochemical sensors, one or more electrical mechanical sensors, one or more semiconductor-based sensors, one or more chemo-chronic hydrogen sensors, one or more Schottky-diode sensors, and/or a combination thereof.

The temperature sensor 450 is a device that outputs a digital value indicative of the ambient temperature of the hydrogen storage system 100. In some examples, the temperature sensor 450 can be implemented by one or more infrared sensors, one or more thermocouples, one or more resistance temperature detectors, one or more thermistors, and/or one or more semiconductor-based sensors, one or more bimetallic sensors, one or more thermometers, etc. In some examples, the temperature sensor 450 can be implemented by a plurality of temperature sensors in situations where the hydrogen storage system 100 is at a location where the temperature may vary at different parts of the hydrogen storage system 100 (e.g., if the hydrogen storage system 100 is disposed in a vehicle, if the hydrogen storage system 100 is distributed over a large geographic area, one or more of the components of the hydrogen storage system 100 generates a large amount of heat, etc.).

The humidity sensor 452 is a device that outputs a digital value indicative of the ambient humidity of the hydrogen storage system 100. In some examples, the humidity sensor 452 can be implemented by one or more capacitive humidity sensors, one or more resistive humidity sensors, and/or one more thermal humidity sensors. In some examples, the humidity sensor 452 can be implemented by a plurality of temperature sensors in situations where the hydrogen storage system 100 is at a location where the humidity may vary at different parts of the hydrogen storage system 100 (e.g., if the hydrogen storage system 100 is disposed in a vehicle, if the hydrogen storage system 100 is distributed over a large geographic area, etc.).

In some examples, some or all of the anemometer 454, the temperature sensor 450 and/or the humidity sensor 452 can be absent. In other such examples, the wind condition, ambient temperature, and/or the ambient humidity can be determined by accessing such information from a weather service, using historic data indicative of such information, and/or by any other suitable means.

Figure 5:
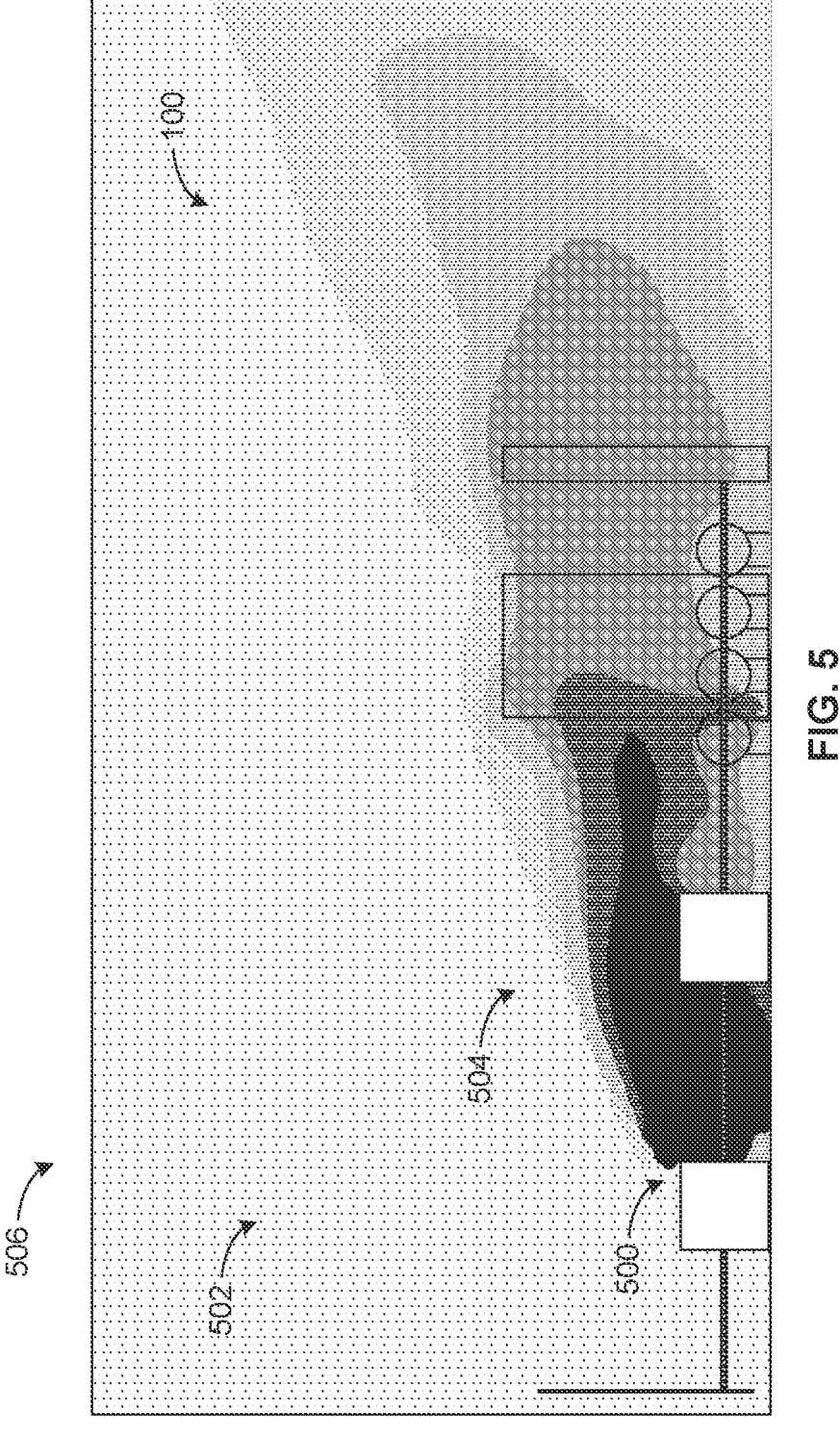
FIG. 5 is a side view of a simulated hydrogen leak of the hydrogen storage system of FIGS. 1A-2.

FIG. 5 is a side view of a simulated hydrogen leak 500 of the hydrogen storage system 100 of FIGS. 1A-2. In the illustrated example of FIG. 5, the simulated hydrogen leak 500 includes a simulated hydrogen leak at the twenty fourth potential leak location 248 of FIG. 2 with example simulated ambient conditions 502. The example simulated ambient conditions 502 include a temperature parameter, a humidity temperature, a wind speed parameter, and a wind direction parameter. The simulated ambient conditions 502 and the simulated hydrogen leak 500 at the twenty fourth potential leak location 248 cause an example hydrogen distribution 504 in an example region 506 around the hydrogen storage system 100. In the illustrated example of FIG. 5, areas of the hydrogen distribution 504 with denser dot patterns correspond to areas of the hydrogen distribution 504 with great concentrations of hydrogen.

In some examples, due to the low molecular weight of hydrogen and the high pressure of the hydrogen in the hydrogen storage system 100, hydrogen from the simulated hydrogen leak 500 and/or actual leaks in the hydrogen storage system quickly reaches a steady-state condition (e.g., within less than ten seconds, etc.) where the hydrogen distribution is steady (e.g., is no longer time-variant, etc.). As such, in some examples, the leak management circuitry 102 can store the steady state condition of the hydrogen distribution 504. Additionally or alternatively, the leak management circuitry 102 can store one or more transient hydrogen distributions corresponding to the hydrogen distribution 504. In some such examples, the leak management circuitry 102 can use transient hydrogen distributions to identify and mitigate the simulated hydrogen leak 500 before it reaches a steady-state condition. In some examples, the leak management circuitry 102 can store the location and the flow rate of the simulated hydrogen leak 500, the hydrogen distribution 504, the temperature parameter, the humidity temperature, the wind speed parameter, and the wind direction parameter as an instance of the leak simulation model data 320 of FIG. 3.

Figure 6:
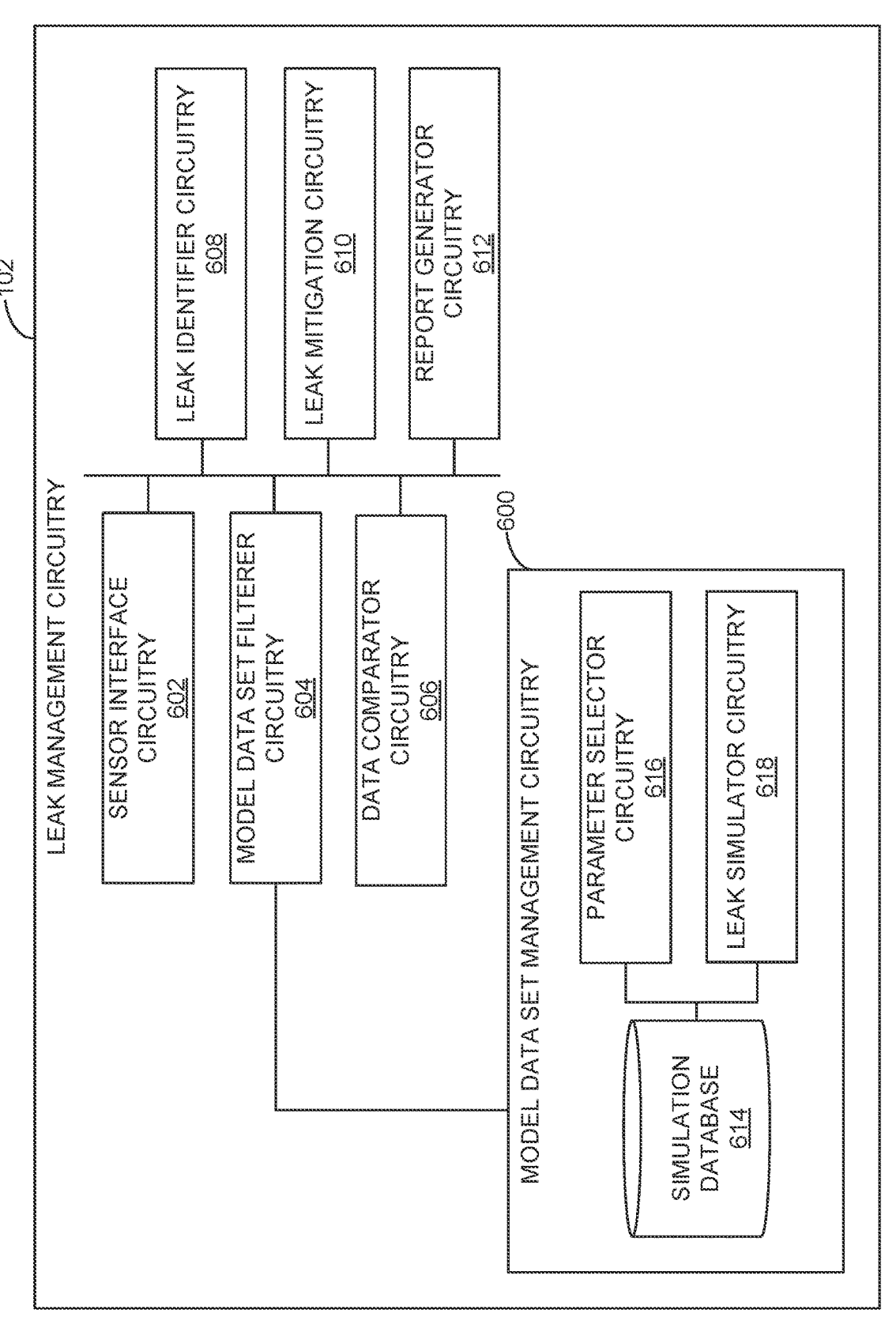
FIG. 6 is a block diagram of the example leak management system of FIGS. 1A and 1B.

FIG. 6 is a block diagram of the leak management circuitry 102 to detect and mitigate the leaks of the hydrogen storage system of FIGS. 1A-2. In the illustrated example of FIG. 6, the leak management circuitry 102 includes model data set management circuitry 600, sensor interface circuitry 602, model data set filterer circuitry 604, data comparator circuitry 606, leak identifier circuitry 608, leak mitigation circuitry 610 and report generator circuitry 612. In the illustrated example of FIG. 6, the model data set management circuitry 600 includes a simulation database 614, parameter selector circuitry 616, and leak simulator circuitry 618. The leak management circuitry 102 of FIG. 6 may be instantiated (e.g., creating an instance of, bring into being for any length of time, materialize, implement, etc.) by processor circuitry such as a central processing unit executing instructions. Additionally or alternatively, the leak management circuitry 102 of FIG. 6 may be instantiated (e.g., creating an instance of, bring into being for any length of time, materialize, implement, etc.) by an ASIC or an FPGA structured to perform operations corresponding to the instructions. It should be understood that some or all of the circuitry of FIG. 6 may, thus, be instantiated at the same or different times. Some or all of the circuitry may be instantiated, for example, in one or more threads executing concurrently on hardware and/or in series on hardware. Moreover, in some examples, some or all of the circuitry of FIG. 6 may be implemented by microprocessor circuitry executing instructions to implement one or more virtual machines and/or containers.

The sensor interface circuitry 602 can accesses sensor data from the environmental sensors and the hydrogen concentration sensors of the hydrogen storage system 100. For example, the sensor interface circuitry 602 can receive sensor data from the sensors 402-454 of the hydrogen storage system 100 of FIGS. 4A and 4B. Additionally or alternatively, the sensor interface circuitry 602 can interface with external sensors (e.g., other sensors at the facility housing the hydrogen storage system 100 and/or a weather service to determine the environmental data. In some examples, the sensor interface circuitry 602 can transform the received sensor data from a machine-readable format (e.g., a voltage, a current, etc.) to a human-readable format (e.g., a string, a floating-point number, an integer, etc.). In some examples, the sensor interface circuitry 602 is instantiated by processor circuitry executing sensor interface instructions and/or configured to perform operations such as those represented by the flowcharts of FIGS. 7 and 8.

The model data set filterer circuitry 604 filters model data set(s) based on environmental data. For example, the model data set filterer circuitry 604 can use the environmental data received by the sensor interface circuitry 602 to identify a subset of model data sets within the simulation database 614 that were simulated with environmental conditions substantially the same accessed environmental data. In some examples, the model data set filterer circuitry 604 can select a subset of model data sets with approximately the same humidity as the accessed humidity data, an approximately the same temperature as the accessed temperature data, and/or a wind condition approximately the same as the accessed wind speed. In other examples, the model data set filterer circuitry 604 can select any other subset of environmental conditions. In some examples, the model data set filterer circuitry 604 can be absent. In some such examples, the data comparator circuitry 606 can compare the received hydrogen concentration data to each model data set of the simulation database. In some examples, the model data set filterer circuitry 604 is instantiated by processor circuitry executing model data set filter instructions and/or configured to perform operations such as those represented by the flowchart of FIG. 7.

The data comparator circuitry 606 compares the hydrogen concentration data accessed by the sensor interface circuitry 602 to the simulated hydrogen concentration associated with each of the model data sets identified by the model data set filterer circuitry 604 to determine a similarity between the received hydrogen concentration data and the simulated hydrogen concentration data. In some examples, the similarity between the hydrogen concentration data can be measured by any suitable statistical method including an average Euclidean distance between corresponding hydrogen concentrations, cross-correlation, serial correlation, similarity analysis, etc. In some examples, if the data comparator circuitry 606 can compare this determined similarity to a similarity threshold. In other examples, the data comparator circuitry 606 can determine the similarity between the received hydrogen concentration data to the model data set by any other statistical analysis and/or by selecting the most similar simulated hydrogen concentration data. In some examples, the data comparator circuitry 606 can be implemented (e.g., fully implemented, partially implemented, etc.) by a machine-learning model and/or artificial intelligence model that can incorporate previous leak identifications conducted by the leak management circuitry 102 to identify the most similar simulated hydrogen concentrations, identify false alarms (e.g., the hydrogen storage system 100 is not experiencing a leak, etc.), etc. In such examples, the model can be trained on prior true and false leak identifications and deployed as the data comparator circuitry 606 to identify a leak. The model can be retrained periodically and/or otherwise as new leak identifications are made, for example. For example, prior true and false leak identifications can be used in a supervised learning schema.

In other examples, the model can be trained via an unsupervised learning schema. In such examples, after the model has been trained, the model can be redeployed and used by the data comparator 606. In some examples, the data comparator circuitry 606 is instantiated by processor circuitry executing data comparator instructions and/or configured to perform operations such as those represented by the flowchart of FIG. 7.

The leak identifier circuitry 608 identifies the location of the leak and quantifies the leak based on the selected instance of the model data. For example, the leak identifier circuitry 608 can identify the location of the source of the leak based on the location of the simulated hydrogen leak in the model data set identified by the data comparator circuitry 606. Similarly, in some examples, the leak identifier circuitry 608 can quantify the identified leak based on the flow rate of the simulated hydrogen leak in the model data set. Additionally or alternatively, the leak identifier circuitry 608 can identify the location and/or the flow rate (e.g., a mass flow rate, a volume flow rate, etc.) of the leak by any other suitable means (e.g., an analysis of the received hydrogen concentration data, etc.). For example, the leak identifier circuitry 608 can spatially integrate the received hydrogen concentration data to quantify the identified leak.

Additionally or alternatively, the leak identifier circuitry 608 can quantify a leak via spatial integration. For example, the leak identifier circuitry 608 can determine the geometry of the flow path from hydrogen storage system based on adjacent features and sensor configuration. For example, the leak identifier 608 can determine the geometry of a boundary surface of the hydrogen storage system 100 based on adjacent features and the sensor configuration. For example, if the hydrogen concentration sensors of the hydrogen storage system 100 are arranged in a rectangle around the hydrogen storage system 100, the leak identifier circuitry 608 can identify the boundary condition as the surface of the rectangular prism defined by the hydrogen concentration (e.g., excluding the ground, etc.). Similarly, if f the hydrogen concentration sensors of the hydrogen storage system 100 are arranged in a dome around the hydrogen storage system 100, the leak identifier circuitry 608 can identify the boundary condition as the surface of the top surface of the dome defined by the hydrogen concentration (e.g., excluding the ground, etc.). In some examples, if the hydrogen storage system 100 is an enclosed spaced (e.g., in a warehouse, in an aircraft, etc.), the boundary surface of the hydrogen storage system 100 can be based on the openings between the enclosed spaced and the ambient environment (e.g., the doors and vents of a warehouse, etc.). In some examples, ambient features (e.g., walls, industrial equipment, etc.) can similarly reduce the boundary surface from which the leaked hydrogen can flow from the hydrogen storage system 100. In some such examples, the leak identifier circuitry 608 quantifies the leak by calculating the hydrogen flow out of the hydrogen storage system 100. For example, the leak identifier circuitry 608 can estimate a distribution of hydrogen concentration over the boundary surface using the received hydrogen concentration data and calculate an integral of the distribution over the boundary condition. In some examples, the leak identifier circuitry 608 is instantiated by processor circuitry executing leak identifier instructions and/or configured to perform operations such as those represented by the flowcharts of FIGS. 7 and 8.

The leak mitigation circuitry 610 determines the mitigation actions to be taken after the leak has been located and quantified. Mitigation actions can include isolating the leak (e.g., isolating a component or volume from which the leak is incurring from other components and/or volumes, etc.), disabling a pump, closing a valve, opening one or more ventilation pathways, increasing ventilation flow, etc. The leak mitigation circuitry 610 can determine if it is possible to isolate the leak based on the leak identified by the leak identifier circuitry 608 and then isolate the leak. For example, the leak mitigation circuitry 610 can determine if the leak can be isolated based on the location of the source of the leak identified. In some such examples, the leak mitigation circuitry 610 can determine the ability to isolate the leak based on the availability of alternative routes to route the hydrogen through. In some such examples, the leak mitigation circuitry 610 can interface with one or more components of the hydrogen storage system 100 to prevent hydrogen from flowing through the part of the hydrogen storage system 100 with the identified leak. In some examples, the leak mitigation circuitry 610 can disable a pump (e.g., one of the pumps 106A, 106B, etc.) and/or close a valve upstream of the leak location. For example, if a leak is identified at the fourth potential leak location 208, the leak mitigation circuitry 610 can isolate the leak (e.g., by routing hydrogen flowing from the hydrogen tank 104 through the pipe defined by the potential leak locations 202, 206, by routing hydrogen entirely through the second pump 106B, etc.). In other examples, the leak mitigation circuitry 610 can isolate the leak by any other suitable means. In other examples, if the leak mitigation circuitry 610 determines the leak can be isolated, the leak mitigation circuitry 610 can disable the hydrogen storage system. For example, the leak mitigation circuitry 610 can send a signal to turn off all power components of the hydrogen storage system 100 (e.g., the pumps 106A, 106B, the heat exchangers 108A, 108B, the vaporizer 110, etc.), close all valves of the hydrogen storage system 100, or modify any other suitable controllable feature of the hydrogen storage system 100. In other examples, the leak mitigation circuitry 610 can disable the hydrogen storage system 100 in any other suitable manner. In some examples, the leak mitigation circuitry 610 is instantiated by processor circuitry executing leak management instructions and/or configured to perform operations such as those represented by the flowcharts of FIGS. 7 and 8.

The report generator circuitry 612 generates a report. For example, the report generator circuitry 612 can generate a report including the location of the identified leak, the quantification of the identified leak, and the mitigation actions taken by the leak mitigation circuitry 610. In some examples, the report generator circuitry 612 can, via the sensor interface circuitry 602, include current hydrogen concentration data (e.g., taken after the mitigation actions by the hydrogen concentration sensors 402-448, etc.) in the generated report (e.g., to allow operators of the hydrogen storage system 100 to determine if it is safe to have a technician service the leak location, etc.). In other examples, the report generator circuitry 612 can include any other suitable information in the generated report. In some examples, the report generator circuitry 612 can generate one or more report(s) when the leak is initially sensed and/or after the location and/or mass flow rate of the leak is determined. In some such examples, an operator of the hydrogen storage system 100 and/or the leak management circuitry 102 can determine the mitigation action to be taken (e.g., via the leak mitigation circuitry 610, etc.) based on the generated report. In some examples, the report generator circuitry 612 is instantiated by processor circuitry executing report generator instructions and/or configured to perform operations such as those represented by the flowcharts of FIGS. 7 and 8.

In the illustrated example of FIG. 6, the leak management circuitry 102 includes the model data set management circuitry 600, which includes the simulation database 614, the parameter selector circuitry 616, and the leak simulator circuitry 618. In other examples, components of the model data set management circuitry 600 (e.g., the parameter selector circuitry 616, the leak simulator circuitry 618, etc.) can be implemented by different processor circuitry than the other components of the leak management circuitry 102. In some such examples, due to the computational burden of fluid dynamic simulations, the parameter selector circuitry 616 and the leak simulator circuitry 618 can be implemented via high-performance processor circuitry (e.g., a supercomputer, etc.).

The simulation database 614 stores the leak simulation model data 320 of FIG. 3. For example, the simulation database 614 can include instances of different leak scenarios (e.g., different leak locations with different leak severities and environmental conditions, etc.). In some examples, the simulation database 614 can be implemented by a hard disk drive, a solid-state drive, a cloud service, a random-access memory, and/or any other suitable memory.

The parameter selector circuitry 616 selects different parameters for the leak simulator circuitry 618 to use to simulate a leak (e.g., the simulated hydrogen leak 500 of FIG. 5. For example, the parameter selector circuitry 616 can select a leak location of the potential leak locations 202-246 and a quantity of the leak (e.g., a flow rate of hydrogen through the simulated hydrogen leak 500, etc.). In some examples, the parameter selector circuitry 616 can select the ambient conditions of the leak (e.g., wind speed, wind direction, humidity, temperature, etc.). In some examples, the parameter selector circuitry 616 is instantiated by processor circuitry executing parameter selector instructions and/or configured to perform operations such as those represented by the flowchart of FIG. 13.

The leak simulator circuitry 618 simulates the leak (e.g., the simulated hydrogen leak 500, etc.) based on the parameters selected by the parameter selector circuitry 616. For example, the leak simulator circuitry 618 can use computational fluid dynamics to simulate the simulated hydrogen leak with the selected parameters. In some examples, the leak simulator circuitry 618 can note the hydrogen concentration (e.g., an absolute hydrogen concentration, a difference between a measured hydrogen concentration and a nominal hydrogen concentration (e.g., ~10,000 ppm, etc.), etc.) associated with the leak (e.g., the steady state hydrogen concentration data, one or more transient hydrogen concentration data, etc.). In other examples, the leak simulator circuitry 618 can be used any other suitable means to simulate the leak with the selected parameters. In some examples, after simulating the leak, the leak simulator circuitry 618 can store the selected parameters and the hydrogen concentration data generated by the leak simulator circuitry 618 in the simulation database 614. In some examples, the leak simulator circuitry 618 is instantiated by processor circuitry executing leak simulator instructions and/or configured to perform operations such as those represented by the flowchart of FIG. 13.

In some examples, the leak management circuitry 102 includes means for interfacing with a sensor. For example, the means for interfacing with a sensor may be implemented by sensor interface circuitry 602. In some examples, the sensor interface circuitry 602 may be instantiated by processor circuitry such as the example processor circuitry 1512 of FIG. 15. For instance, the sensor interface circuitry 602 may be instantiated by the example microprocessor 1700 of FIG. 17 executing machine executable instructions such as those implemented by at least blocks 702, 704, 705 of FIG. 7 and/or the blocks 802, 804, 806 of FIG. 8. In some examples, the sensor interface circuitry 602 may be instantiated by hardware logic circuitry, which may be implemented by an ASIC, XPU, or the FPGA circuitry 1800 of FIG. 18 structured to perform operations corresponding to the machine readable instructions. Additionally or alternatively, the sensor interface circuitry 602 may be instantiated by any other combination of hardware, software, and/or firmware. For example, the sensor interface circuitry 602 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the leak management circuitry 102 includes means for filtering model data sets. For example, the means for filtering model data sets may be implemented by the model data set filterer circuitry 604. In some examples, the model data set filterer circuitry 604 may be instantiated by processor circuitry such as the example processor circuitry 1512 of FIG. 15. For instance, the model data set filterer circuitry 604 may be instantiated by the example microprocessor 1700 of FIG. 17 executing machine executable instructions such as those implemented by at least blocks 706, 708 of FIG. 7. In some examples, the model data set filterer circuitry 604 may be instantiated by hardware logic circuitry, which may be implemented by an ASIC, XPU, or the FPGA circuitry 1800 of FIG. 18 structured to perform operations corresponding to the machine readable instructions. Additionally or alternatively, the model data set filterer circuitry 604 may be instantiated by any other combination of hardware, software, and/or firmware. For example, the model data set filterer circuitry 604 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the leak management circuitry 102 includes means for comparing data. For example, the means for comparing data may be implemented by the data comparator circuitry 606. In some examples, the data comparator circuitry 606 may be instantiated by processor circuitry such as the example processor circuitry 1512 of FIG. 15. For instance, the data comparator circuitry 606 may be instantiated by the example microprocessor 1700 of FIG. 17 executing machine executable instructions such as those implemented by at least block 710 of FIG. 7. In some examples, the data comparator circuitry 606 may be instantiated by hardware logic circuitry, which may be implemented by an ASIC, XPU, or the FPGA circuitry 1800 of FIG. 18 structured to perform operations corresponding to the machine readable instructions. Additionally or alternatively, the data comparator circuitry 606 may be instantiated by any other combination of hardware, software, and/or firmware. For example, the data comparator circuitry 606 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the leak management circuitry 102 includes means for identifying a leak. For example, the means for identifying a leak may be implemented by the leak identifier circuitry 608. In some examples, the leak identifier circuitry 608 may be instantiated by processor circuitry such as the example processor circuitry 1512 of FIG. 15. For instance, the leak identifier circuitry 608 may be instantiated by the example microprocessor 1700 of FIG. 17 executing machine executable instructions such as those implemented by at least blocks 712, 714 of FIG. 7 and/or blocks 808, 810 of FIG. 8. In some examples, the leak identifier circuitry 608 may be instantiated by hardware logic circuitry, which may be implemented by an ASIC, XPU, or the FPGA circuitry 1800 of FIG. 18 structured to perform operations corresponding to the machine readable instructions. Additionally or alternatively, the leak identifier circuitry 608 be instantiated by any other combination of hardware, software, and/or firmware. For example, the leak identifier circuitry 608 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the leak management circuitry 102 includes means for mitigating a leak. For example, the means for mitigating a leak may be implemented by the leak mitigation circuitry 610. In some examples, the leak mitigation circuitry 610 may be instantiated by processor circuitry such as the example processor circuitry 1512 of FIG. 15. For instance, the leak mitigation circuitry 610 may be instantiated by the example microprocessor 1700 of FIG. 17 executing machine executable instructions such as those implemented by at least blocks 716, 718, 720 of FIG. 7 and/or block 812 of FIG. 8. In some examples, the leak mitigation circuitry 610 be instantiated by hardware logic circuitry, which may be implemented by an ASIC, XPU, or the FPGA circuitry 1800 of FIG. 18 structured to perform operations corresponding to the machine readable instructions. Additionally or alternatively, the leak mitigation circuitry 610 be instantiated by any other combination of hardware, software, and/or firmware. For example, the leak mitigation circuitry 610 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the leak management circuitry 102 includes means for generating a report. For example, the means for generating a report may be implemented by the report generator circuitry 612. In some examples, the report generator circuitry 612 may be instantiated by processor circuitry such as the example processor circuitry 1512 of FIG. 15. For instance, the report generator circuitry 612 may be instantiated by the example microprocessor 1700 of FIG. 17 executing machine executable instructions such as those implemented by at least block 720 of FIG. 7 and/or block 814 of FIG. 8. In some examples, the report generator circuitry 612 be instantiated by hardware logic circuitry, which may be implemented by an ASIC, XPU, or the FPGA circuitry 1800 of FIG. 18 structured to perform operations corresponding to the machine readable instructions. Additionally or alternatively, the report generator circuitry 612 be instantiated by any other combination of hardware, software, and/or firmware. For example, the report generator circuitry 612 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the leak management circuitry 102 includes means for selecting a parameter. For example, the means for selecting a parameter may be implemented by the parameter selector circuitry 616. In some examples, the parameter selector circuitry 616 may be instantiated by processor circuitry such as the example processor circuitry 1512 of FIG. 15. For instance, the parameter selector circuitry 616 may be instantiated by the example microprocessor 1700 of FIG. 17 executing machine executable instructions such as those implemented by at least blocks 1302, 1304, 1306, 1314 of FIG. 14. In some examples, the parameter selector circuitry 616 be instantiated by hardware logic circuitry, which may be implemented by an ASIC, XPU, or the FPGA circuitry 1800 of FIG. 18 structured to perform operations corresponding to the machine readable instructions. Additionally or alternatively, the parameter selector circuitry 616 be instantiated by any other combination of hardware, software, and/or firmware. For example, the parameter selector circuitry 616 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the leak management circuitry 102 includes means for simulating a hydrogen leak. For example, the means for simulating a hydrogen leak may be implemented by the leak simulator circuitry 618. In some examples, the leak simulator circuitry 618 may be instantiated by processor circuitry such as the example processor circuitry 1512 of FIG. 15. For instance, the leak simulator circuitry 618 may be instantiated by the example microprocessor 1700 of FIG. 17 executing machine executable instructions such as those implemented by at least blocks 1308, 1310, 1312 of FIG. 14. In some examples, the leak simulator circuitry 618 be instantiated by hardware logic circuitry, which may be implemented by an ASIC, XPU, or the FPGA circuitry 1800 of FIG. 18 structured to perform operations corresponding to the machine readable instructions. Additionally or alternatively, the leak simulator circuitry 618 be instantiated by any other combination of hardware, software, and/or firmware. For example, the leak simulator circuitry 618 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

While an example implementation of the leak management circuitry 102 of FIGS. 1A and 1B is illustrated in FIG. 6, one or more of the elements, processes, and/or devices illustrated in FIG. 6 may be combined, divided, re-arranged, omitted, eliminated, and/or implemented in any other way. Further, the example sensor interface circuitry 602, the model data set filterer circuitry 604, the data comparator circuitry 606, the leak identifier circuitry 608, the leak mitigation circuitry 610, the report generator circuitry 612, the simulation database 614, the parameter selector circuitry 616, the leak simulator circuitry 618, and/or, more generally, the example leak management circuitry 102 of FIGS. 1A and 1B, may be implemented by hardware alone or by hardware in combination with software and/or firmware. Thus, for example, any of the example sensor interface circuitry 602, the model data set filterer circuitry 604, the data comparator circuitry 606, the leak identifier circuitry 608, the leak mitigation circuitry 610, the report generator circuitry 612, the simulation database 614, the parameter selector circuitry 616, the leak simulator circuitry 618, and/or, more generally, the example leak management circuitry 102, could be implemented by processor circuitry, analog circuit(s), digital circuit(s), logic circuit(s), programmable processor(s), programmable microcontroller(s), graphics processing unit(s) (GPU(s)), digital signal processor(s) (DSP(s)), application specific integrated circuit(s) (ASIC(s)), programmable logic device(s) (PLD(s)), and/or field programmable logic device (s) (FPLD(s)) such as Field Programmable Gate Arrays (FPGAs). Further still, the example leak management circuitry 102 of FIGS. 1A and 1B may include one or more elements, processes, and/or devices in addition to, or instead of, those illustrated in FIG. 6, and/or may include more than one of any or all of the illustrated elements, processes and devices.

Figure 7:
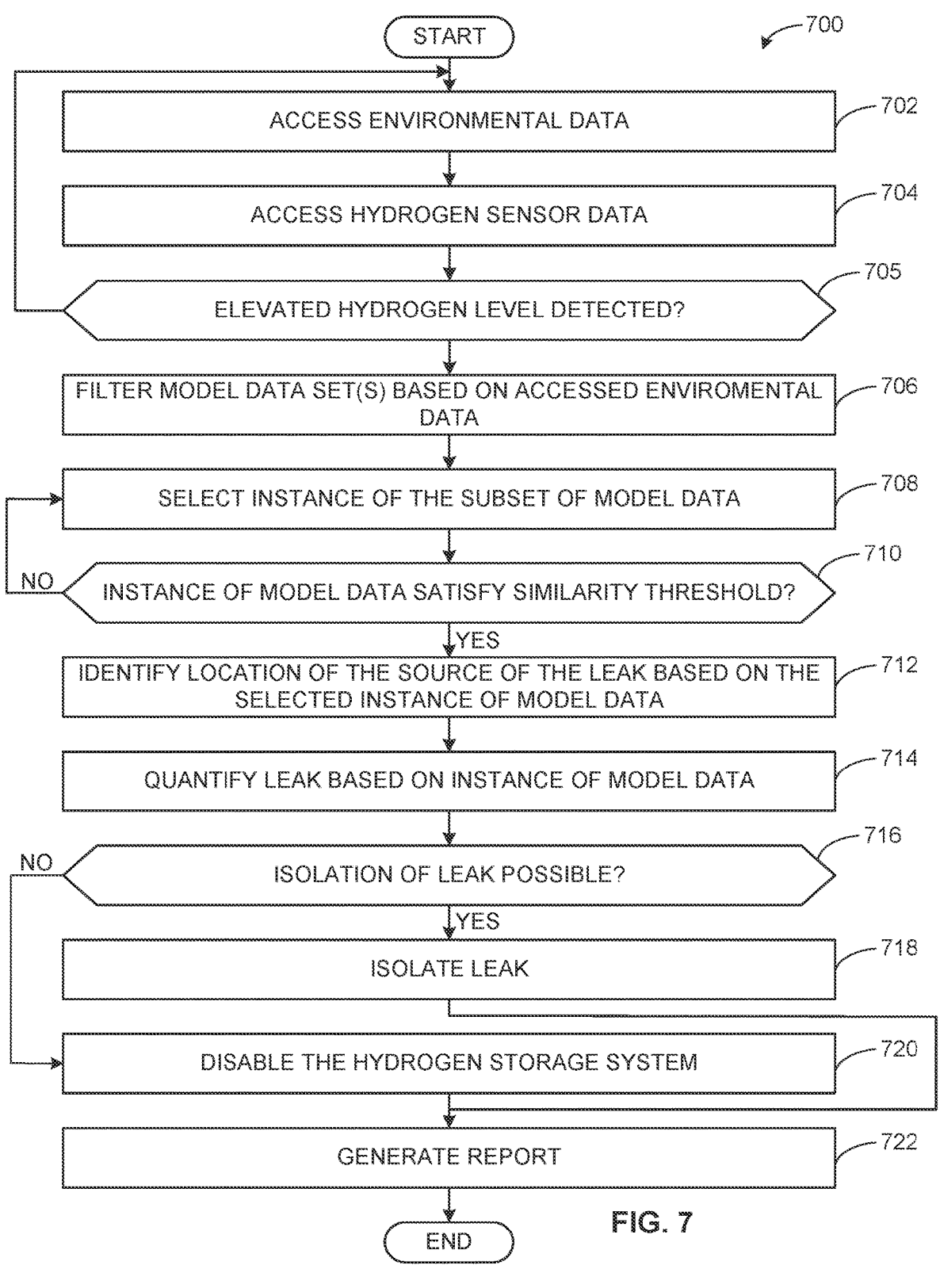
FIGS. 7 and 8 are flowcharts representative of example machine readable instructions and/or example operations that may be executed by example processor circuitry to implement the leak management system of FIG. 6.
Figure 8:
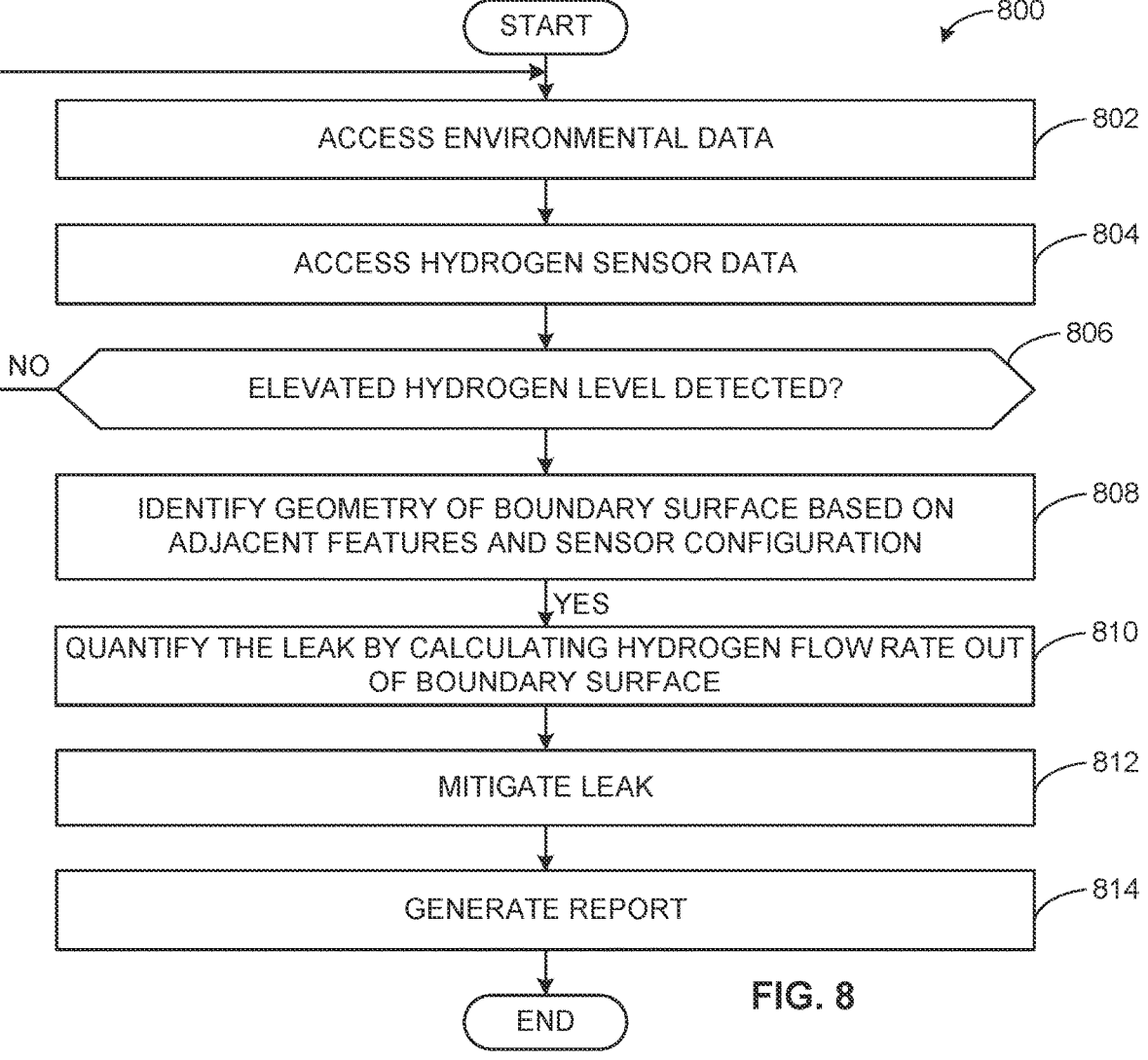

Flowcharts representative of example machine readable instructions, which may be executed to configure processor circuitry to implement the leak management circuitry 102 of FIG. 6, are shown in FIGS. 7 and 8. The machine readable instructions may be one or more executable programs or portion(s) of an executable program for execution by processor circuitry, such as the processor circuitry 1512 shown in the example processor platform 1500 discussed below in connection with FIG. 15 and/or the example processor circuitry discussed below in connection with FIGS. 16 and/or 17. The program may be embodied in software stored on one or more non-transitory computer readable storage media such as a compact disk (CD), a floppy disk, a hard disk drive (HDD), a solid-state drive (SSD), a digital versatile disk (DVD), a Blu-ray disk, a volatile memory (e.g., Random Access Memory (RAM) of any type, etc.), or a non-volatile memory (e.g., electrically erasable programmable read-only memory (EEPROM), FLASH memory, an HDD, an SSD, etc.) associated with processor circuitry located in one or more hardware devices, but the entire program and/or parts thereof could alternatively be executed by one or more hardware devices other than the processor circuitry and/or embodied in firmware or dedicated hardware. The machine readable instructions may be distributed across multiple hardware devices and/or executed by two or more hardware devices (e.g., a server and a client hardware device). For example, the client hardware device may be implemented by an endpoint client hardware device (e.g., a hardware device associated with a user) or an intermediate client hardware device (e.g., a radio access network (RAN)) gateway that may facilitate communication between a server and an endpoint client hardware device). Similarly, the non-transitory computer readable storage media may include one or more mediums located in one or more hardware devices. Further, although the example program is described with reference to the flowcharts illustrated in FIGS. 7 and 8, many other methods of implementing the example leak management circuitry 102 may alternatively be used. For example, the order of execution of the blocks may be changed, and/or some of the blocks described may be changed, eliminated, or combined. Additionally or alternatively, any or all of the blocks may be implemented by one or more hardware circuits (e.g., processor circuitry, discrete and/or integrated analog and/or digital circuitry, an FPGA, an ASIC, a comparator, an operational-amplifier (op-amp), a logic circuit, etc.) structured to perform the corresponding operation without executing software or firmware. The processor circuitry may be distributed in different network locations and/or local to one or more hardware devices (e.g., a single-core processor (e.g., a single core central processor unit (CPU)), a multi-core processor (e.g., a multi-core CPU, an XPU, etc.) in a single machine, multiple processors distributed across multiple servers of a server rack, multiple processors distributed across one or more server racks, a CPU and/or a FPGA located in the same package (e.g., the same integrated circuit (IC) package or in two or more separate housings, etc.).

The machine readable instructions described herein may be stored in one or more of a compressed format, an encrypted format, a fragmented format, a compiled format, an executable format, a packaged format, etc. Machine readable instructions as described herein may be stored as data or a data structure (e.g., as portions of instructions, code, representations of code, etc.) that may be utilized to create, manufacture, and/or produce machine executable instructions. For example, the machine readable instructions may be fragmented and stored on one or more storage devices and/or computing devices (e.g., servers) located at the same or different locations of a network or collection of networks (e.g., in the cloud, in edge devices, etc.). The machine readable instructions may require one or more of installation, modification, adaptation, updating, combining, supplementing, configuring, decryption, decompression, unpacking, distribution, reassignment, compilation, etc., in order to make them directly readable, interpretable, and/or executable by a computing device and/or other machine. For example, the machine readable instructions may be stored in multiple parts, which are individually compressed, encrypted, and/or stored on separate computing devices, wherein the parts when decrypted, decompressed, and/or combined form a set of machine executable instructions that implement one or more operations that may together form a program such as that described herein.

In another example, the machine readable instructions may be stored in a state in which they may be read by processor circuitry, but require addition of a library (e.g., a dynamic link library (DLL)), a software development kit (SDK), an application programming interface (API), etc., in order to execute the machine readable instructions on a particular computing device or other device. In another example, the machine readable instructions may need to be configured (e.g., settings stored, data input, network addresses recorded, etc.) before the machine readable instructions and/or the corresponding program(s) can be executed in whole or in part. Thus, machine readable media, as used herein, may include machine readable instructions and/or program(s) regardless of the particular format or state of the machine readable instructions and/or program(s) when stored or otherwise at rest or in transit.

The machine readable instructions described herein can be represented by any past, present, or future instruction language, scripting language, programming language, etc. For example, the machine readable instructions may be represented using any of the following languages: C, C++, Java, C#, Perl, Python, JavaScript, HyperText Markup Language (HTML), Structured Query Language (SQL), Swift, etc.

FIG. 7 is a flowchart representative of example machine readable instructions and/or example operations 700 that may be executed and/or instantiated by processor circuitry to quantify a leak and identify the location of the leak in the hydrogen storage system 100. The machine readable instructions and/or the operations 700 of FIG. 7 begin at block 702, at which the sensor interface circuitry 602 accesses environmental data. For example, the sensor interface circuitry 602 can access sensor data from the environmental sensors of the hydrogen storage system 100. For example, the sensor interface circuitry 602 can receive sensor data from the sensors 450, 452, 454 of the hydrogen storage system 100 of FIGS. 4A and 4B. Additionally or alternatively, the sensor interface circuitry 602 can interface with one or more external sensors (e.g., other sensors at the facility housing the hydrogen storage system 100 and/or a weather service to determine the environmental data. In some examples, the sensor interface circuitry 602 can transform the received environmental sensor data from a machine-readable format (e.g., a voltage, a current, etc.) to a human-readable format (e.g., a string, a floating-point number, an integer, etc.).

At block 704, the sensor interface circuitry 602 accesses hydrogen sensor data. For example, the sensor interface circuitry 602 can receive sensor data from the hydrogen concentration sensors 402, 404, 406, 408, 410, 412, 414, 416, 418, 420, 422, 424, 426, 428, 430, 432, 434, 436, 438, 440, 444, 446, 448 of the hydrogen storage system 100 of FIGS. 4A and 4B. In some examples, the sensor interface circuitry 602 can format the received sensor data into a data structure (e.g., a matrix, a vector, etc.) and/or fit a curve (e.g., a function, etc.) to the received sensor data. The sensor interface circuitry 602 can transform the received hydrogen concentration sensor data from a machine-readable format (e.g., a voltage, a current, etc.) to a human-readable format (e.g., a string, a floating-point number, an integer, etc.).

At block 705, the sensor interface circuitry 602 determines if an elevated hydrogen concentration data is detected. For example, the sensor interface circuitry 602 can determine if one or more of the hydrogen sensors 402-448 are outputting an above-nominal hydrogen concentration output. If the sensor interface circuitry 602 detects an elevated hydrogen concentration level, the operations 700 advance to block 706. For example, if the first hydrogen concentration sensor 402 of FIG. 4A or 4B outputs a hydrogen concentration that is above a nominal hydrogen level (e.g., an expected concentration in the ambient atmosphere, an expected concentration in the ambient environment, etc.), the sensor interface circuitry 602 can determine there is an elevated hydrogen concentration in the hydrogen storage facility. If the sensor interface circuitry 602 does not detect an elevated hydrogen concentration level, the operations 700 return to block 702.

At block 706, the model data set filterer circuitry 604 filters model data sets based on environmental data. For example, the model data set filterer circuitry 604 can use the received environmental data to identify a subset of model data sets within the simulation database 614 that were simulated with environmental conditions substantially the same accessed environmental data. In some examples, the model data set filterer circuitry 604 can select a subset of model data sets with a substantially same humidity as the accessed humidity data, a substantially same temperature as the accessed temperature data, and/or a wind condition substantially the same wind speed as the accessed wind speed. In other examples, the model data set filterer circuitry 604 can select any other subset of environmental conditions. In some examples, the model data set filterer circuitry 604 can be absent. In some such examples, the received hydrogen concentration data can be compared to each model data set of the simulation database (e.g., the during the execution of blocks 708, 710, etc.).

At block 708, the model data set filterer circuitry 604 selects an instance of the subset of model data set(s). For example, the model data set filterer circuitry 604 can select one of the subset of model data set(s) of the simulation database 614 identified during the execution of block 706. In some examples, the model data set filterer circuitry 604 can select an instance that has not been previously selected during the execution of block 708.

At block 710, the data comparator circuitry 606 determines if the instance of model data satisfies a similarity threshold with hydrogen sensor data. For example, the data comparator circuitry 606 can compare the hydrogen concentration data received during the block 704 to the simulated hydrogen concentration associated with the model data set selected during the execution of block 708 to determine the similarity between the received hydrogen concentration data and the simulated hydrogen concentration data. In some examples, the similarity between the hydrogen concentration data and the simulated hydrogen concentration data can be measured by any suitable statistical method including an average Euclidean distance between corresponding hydrogen concentrations, cross-correlation, serial correlation, similarity analysis, etc. In some examples, if the data comparator circuitry 606 can compare this determined similarity to a similarity threshold. In some examples, the data comparator circuitry 606 can use machine-learning and/or artificial intelligence models to determine a similarity between the hydrogen concentration data and the simulated hydrogen concentration data. If the data comparator circuitry 606 determines the model data set satisfies the similarity threshold, the operations 700 advance to block 712. If the data comparator circuitry determines the model data set does not satisfy the similarity threshold, the operations 700 return to block 708.

Additionally or alternatively, the model data set filterer circuitry 604 and/or the data comparator circuitry 606 can repeatedly execute blocks 706 and 708 to determine the similarity of the measured hydrogen concentration data and each instance of the simulated hydrogen concentration data. In some such examples, the data comparator circuitry 606 can select the most similar instance of the simulated hydrogen concentration data for use with the execution of blocks 712-722.

At block 712, the leak identifier circuitry 608 identifies the location of the source of the leak based on the selected instance of the model data. For example, the leak identifier circuitry 608 can identify the location of the source of the leak based on the location of the simulated hydrogen leak in the model data set identified during the execution of block 710. At block 714, the leak identifier circuitry 608 determines quantifies the leak based on the selected instance of the model data. For example, the leak identifier circuitry 608 can identify the quantity of the leak based on the mass flow rate of the simulated hydrogen leak in the model data set identified during the execution of block 710.

At block 716, the leak mitigation circuitry 610 determines if the isolation of the leak is possible. For example, the leak mitigation circuitry 610 can determine if the leak can be isolated based on the location of the source of the leak identified during the execution of block 714. In some examples, the leak mitigation circuitry 610 can determine the ability to isolate the leak is based on the availability of alternative routes through which the hydrogen can be routed. For example, if a leak is identified at the fourth potential leak location 208, the leak mitigation circuitry 610 can determine the leak can be isolated (e.g., by routing hydrogen flowing from the hydrogen tank 104 through the pipe defined by the potential leak locations 202, 206, by routing hydrogen entirely through the second pump 106B, etc.). Similarly, if a leak is identified at the twentieth potential leak location 240, the leak mitigation circuitry 610 can determine that the leak cannot be isolated. In other examples, the leak mitigation circuitry 610 can determine if the leak can be isolated by any other suitable means. If the leak mitigation circuitry 610 determines the leak can be isolated, the operations 700 advance to block 718. If the leak mitigation circuitry 610 determines that the leak cannot be isolated, the operations 700 advance to block 720.

At block 718, the leak mitigation circuitry 610 isolates the leak. For example, the leak mitigation circuitry 610 can interface with one or more components of the hydrogen storage system 100 to prevent hydrogen from flowing through the part of the hydrogen storage system 100 with the identified leak. In some examples, the leak mitigation circuitry 610 can send a signal to disable a pump (e.g., one of the pumps 106A, 106B, etc.), close a valve upstream of the leak location, and/or any other suitable controllable feature(s) of the hydrogen storage system 100. For example, if a leak is identified at the fourth potential leak location 208, the leak mitigation circuitry 610 can isolate the leak (e.g., by routing hydrogen flowing from the hydrogen tank 104 through the pipe defined by the potential leak locations 202, 206, by routing hydrogen entirely through the second pump 106B, etc.). In other examples, the leak mitigation circuitry 610 can isolate the leak by any other suitable means. At block 720, the leak mitigation circuitry 610 disables the hydrogen storage system. For example, the leak mitigation circuitry 610 can send a signal to disable a pump (e.g., one of the pumps 106A, 106B, etc.), close a valve upstream of the leak location, and/or any other suitable controllable feature(s) of the hydrogen storage system 100. In other examples, the leak mitigation circuitry 610 can disable the hydrogen storage system 100 in any other suitable manner.

At block 722, the report generator circuitry 612 generates a report. For example, the report generator circuitry 612 can generate a report including the location of the identified leak, quantification of the identified leak, and the mitigation actions taken by the leak mitigation circuitry 610 during the execution of blocks 716, 718, 720. In some examples, the report generator circuitry 612 can, via the sensor interface circuitry 602, include current hydrogen concentration data (e.g., taken after the mitigation actions by the hydrogen concentration sensors 402, 404, 406, 408, 410, 412, 414, 416, 418, 420,422, 424, 426, 428, 430, 432, 434, 436, 438, 440, 442, 444, 446, 448, etc.) in the generated report (e.g., to allow operators of the hydrogen storage system 100 to determine if it is safe to have a technician service the leak location, etc.). In other examples, the report generator circuitry 612 can include any other suitable information in the generated report. The operations 700 then end.

FIG. 8 is a flowchart representative of example machine readable instructions and/or example operations 800 that may be executed and/or instantiated by processor circuitry to quantify a leak in the hydrogen storage system 100. The example operations 800 can be used in conjunction with the operations 700 to quantify the leak in alternative/addition to the execution of block 714. In other examples, the operations 800 can be used to independently to quantify a leak.

The machine readable instructions and/or the operations 800 of FIG. 8 begin at block 802, at which the sensor interface circuitry 602 accesses environmental data. For example, the sensor interface circuitry 602 can access sensor data from the environmental sensors of the hydrogen storage system 100. For example, the sensor interface circuitry 602 can receive sensor data from the sensors 450, 452, 454 of the hydrogen storage system 100 of FIGS. 4A and 4B. Additionally or alternatively, the sensor interface circuitry 602 can interface with one or more external sensors (e.g., other sensors at the facility housing the hydrogen storage system 100 and/or a weather service to determine the environmental data. In some examples, the sensor interface circuitry 602 can transform the received environmental sensor data from a machine-readable format (e.g., a voltage, a current, etc.) to a human-readable format (e.g., a string, a floating-point number, an integer, etc.).

At block 804, the sensor interface circuitry 602 accesses hydrogen sensor data. For example, the sensor interface circuitry 602 can receive sensor data from the hydrogen concentration sensors 402, 404, 406, 408, 410, 412, 414, 416, 418, 420, 422, 424, 426, 428, 430, 432, 434, 436, 438, 440, 444, 446, 448 of the hydrogen storage system 100 of FIGS. 4A and 4B. In some examples, the sensor interface circuitry 602 can format the received sensor data into a data structure (e.g., a matrix, a vector, etc.) and/or fit a curve (e.g., a function, etc.) to the received sensor data. The sensor interface circuitry 602 can transform the received hydrogen concentration sensor data from a machine-readable format (e.g., a voltage, a current, etc.) to a human-readable format (e.g., a string, a floating-point number, an integer, etc.).

At block 806, the sensor interface circuitry 602 determines if elevated hydrogen concentration data is detected. For example, the sensor interface circuitry 602 can determine if one or more of the hydrogen sensors 402-448 are outputting an above-nominal hydrogen concentration output. If the sensor interface circuitry 602 detects an elevated hydrogen concentration level, the operations 800 advance to block 808. If the sensor interface circuitry 602 does not detect an elevated hydrogen concentration level, the operations 800 return to block 802.

At block 808, the leak identifier circuitry 608 determines the geometry of the flow path from a hydrogen storage system based on adjacent features and sensor configuration. For example, the leak identifier 608 can determine the geometry of a boundary surface of the hydrogen storage system 100 based on adjacent features and the sensor configuration. For example, if the hydrogen concentration sensors of the hydrogen storage system 100 are arranged in a rectangle around the hydrogen storage system 100, the leak identifier circuitry 608 can identify the boundary condition as the surface of the rectangular prism defined by the hydrogen concentration (e.g., excluding the ground, etc.). Similarly, if f the hydrogen concentration sensors of the hydrogen storage system 100 are arranged in a dome around the hydrogen storage system 100, the leak identifier circuitry 608 can identify the boundary condition as the surface of the top surface of the dome defined by the hydrogen concentration (e.g., excluding the ground, etc.). In some examples, if the hydrogen storage system 100 is an enclosed spaced (e.g., in a warehouse, in an aircraft, etc.), the boundary surface of the hydrogen storage system 100 can be based on the openings between the enclosed spaced and the ambient environment (e.g., the doors and vents of a warehouse, etc.). In some examples, ambient features (e.g., walls, industrial equipment, etc.) can similarly reduce the boundary surface from which the leaked hydrogen can flow from the hydrogen storage system 100.

At block 810, the leak identifier circuitry 608 quantifies the leak by calculating the hydrogen flow out of the hydrogen storage system 100. For example, the leak identifier circuitry 608 can estimate a distribution of hydrogen concentration over the boundary surface using the received hydrogen concentration data and calculate an integral of the distribution over the boundary condition. In other examples, the leak identifier circuitry 608 can calculate hydrogen flow through the boundary surface by any other suitable mathematical calculations.

At block 812, the leak mitigation circuitry 610 determines the mitigation actions to be taken after the leak has been quantified. For example, the leak mitigation circuitry 610 can disable one or more pump(s) of the hydrogen storage system 100, can close one or more valve(s) of the hydrogen storage system 100, open one or more ventilation pathway (s) of the hydrogen storage system 100, and/or increase flow through a particular portion of the hydrogen storage system 100.

FIGS. 9-13 describe another leak detection process(es) that can be used with the hydrogen storage system 100. The example leak detection process described in conjunction with FIGS. 9-13 is similar to the leak detection processes of FIGS. 1A-8, except that it includes a mobile sensor platform that enables the exact location of the source of the leak to be identified. While the examples of FIGS. 9-13 are described with reference to the sensor configuration 400 of FIGS. 4A and 4B, it should be appreciated that the leak detection process of FIGS. 9-13 enables the hydrogen storage system to use substantially less static hydrogen sensors (e.g., the hydrogen concentration sensors 402-448, etc.) than the leak detection processes of FIGS. 1A-8. When the same element number is used in connection with FIGS. 9-13 as was used in FIG. 1A-8, it has the same meaning unless otherwise indicated.

Figure 9:
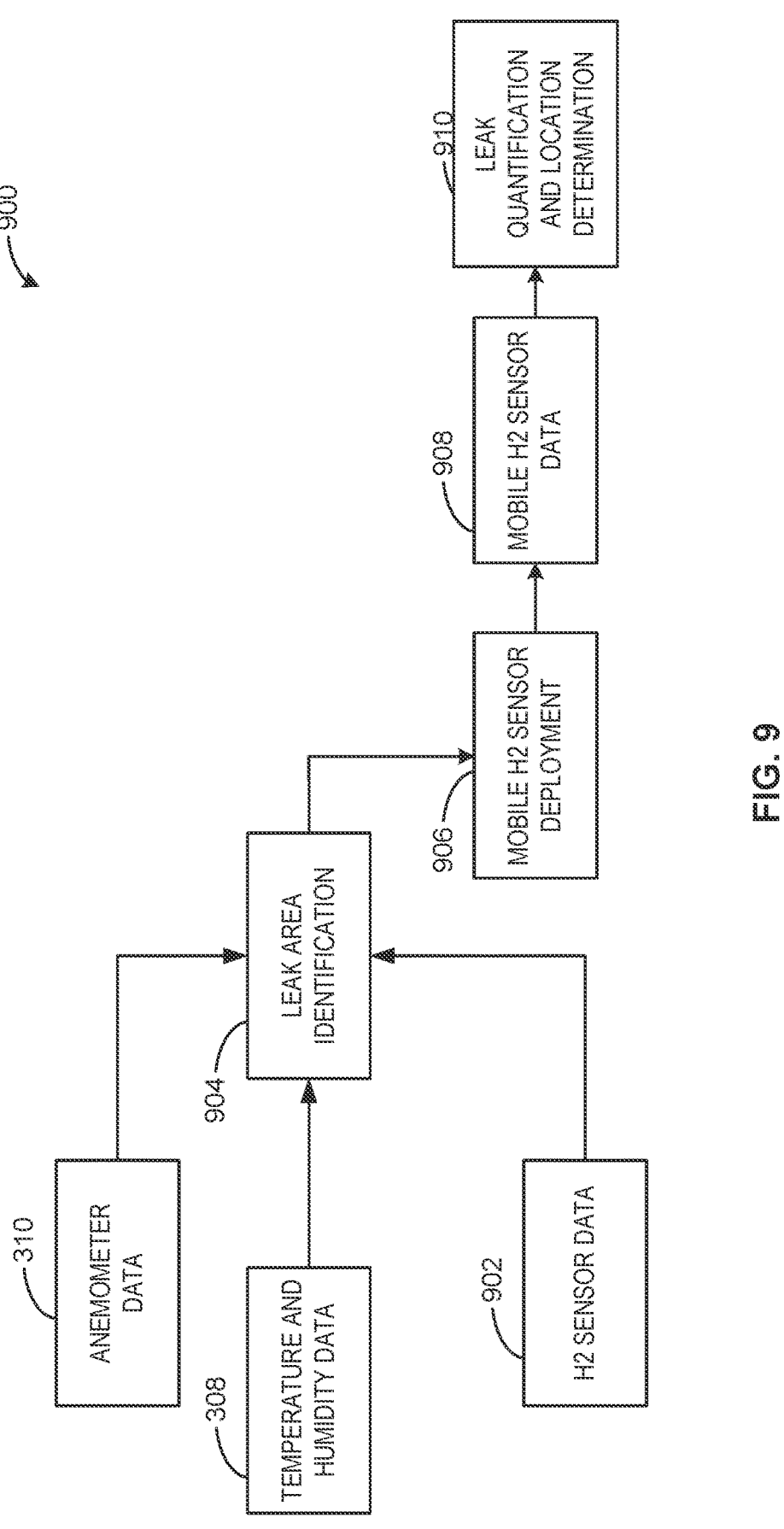
FIG. 9 is a process diagram of another leak detection process that can be used with the hydrogen storage system of FIGS. 1A-2.

FIG. 9 is a process diagram of another leak detection process 900 that can be used with the hydrogen storage system 100 of FIGS. 1A-2. In the illustrated example of FIG. 9, the example leak detection process 900 receives inputs of the example anemometer data 308 of FIG. 3, the example temperature and humidity data 310 of the FIG. 3, and example hydrogen presence data 902. In the illustrated example of FIG. 9, the example leak detection process 900 includes an example leak area identification subprocess 904. After conducting the data comparison subprocess 318, the leak detection process 300 includes an example mobile hydrogen sensor deployment subprocess 906, which generates example mobile hydrogen sensor data 908. In the illustrated example of FIG. 9, the example leak detection process 900 includes leak quantification and determination subprocess 910, which uses the mobile hydrogen sensor data 908.

The hydrogen presence data 902 is data indicative of the elevated presence and/or concentration of hydrogen at various locations in and around the hydrogen storage system 100. For example, the hydrogen presence data 902 can be a series of discrete values corresponding to the output of a plurality of hydrogen concentration sensors (e.g., a part per million (ppm) of hydrogen, a percentage of hydrogen in ambient air by mass, a percentage of hydrogen by volume, etc.). In some examples, the hydrogen presence data 902 can be arranged in a matrix, a vector, and/or any other suitable data structure. In other examples, the hydrogen concentration data 312 can be formatted as a function (e.g., a function that receives a location as an inputs and outputs a hydrogen concentration, etc.). Unlike the hydrogen concentration data 312 of FIG. 3, the hydrogen presence data 902 can be of a comparatively lower fidelity (e.g., less accurate, etc.), less densely collected (e.g., collected from a fewer amount of sensors, etc.) and/or binary (e.g., a binary output indicating a presence of elevated hydrogen concentration in the air, etc.). In other examples, the hydrogen presence data 902 can be of a same quality and density as the hydrogen concentration data 312 of FIG. 3.

The leak area identification subprocess 904 uses the collected hydrogen presence data 902 to determine a leak area. The leak area identified by the leak area identification subprocess 904 is a region (e.g., a volume, an area, etc.) of the hydrogen storage system 100 and can encompass a plurality of potential leak locations. In some examples, the leak area identification subprocess 904 can be implemented by the data comparison subprocess 318 of FIG. 3. In some such examples, the leak area identification subprocess 904 can filter the leak simulation model data (e.g., the leak simulation model data 320 of FIG. 3, etc.) based on the collected the anemometer data 308 and the temperature and humidity data 310. In other examples, the leak area identification subprocess 904 can identify likely areas in any suitable means. For example, the leak area identification subprocess 904 can utilize the sensors associated with the hydrogen presence data 902 and/or hydrogen spread inferences based on the collected anemometer data 308 and/or the temperature and humidity data 310.

The mobile hydrogen sensor deployment subprocess 906 deploys a mobile sensor platform to the leak area identified by the mobile hydrogen sensor data 908. For example, the mobile hydrogen sensor deployment subprocess 906 can deploy a drone, a wheel vehicle, a tracked vehicle, and/or a sensor platform coupled to one or more features of the hydrogen storage system 100. In some such examples, the sensor platform deployed by the mobile hydrogen sensor deployment subprocess 906 includes a plurality of sensors, including a hydrogen concentration sensor, which is used to generate the mobile hydrogen sensor data 908. The leak quantification and determination subprocess 910 identifies the location of the source of the leak based on the mobile hydrogen sensor data 908. For example, the mobile hydrogen sensor data 908 can include sensor data collected from directly adjacent to the potential leak locations in the area identified by the leak area identification subprocess 904. In some examples, if one of the potential leak locations represented in the mobile hydrogen sensor data 908 has elevated hydrogen concentration levels, the leak quantification and determination subprocess 910 can identify that potential leak location as the location of the source of the leak.

Figure 10A:
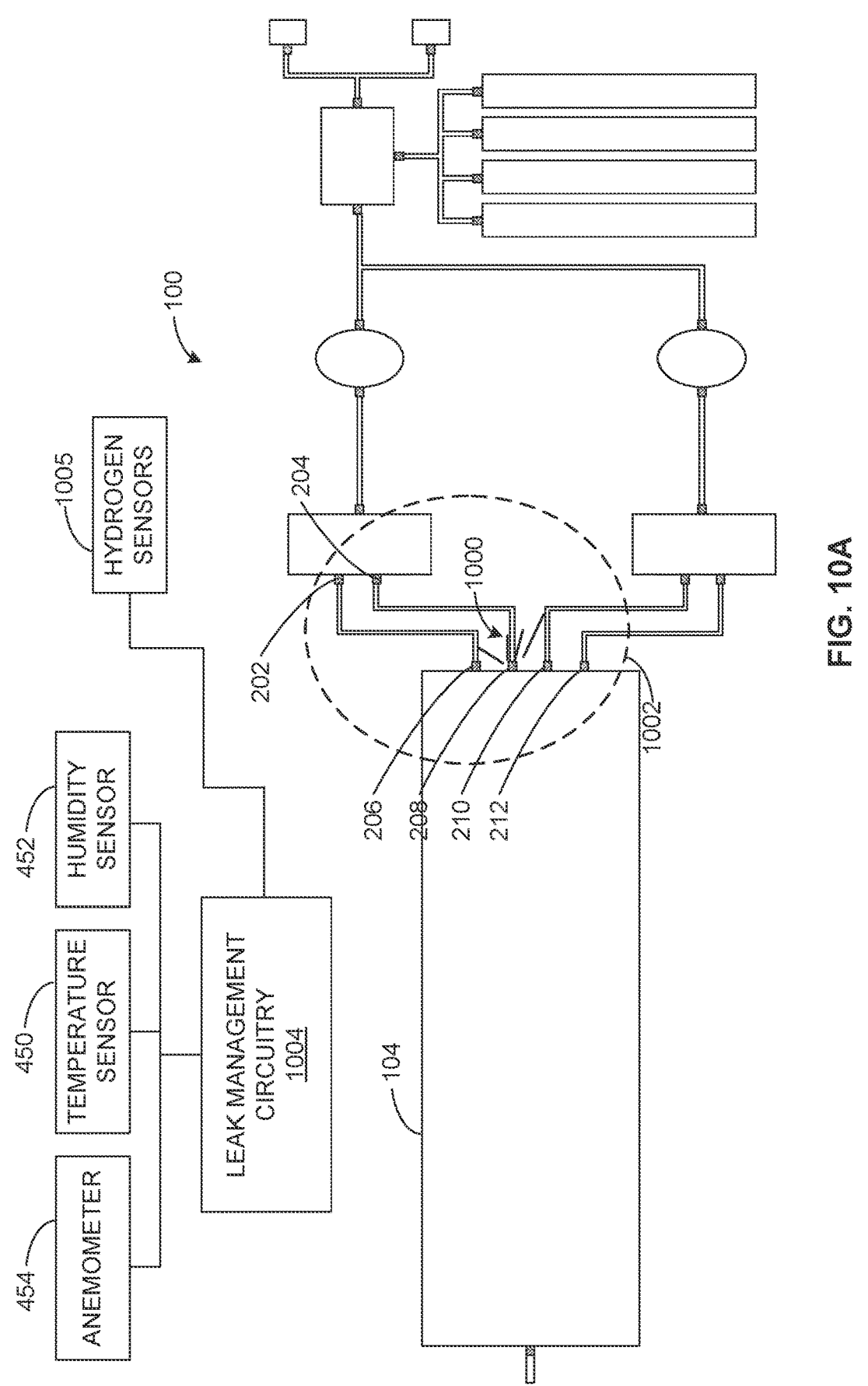
FIGS. 10A-10C depict an example implementation of the leak detection process of FIG. 9.

FIG. 10A depicts the example hydrogen storage system 100 of FIGS. 1A and 1B undergoing an example leak 1000 coming from the hydrogen tank 104 of FIGS. 1A and 1B. In the illustrated example of FIG. 10A, the hydrogen storage system 100 includes an example leak management circuitry 1004, which has identified example leak region 1002 as containing the example leak 1000 based on data from example hydrogen sensor(s) 1005, the temperature sensor 450 of FIG. 4B, the humidity sensor 452 of FIG. 4B, and the anemometer 454 of FIG. 4B. the illustrated example of FIG. 10A, the leak region 1002 includes the potential leak locations 202, 204, 206, 208, 210, 212 of FIG. 2.

In the illustrated example of FIG. 10A, the leak 1000 is present at the example fourth potential leak location 208. The leak management circuitry 1004 has identified the example leak region 1002 as containing the leak 1000. For example, the leak management circuitry 1004 can identify the leak region 1002 based on sensor data from the hydrogen sensor(s) 1005, the temperature sensor 450 the humidity sensor 452, and the anemometer 454. For example, the leak management circuitry 1004 can identify the leak region 1002 based on elevated hydrogen readings from the hydrogen sensor(s) 1005 contained within the leak region 1002 and/or ones of the hydrogen sensor(s) 1005 downwind of the leak region 1002. In other examples, the leak management circuitry 1004 can identify the leak region 1002 can identify the leak region 1002 in any other suitable method.

In some examples, like the system(s) of FIGS. 1A-8, some or all of the anemometer 454, the temperature sensor 450 and/or the humidity sensor 452 can be absent. In other such examples, the wind condition, ambient temperature and/or the ambient humidity can be determined by accessing such information from a weather service, using historic data indicative of such information, and/or by any other suitable means. Alternatively, the data associated with such sensors can be omitted from the determination made by the leak management circuitry 1004. In some such examples, the leak management circuitry 1004 can identify a comparatively larger potential leak area than the leak region 1002 to compensate for the greater uncertainty about the hydrogen distribution caused by the absent of such environmental data.

While the example leak region 1002 has been identified as an oval, the leak management circuitry 1004 can identify any suitable 2-dimensional or 3-dimensional shape as containing the leak 1000. In some examples, the shape and size of the leak region 1002 (e.g., the number of potential leak locations contained therein, etc.) identified by the leak management circuitry 1004 can be based on the number and fidelity of the hydrogen sensors of the hydrogen storage system 100, the ambient environment of the hydrogen storage system 100 (e.g., the temperature, the humidity, the wind speed, the wind direction, etc.). In some examples, instead of the identifying an example leak region 1002, the leak management circuitry 1004 can instead identify a list of the potential leak locations that may be the origin of the ongoing leak 1000. In some examples, the leak management circuitry 1004 can omit the determination of the leak region 1002. In some such examples, after detecting elevated hydrogen levels via the hydrogen sensor(s) 1005, the leak management circuitry 1004 can proceed with the deployment of the mobile hydrogen sensor platform to check each of the potential leak locations 202-246 of the hydrogen storage system 100.

Figure 10B:
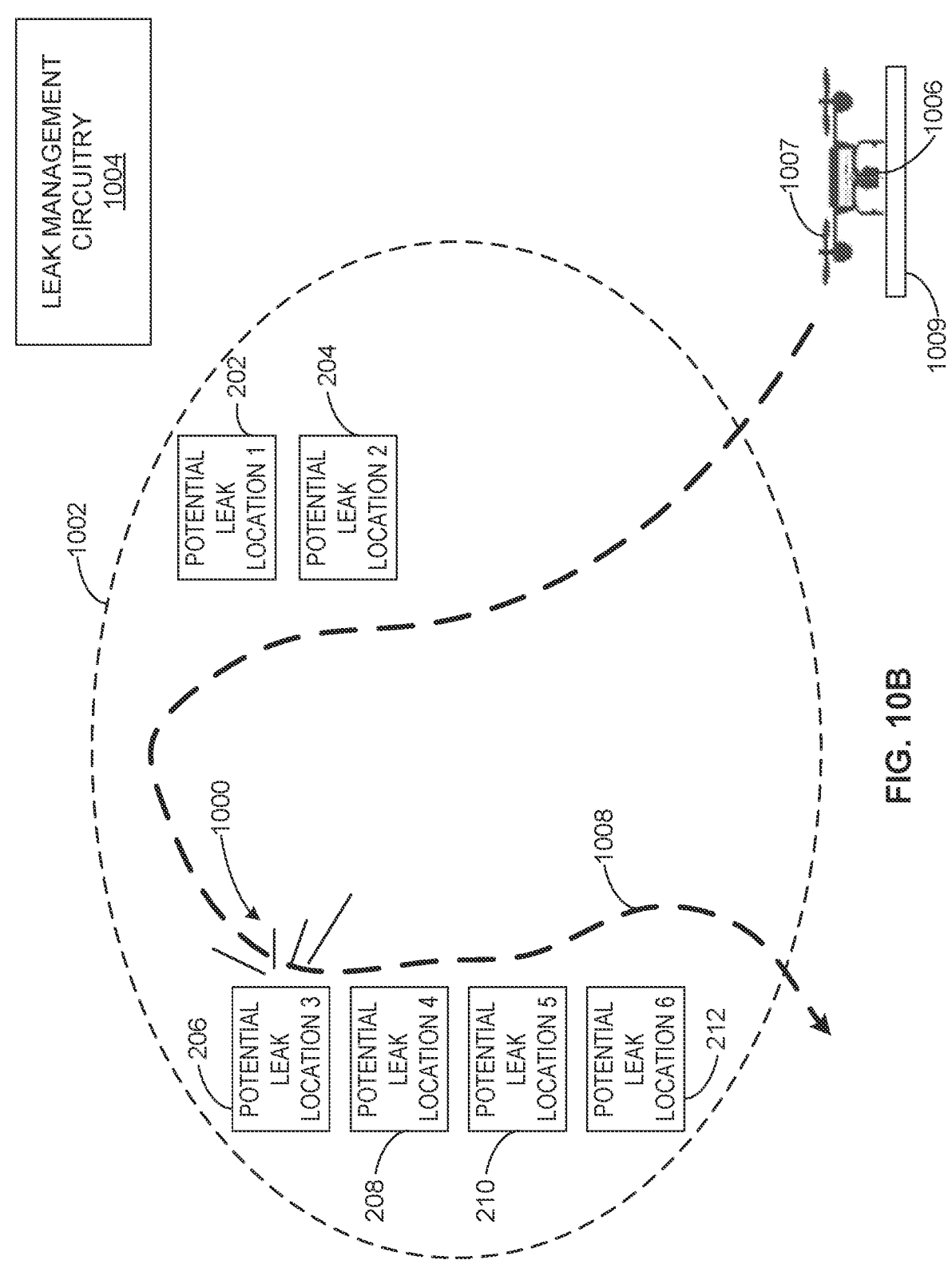

FIG. 10B is a simplified illustration of the leak 1000 and the leak region 1002 of FIG. 10A. In the illustrated example of FIG. 10B, the leak management circuitry 1004 has deployed an example mobile sensor platform 1006 to investigate the potential leak locations 202, 204, 206, 208, 210, 212 within the leak region 1002. In the illustrated example of FIG. 10B, the leak management circuitry 1004 has identified an example predetermined route 1008 for the mobile sensor platform 1006 to follow.

In the illustrated example of FIG. 10B, the mobile sensor platform 1006 is illustrated a flying drone including example mobile sensors 1007. For example, the mobile sensor platform 1006 can include a plurality of hydrogen sensors, an optical sensor (e.g., a photo camera, a video camera, etc.), a microphone, and/or any other suitable temperatures. The mobile sensor platform 1006 can use the mobile sensors 1007 to identify the source of the leak 1000. For example, the mobile sensor platform 1006 can identify the leak 1000 by detecting high concentrations of hydrogen using hydrogen concentration sensors, by detecting an opening and/or other physical feature that may be a leak using optical sensors, and/or by listening for a leak using a microphone. While only one mobile sensor platform 1006 is illustrated in FIGS. 10B and 10C, it should be appreciated that multiple mobile hydrogen sensor platforms can be used.

When not in use to identify the leak, the mobile sensor platform 1006 can be stored onsite at an example standby location 1009 or near the hydrogen storage system 100. For example, the mobile sensor platform 1006 can be connected to a charging station (e.g., a power outlet, etc.) at the standby location 1009 to permit a rapid response to identify leaks. Additionally or alternatively, the mobile sensor platform 1006 can be a component of the hydrogen storage system 100 (e.g., a vehicle mounted on tracks on the hydrogen storage system, a mobile sleeve mounted on the pipes of the hydrogen storage system 100, etc.). In other examples, the mobile sensor platform 1006 can be carried and/or stored by a technician and deployed after the leak management circuitry 1004.

Figure 10C:
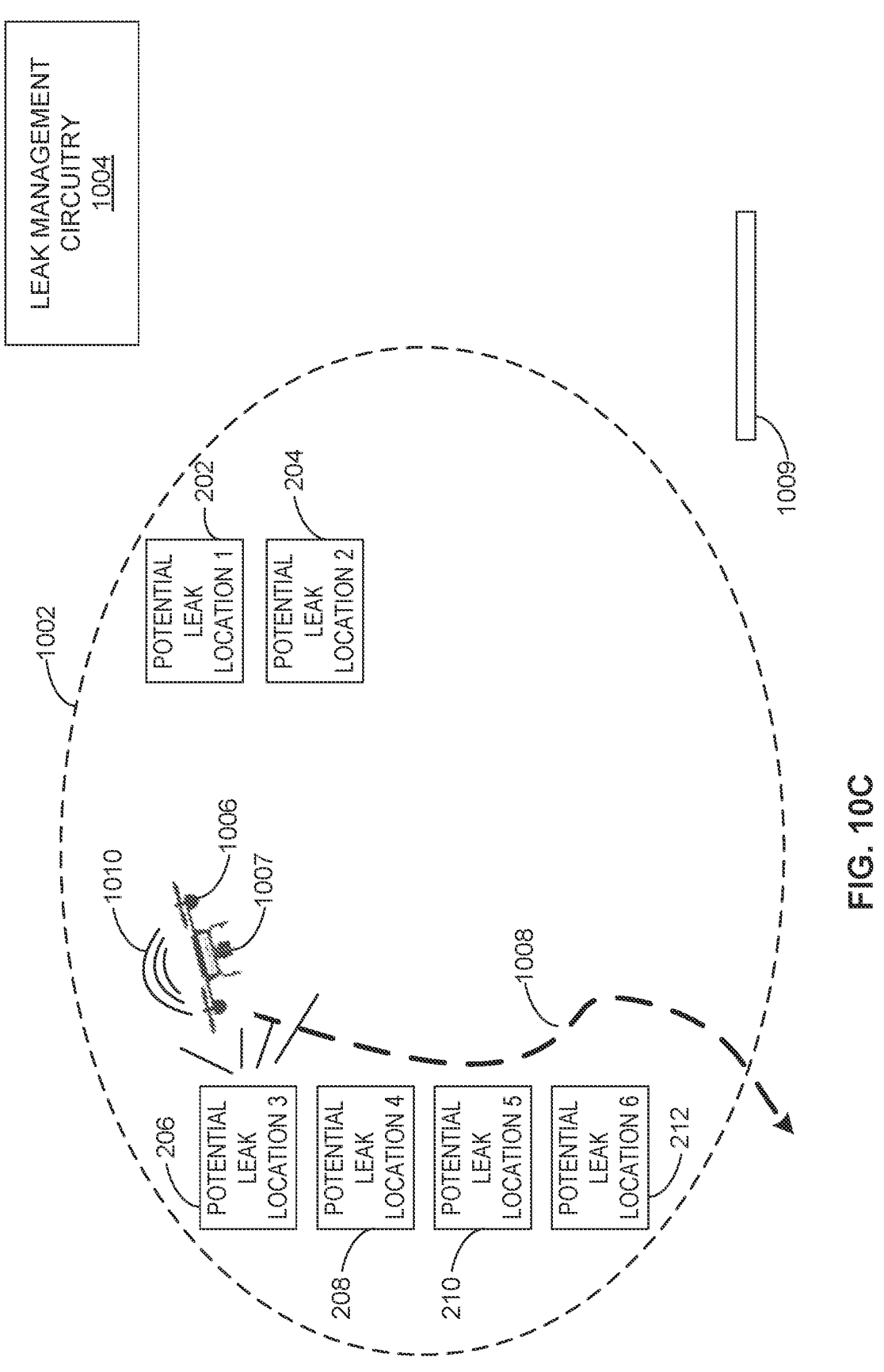

As described above in conjunction with FIG. 9, the mobile sensor platform 1006 can be implemented any suitable mobile device, including the drone depicted in FIGS. 10B and 10C. Additionally or alternatively, the mobile sensor platform 1006 can be implemented by one or more wheeled, legged, or tracked ground-based vehicles. In some examples, the mobile sensor platform 1006 can be carried by a technician.

The predetermined route 1008 is a route that enables the mobile sensor platform 1006 to visit each of the potential leak locations 202, 204, 206, 208, 210, 212 within the leak region 1002. In some examples, a plurality of predetermined routes, including the predetermined route 1008, can be stored by the leak management circuitry 1004, each of which corresponds to a different leak region that could be identified by the leak management circuitry 1004. In other examples, the predetermined route 1008 can be determined after generating the leak region 1002 via one or more vehicle routing algorithms. In some examples, the mobile sensor platform 1006 does not follow the predetermined route 1008. For example, the mobile sensor platform 1006 can be manually operated by a technician. In some such examples, the example predetermined route 1008 can be presented to the user to guide the navigation of the technician. Additionally or alternatively, the mobile sensor platform 1006 can include a plurality of hydrogen concentration sensors arranged in an array, which can permit the mobile sensor platform 1006 to take multiple hydrogen concentration sensor reading simultaneously. In some such examples, the mobile sensor platform 1006 can identify the origin of the leak 1000 by moving towards elevated hydrogen concentrations until the leak 1000 is identified (e.g., "homing-in" to the leak 1000, etc.).

FIG. 10C is a simplified illustration of the leak 1000 and the leak region 1002 of FIG. 10A. In the illustrated example of FIG. 10A, the mobile sensor platform 1006 has traveled along the predetermined route 1008, checked the first potential leak location 202 and the second potential leak location 204 and has moved to the third potential leak location 206. In the illustrated example of FIG. 10C, the mobile sensor platform 1006 identifies, via the mobile sensors 1007, the leak 1000 at the third potential leak location 206. After identifying the location of the source of the leak 1000, the mobile sensor platform 1006 can transmit an example notification 1010 to the leak management circuitry 1004 regarding the location of the source of the leak 1000. For example, the notification 1010 can be transmitted by a wireless connection (e.g., over a local area network, over the Internet, over another wide area network, etc.) and/or a wired connection (e.g., directed wired connection at the standby location 1009, etc.). In some examples, after identifying the leak 1000, the mobile sensor platform can return to the example standby location 1009. In other examples, the mobile sensor platform 1006 can continue along the predetermined route 1008 to check the other potential leak locations 210, 212.

Figures 11A, 11B:
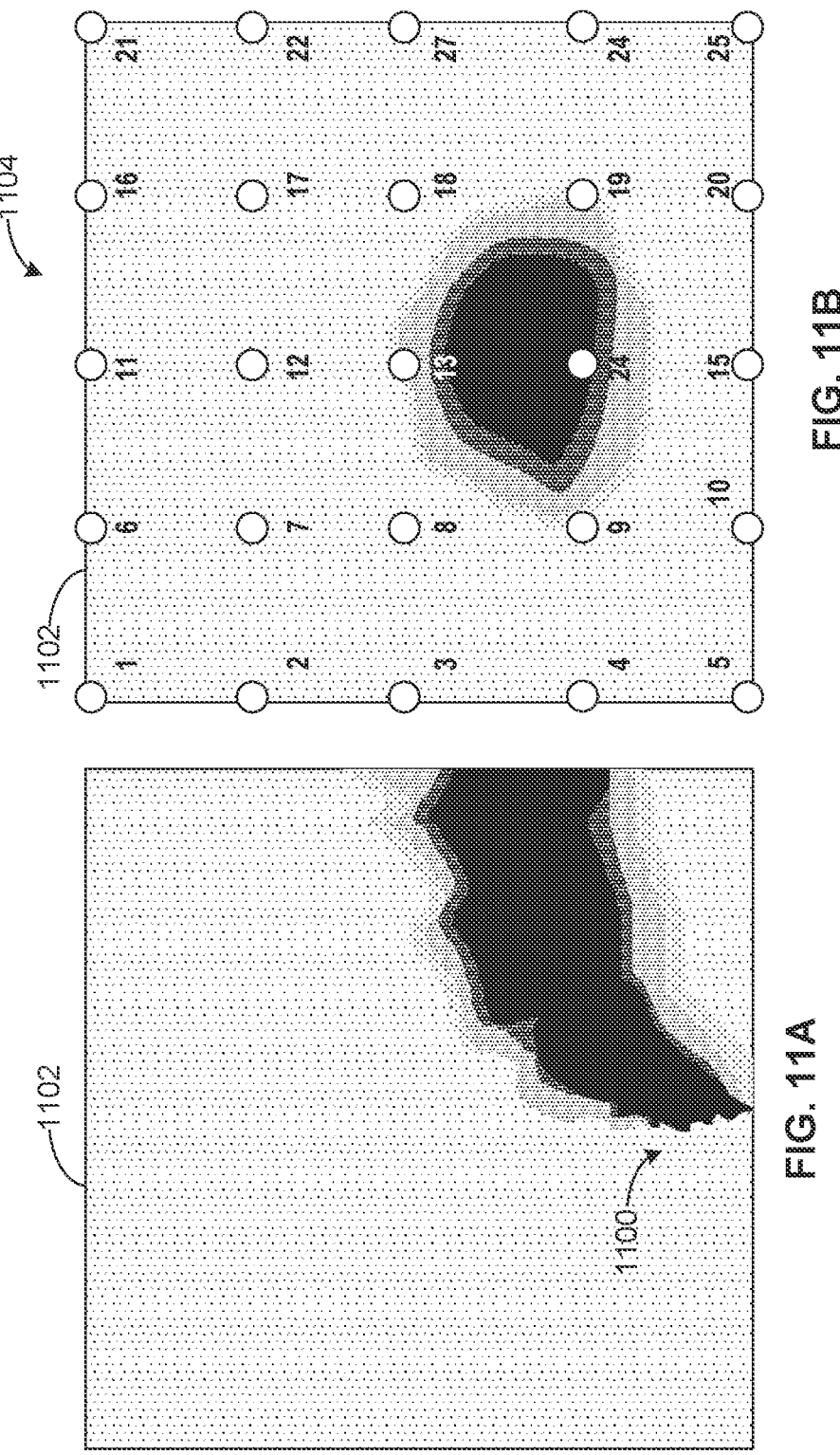
FIGS. 11A and 11B are views of another simulated hydrogen leak of the hydrogen storage system of FIGS. 1A-2.

FIG. 11A and FIG. 11B are a front view and a top view, respectively, of another simulated hydrogen leak 1100 in an example environment 1102. In the illustrated example of FIGS. 11A and 11B, the environment 1102 includes an array of data collection points 1104. In the illustrated example of FIGS. 11A and 11B, the environment 1102 corresponds to a location adjacent to a potential leak location (e.g., the potential leak location 206 of FIGS. 10A-10C, etc.). While the environment 1102 is depicted as a cube, the environment 1102 can be any suitable shape. For example, the shape of the environment 1102 generated by the leak management circuitry 1004 can be based on features of the leak environment that would inhibit the travel of the mobile sensor platform 1006, the environmental conditions (e.g., the wind speed, the wind direction, the temperature, the humidity, etc.), the navigation capabilities of the mobile sensor platform 1006, and/or any other suitable factors.

In some examples, the array of data collection points 1104 represents a location that the mobile sensor platform 1006 takes a hydrogen concentration reading around a potential leak location. For example, the mobile sensor platform 1006 can navigate to each of the array of data collection points 1104 and take a hydrogen concentration reading using the mobile sensors 1007. In some examples, based on the hydrogen concentration information taken by the mobile sensors 1007 of the mobile sensor platform 1006, a technician operating the mobile sensor platform 1006, and/or the leak management circuitry 1004 that the simulated hydrogen leak 1100 is within the environment 1102 and/or a particular location within the environment 1102. In other examples, the array of data collection points 1104 can represent the location(s) of a plurality of hydrogen sensors. In some examples, the hydrogen concentration information taken by the mobile sensors 1007 the severity of the simulated hydrogen leak 1100 can be similarly determined by the mobile sensor platform 1006, a technician operating the mobile sensor platform 1006, and/or the leak management circuitry 1004 within a reasonable margin of error. In the illustrated example of FIGS. 11A AND 11B, the simulated environment

1102 is a 5 meter by 5 meter cube and the array of array of data collection points 1104 are spaced 1.25 meters apart. In the illustrated example of FIGS. 11A and 11B, the array of data collection points 1104 are disposed in a single plane. In other examples, the array of data collection points 1104 can be disposed in multiple planes.

Figure 12:
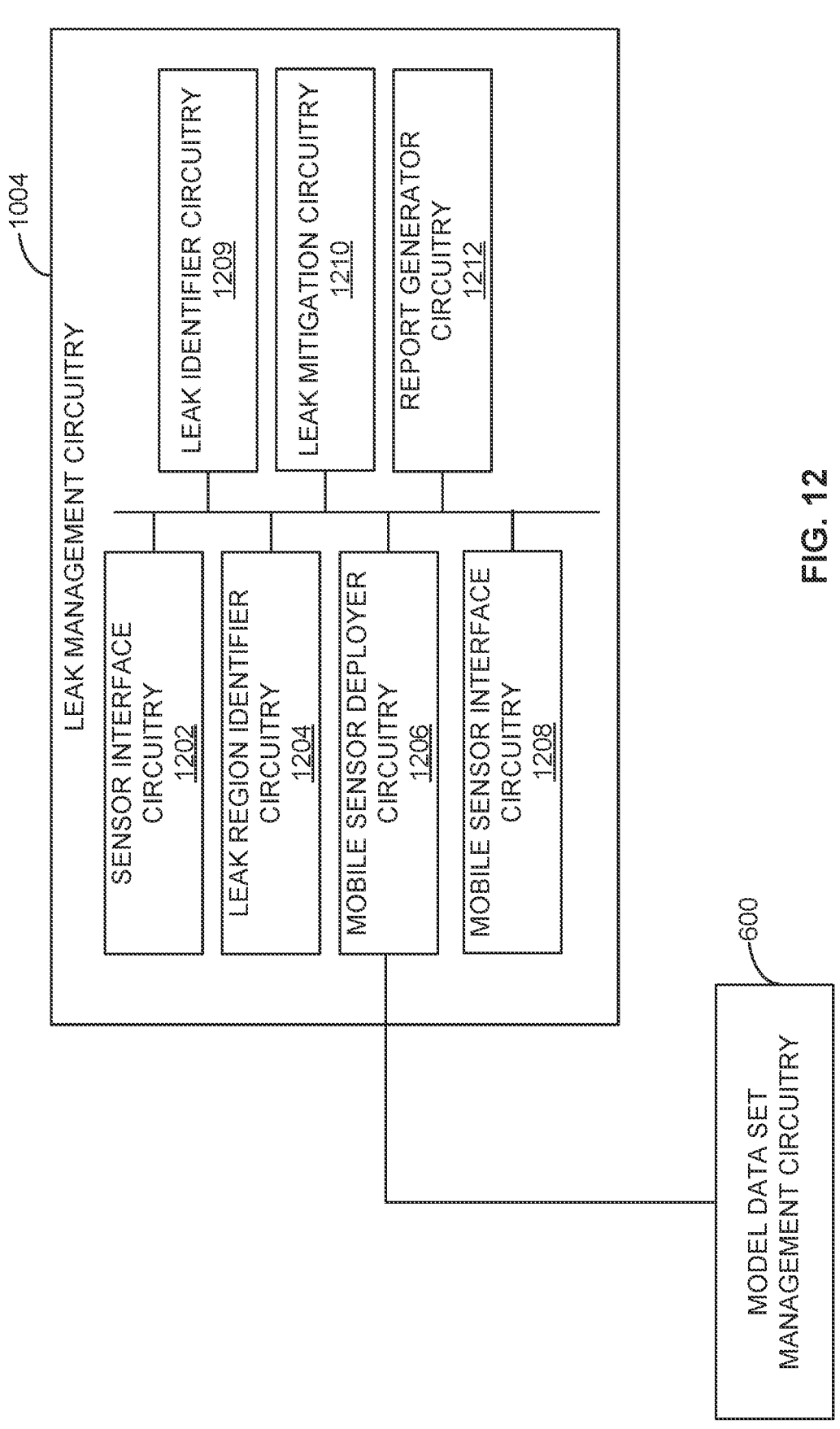
FIG. 12 is a block diagram of the example leak management system of FIG. 10A.

FIG. 12 is a block diagram of the example leak management circuitry 1004 of FIGS. 10A-10C to detect and mitigate the leaks of the hydrogen storage system of FIGS. 1A-2. In the illustrated example of FIG. 12, the leak management circuitry 1004 includes the model data set management circuitry 600 of FIG. 6, sensor interface circuitry 1202, leak region identifier circuitry 1204, mobile sensor interface circuitry 1208, leak identifier circuitry 1209, leak mitigation circuitry 1210, and report generator circuitry 1212. The leak management circuitry 1004 of FIG. 12 may be instantiated (e.g., creating an instance of, bring into being for any length of time, materialize, implement, etc.) by processor circuitry such as a central processing unit executing instructions. Additionally or alternatively, the leak management circuitry 1004 of FIG. 12 may be instantiated (e.g., creating an instance of, bring into being for any length of time, materialize, implement, etc.) by an ASIC or an FPGA structured to perform operations corresponding to the instructions. It should be understood that some or all of the circuitry of FIG. 12 may, thus, be instantiated at the same or different times. Some or all of the circuitry may be instantiated, for example, in one or more threads executing concurrently on hardware and/or in series on hardware. Moreover, in some examples, some or all of the circuitry of FIG. 12 may be implemented by microprocessor circuitry executing instructions to implement one or more virtual machines and/or containers.

The sensor interface circuitry 1202 can access sensor data from the environmental sensors and the hydrogen concentration sensors of the hydrogen storage system 100. For example, the sensor interface circuitry 1202 can receive sensor data from t the temperature sensor 450, the humidity sensor 452, the anemometer 454, and/or the hydrogen sensor (s) 1005 of FIG. 10A. Additionally or alternatively, the sensor interface circuitry 1202 can interface with external sensors (e.g., other sensors at the facility housing the hydrogen storage system 100 and/or a weather service to determine the environmental data. In some examples, the sensor interface circuitry 1202 can transform the received sensor data from a machine-readable format (e.g., a voltage, a current, etc.) to a human-readable format (e.g., a string, a floating-point number, an integer, etc.). In some examples, the sensor interface circuitry 602 is instantiated by processor circuitry executing sensor interface instructions and/or configured to perform operations such as those represented by the flowchart of FIG. 13.

The leak region identifier circuitry 1204 identifies the approximate location of the source of the leak based on the environmental data and/or the hydrogen sensor data. For example, the leak region identifier circuitry 1204 can identify ones of the sensors associated with the hydrogen sensor data (e.g., the hydrogen presence data 902 of FIG. 9, etc.) that indicate elevated hydrogen concentrations. In some examples, the leak region identifier circuitry 1204 can use the environmental data (e.g., the anemometer data 308 of FIG. 9, the temperature and humidity data 310 of FIG. 9, etc.) to generate a region that may contain the potential leak. For example, the leak region identifier circuitry 1204 can use the anemometer data 308 to create a leak region (e.g., the leak region 1002 of FIGS. 10A-10C, etc.) upwind of the sensors indicating elevated hydrogen levels. In some examples, the leak region identifier circuitry 1204 can similarly make inferences about the leak region 1002 based on the hydrogen flow effects caused by the temperature and humidity data 310, etc.). In other examples, the leak region identifier circuitry 1204 can generate the leak region 1002 in any other suitable manner. In some examples, the leak region identifier circuitry 1204 can be implemented by the model data set filterer circuitry 604 of FIG. 6 and/or the data comparator circuitry 606 of FIG. 6. In some such examples, the leak region identifier circuitry 1204 can compare the received hydrogen presence data to modeled hydrogen concentrations stored by the model data set management circuitry 600. In some examples, the leak region identifier circuitry 1204 can use machine-learning and/or artificial intelligence models to determine a similarity between the hydrogen concentration data and the simulated hydrogen concentration data. In some examples, the leak region identifier circuitry 1204 is instantiated by processor circuitry executing data comparator instructions and/or configured to perform operations such as those represented by the flowchart of FIG. 13.

The mobile sensor deployer circuitry 1206 deploys the mobile sensor platform 1006 to the approximate location of the source of the leak. For example, the mobile sensor deployer circuitry 1206 can transmit the leak region 1002 and/or a predetermined route 1008 to the mobile sensor platform 1006 of FIGS. 10B and 10C. In some examples, the mobile sensor deployer circuitry 1206 can send a deployment command to a standby location 1009 to deploy the mobile sensor platform 1006. In some examples, the mobile sensor deployer circuitry 1206 can cause a technician to begin remotely operating the mobile sensor platform 1006. Additionally or alternatively, the mobile sensor deployer circuitry 1206 can cause the mobile sensor platform 1006 to deploy in any other suitable manner. In some examples, the mobile sensor deployer circuitry 1206 is instantiated by processor circuitry executing data comparator instructions and/or configured to perform operations such as those represented by the flowchart of FIG. 13.

The mobile sensor interface circuitry 1208 accesses environmental data. For example, the sensor interface circuitry 1202 can access data from the mobile sensors 1007 of the mobile sensor platform 1006. In some examples, the mobile sensor interface circuitry 1208 can transform the received sensor data from a machine-readable format (e.g., a voltage, a current, etc.). In some examples, the mobile sensor interface circuitry 1208 is instantiated by processor circuitry executing data comparator instructions and/or configured to perform operations such as those represented by the flowchart of FIG. 13.

The leak identifier circuitry 1209 identifies the location and severity of the leak based on the mobile sensor data accessed by the mobile sensor interface circuitry 1208. For example, the leak identifier circuitry 1209 identifies the location of the source of the leak based on the instance of the mobile sensor data. For example, the leak identifier circuitry 1209 can identify the location of the source of the leak based on the data received from the mobile sensors 1007. For example, the leak identifier circuitry 1209 can identify a potential leak location within the identified region having the highest hydrogen concentration. In other examples, the leak identifier circuitry 1209 can use the data from the mobile sensors 1007 (e.g., the mobile hydrogen sensor data 908 of FIG. 9, etc.) to detect the leak in any other suitable matter (e.g., listening for a leak, optically scanning for a leak, etc.). In some examples, the leak identifier circuitry 1209 identifies the severity of the leak based on the instance of the mobile sensor data. For example, the leak identifier circuitry 1209 can take hydrogen concentration measurements for a plurality of points (e.g., the array of data collection points 1104 of FIGS. 11A and 11B, etc.) and perform an analysis to determine a flow rate of hydrogen from the simulated hydrogen leak 1100. In other examples, the leak identifier circuitry 1209 can determine the severity of the leak in any other suitable manner. In some examples, the leak identifier circuitry 1209 is instantiated by processor circuitry executing leak identifier instructions and/or configured to perform operations such as those represented by the flowchart of FIG. 13.

The leak mitigation circuitry 1210 determines the mitigation actions to be taken after the location and severity of the leak is identified. The leak mitigation circuitry 1210 can determine if it is possible to isolate the leak based on the leak identified by the leak identifier circuitry 1209 and then isolate the leak. For example, the leak mitigation circuitry 1210 can determine if the leak can be isolated based on the location of the source of the leak identified. In some such examples, the leak mitigation circuitry 1210 can determine the ability to isolate the leak is based on the availability of alternative routes to route the hydrogen through. In some such examples, the leak mitigation circuitry 1210 can interface with one or more components of the hydrogen storage system 100 to prevent hydrogen from flowing through the part of the hydrogen storage system 100 with the identified leak. In some examples, the leak mitigation circuitry 1210 can send a signal to disable a pump (e.g., one of the pumps 106A, 106B, etc.), close a valve upstream of the leak location, and/or any other suitable controllable feature(s) of the hydrogen storage system 100 (e.g., one or more pump(s), one or more valve(s), one or more throttle(s), one or more vent(s), etc.). For example, if a leak is identified at the fourth potential leak location 208, the leak mitigation circuitry 1210 can isolate the leak (e.g., by routing hydrogen flowing from the hydrogen tank 104 through the pipe defined by the potential leak locations 202, 206, by routing hydrogen entirely through the second pump 106B, etc.). In other examples, the leak mitigation circuitry 1210 can isolate the leak by any other suitable means. In other examples, if the leak mitigation circuitry 1210 determines the leak can be isolated, the leak mitigation circuitry 610 can disable the hydrogen storage system. For example, the leak mitigation circuitry 610 can send a signal to turn off all power components of the hydrogen storage system 100 (e.g., the pumps 106A, 106B, the heat exchangers 108A, 108B, the vaporizer 110, etc.), close all valves of the hydrogen storage system 100, and/or modify any other controllable feature of the hydrogen storage system 100. In other examples, the leak mitigation circuitry 610 can disable the hydrogen storage system 100 in any other suitable manner. Additionally or alternatively, the leak mitigation circuitry 1210 can manage the identified leak by any other suitable means. In some examples, the leak mitigation circuitry 1210 is instantiated by processor circuitry executing leak management instructions and/or configured to perform operations such as those represented by the flowchart of FIG. 13.

The report generator circuitry 1212 generates a report. For example, the report generator circuitry 1212 can generate a report including the location of the identified leak, the severity of the identified leak, the operations of the mobile sensor platform 1006, and/or the mitigation actions taken by the leak mitigation circuitry 1210. In some examples, the report generator circuitry 1212 can, via the sensor interface circuitry 1202, include current hydrogen concentration data (e.g., taken after the mitigation actions by the hydrogen sensor(s) 1005 and/or the mobile sensors 1007, etc.) in the generated report (e.g., to allow operators of the hydrogen storage system 100 to determine if it is safe to have a technician service the leak location, etc.). In other examples, the report generator circuitry 1212 can include any other suitable information in the generated report. In some examples, the report generator circuitry 1212 can generate one or more report(s) when the leak is initially sensed by the hydrogen sensors 1005, after the leak is sensed by the mobile sensor platform 1006, and/or after the location and/or severity of the leak is determined. In some such examples, an operator of the hydrogen storage system 100 and/or the leak management circuitry 1004 can determine the mitigation action to be taken (e.g., via the leak mitigation circuitry 1210, etc.) based on the generated report. In some examples, the report generator circuitry 1212 is instantiated by processor circuitry executing leak management instructions and/or configured to perform operations such as those represented by the flowchart of FIG. 13.

In some examples, the leak management circuitry 1004 includes means for interfacing with a sensor. For example, the means for interfacing with a sensor may be implemented by sensor interface circuitry 1202. In some examples, the sensor interface circuitry 1202 may be instantiated by processor circuitry such as the example processor circuitry 1612 of FIG. 16. For instance, the sensor interface circuitry 1202 may be instantiated by the example microprocessor 1700 of FIG. 17 executing machine executable instructions such as those implemented by at least blocks 1202, 1204 of FIG. 13. In some examples, the sensor interface circuitry 1202 may be instantiated by hardware logic circuitry, which may be implemented by an ASIC, XPU, or the FPGA circuitry 1800 of FIG. 18 structured to perform operations corresponding to the machine readable instructions. Additionally or alternatively, the sensor interface circuitry 1202 may be instantiated by any other combination of hardware, software, and/or firmware. For example, the sensor interface circuitry 1202 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the leak management circuitry 1004 includes means for identifying a leak region. For example, the means for identifying a leak region may be implemented by the leak region identifier circuitry 1204. In some examples, the leak region identifier circuitry 1204 may be instantiated by processor circuitry such as the example processor circuitry 1612 of FIG. 16. For instance, the leak region identifier circuitry 1204 may be instantiated by the example microprocessor 1700 of FIG. 17 executing machine executable instructions such as those implemented by at least block 1306 of FIG. 13. In some examples, the leak region identifier circuitry 1204 may be instantiated by hardware logic circuitry, which may be implemented by an ASIC, XPU, or the FPGA circuitry 1800 of FIG. 18 structured to perform operations corresponding to the machine readable instructions. Additionally or alternatively, the leak region identifier circuitry 1204 may be instantiated by any other combination of hardware, software, and/or firmware. For example, the leak region identifier circuitry 1204 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.\

In some examples, the leak management circuitry 1004 includes means for deploying a mobile sensor platform. For example, the means for deploying a mobile sensor platform may be implemented by the mobile sensor deployer circuitry 1206. In some examples, the mobile sensor deployer circuitry 1206 may be instantiated by processor circuitry such as the example processor circuitry 1612 of FIG. 16. For instance, the mobile sensor deployer circuitry 1206 may be instantiated by the example microprocessor 1700 of FIG. 17 executing machine executable instructions such as those implemented by at least block 1308 of FIG. 13. In some examples, the mobile sensor deployer circuitry 1206 may be instantiated by hardware logic circuitry, which may be implemented by an ASIC, XPU, or the FPGA circuitry 1800 of FIG. 18 structured to perform operations corresponding to the machine readable instructions. Additionally or alternatively, the mobile sensor deployer circuitry 1206 may be instantiated by any other combination of hardware, software, and/or firmware. For example, the mobile sensor deployer circuitry 1206 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the leak management circuitry 1004 includes means for interfacing with a mobile sensor platform. For example, the means for interfacing with a mobile sensor platform may be implemented by the mobile sensor interface circuitry 1208. In some examples, the mobile sensor interface circuitry 1208 may be instantiated by processor circuitry such as the example processor circuitry 1612 of FIG. 16. For instance, the mobile sensor interface circuitry 1208 may be instantiated by the example microprocessor 1700 of FIG. 17 executing machine executable instructions such as those implemented by at least block 1310 of FIG. 13. In some examples, the mobile sensor interface circuitry 1208 may be instantiated by hardware logic circuitry, which may be implemented by an ASIC, XPU, or the FPGA circuitry 1800 of FIG. 18 structured to perform operations corresponding to the machine readable instructions. Additionally or alternatively, the mobile sensor interface circuitry 1208 may be instantiated by any other combination of hardware, software, and/or firmware. For example, the mobile sensor interface circuitry 1208 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the leak management circuitry 1004 includes means for identifying a leak. For example, the means for identifying a leak may be implemented by the leak identifier circuitry 1209. In some examples, the leak identifier circuitry 1209 may be instantiated by processor circuitry such as the example processor circuitry 1612 of FIG. 16. For instance, the leak identifier circuitry 1209 may be instantiated by the example microprocessor 1700 of FIG. 17 executing machine executable instructions such as those implemented by at least blocks 1312, 1314 of FIG. 13. In some examples, the leak identifier circuitry 1209 may be instantiated by hardware logic circuitry, which may be implemented by an ASIC, XPU, or the FPGA circuitry 1800 of FIG. 18 structured to perform operations corresponding to the machine readable instructions. Additionally or alternatively, the leak identifier circuitry 1209 may be instantiated by any other combination of hardware, software, and/or firmware. For example, the leak identifier circuitry 1209 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the leak management circuitry 1004 includes means for mitigating a leak. For example, the means for mitigating a leak may be implemented by the leak mitigation circuitry 1210. In some examples, the leak mitigation circuitry 1210 may be instantiated by processor circuitry such as the example processor circuitry 1612 of FIG. 16. For instance, the leak mitigation circuitry 1210 may be instantiated by the example microprocessor 1700 of FIG. 17 executing machine executable instructions such as those implemented by at least blocks 1316, 1318, 1320 of FIG. 13. In some examples, the leak mitigation circuitry 1210 may be instantiated by hardware logic circuitry, which may be implemented by an ASIC, XPU, or the FPGA circuitry 1800 of FIG. 18 structured to perform operations corresponding to the machine readable instructions. Additionally or alternatively, the leak mitigation circuitry 1210 may be instantiated by any other combination of hardware, software, and/or firmware. For example, the leak mitigation circuitry 1210 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the leak management circuitry 1004 includes means for generating a report. For example, the means for generating a report may be implemented by the report generator circuitry 1212. In some examples, the report generator circuitry 1212 may be instantiated by processor circuitry such as the example processor circuitry 1612 of FIG. 16. For instance, the report generator circuitry 1212 may be instantiated by the example microprocessor 1700 of FIG. 17 executing machine executable instructions such as those implemented by at least block 1322 of FIG. 13. In some examples, the report generator circuitry 1212 may be instantiated by hardware logic circuitry, which may be implemented by an ASIC, XPU, or the FPGA circuitry 1800 of FIG. 18 structured to perform operations corresponding to the machine readable instructions. Additionally or alternatively, the report generator circuitry 1212 may be instantiated by any other combination of hardware, software, and/or firmware. For example, the report generator circuitry 1212 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

While an example manner of implementing the leak management circuitry 1004 of FIGS. 10A-10C is illustrated in FIG. 12, one or more of the elements, processes, and/or devices illustrated in FIG. 12 may be combined, divided, re-arranged, omitted, eliminated, and/or implemented in any other way. Further, the example sensor interface circuitry 1202, the example leak region identifier circuitry 1204, the example mobile sensor deployer circuitry 1206, the example mobile sensor interface circuitry 1208, the leak identifier circuitry 1209, the leak mitigation circuitry 1210, the report generator circuitry 1212, and/or, more generally, the example leak management circuitry 1004 of FIGS. 10A-10C, may be implemented by hardware alone or by hardware in combination with software and/or firmware. Thus, for example, any of the example sensor interface circuitry 1202, the example leak region identifier circuitry 1204, the example mobile sensor deployer circuitry 1206, the example mobile sensor interface circuitry 1208, the leak identifier circuitry 1209, the leak mitigation circuitry 1210, the report generator circuitry 1212, and/or, more generally, the example leak management circuitry 1004, could be implemented by processor circuitry, analog circuit(s), digital circuit(s), logic circuit(s), programmable processor(s), programmable microcontroller(s), graphics processing unit(s) (GPU(s)), digital signal processor(s) (DSP(s)), application specific integrated circuit(s) (ASIC(s)), programmable logic device(s) (PLD(s)), and/or field programmable logic device (s) (FPLD(s)) such as Field Programmable Gate Arrays (FPGAs). Further still, the example leak management circuitry 1004 of FIGS. 10A-10C may include one or more elements, processes, and/or devices in addition to, or instead of, those illustrated in FIG. 12, and/or may include more than one of any or all of the illustrated elements, processes and devices.

A flowchart representative of example machine readable instructions, which may be executed to configure processor circuitry to implement the leak management circuitry 1004 of FIGS. 10A-10C, is shown in FIG. 12. The machine readable instructions may be one or more executable programs or portion(s) of an executable program for execution by processor circuitry, such as the processor circuitry 1612 shown in the example processor platform 1600 discussed below in connection with FIG. 16 and/or the example processor circuitry discussed below in connection with FIGS. 16 and/or 17. The program may be embodied in software stored on one or more non-transitory computer readable storage media such as a compact disk (CD), a floppy disk, a hard disk drive (HDD), a solid-state drive (SSD), a digital versatile disk (DVD), a Blu-ray disk, a volatile memory (e.g., Random Access Memory (RAM) of any type, etc.), or a non-volatile memory (e.g., electrically erasable programmable read-only memory (EEPROM), FLASH memory, an HDD, an SSD, etc.) associated with processor circuitry located in one or more hardware devices, but the entire program and/or parts thereof could alternatively be executed by one or more hardware devices other than the processor circuitry and/or embodied in firmware or dedicated hardware. The machine readable instructions may be distributed across multiple hardware devices and/or executed by two or more hardware devices (e.g., a server and a client hardware device). For example, the client hardware device may be implemented by an endpoint client hardware device (e.g., a hardware device associated with a user) or an intermediate client hardware device (e.g., a radio access network (RAN)) gateway that may facilitate communication between a server and an endpoint client hardware device). Similarly, the non-transitory computer readable storage media may include one or more mediums located in one or more hardware devices. Further, although the example program is described with reference to the flowchart illustrated in FIG. 13, many other methods of implementing the example leak management circuitry 1004 may alternatively be used. For example, the order of execution of the blocks may be changed, and/or some of the blocks described may be changed, eliminated, or combined. Additionally or alternatively, any or all of the blocks may be implemented by one or more hardware circuits (e.g., processor circuitry, discrete and/or integrated analog and/or digital circuitry, an FPGA, an ASIC, a comparator, an operational-amplifier (op-amp), a logic circuit, etc.) structured to perform the corresponding operation without executing software or firmware. The processor circuitry may be distributed in different network locations and/or local to one or more hardware devices (e.g., a single-core processor (e.g., a single core central processor unit (CPU)), a multi-core processor (e.g., a multi-core CPU, an XPU, etc.) in a single machine, multiple processors distributed across multiple servers of a server rack, multiple processors distributed across one or more server racks, a CPU and/or a FPGA located in the same package (e.g., the same integrated circuit (IC) package or in two or more separate housings, etc.).

Figure 13:
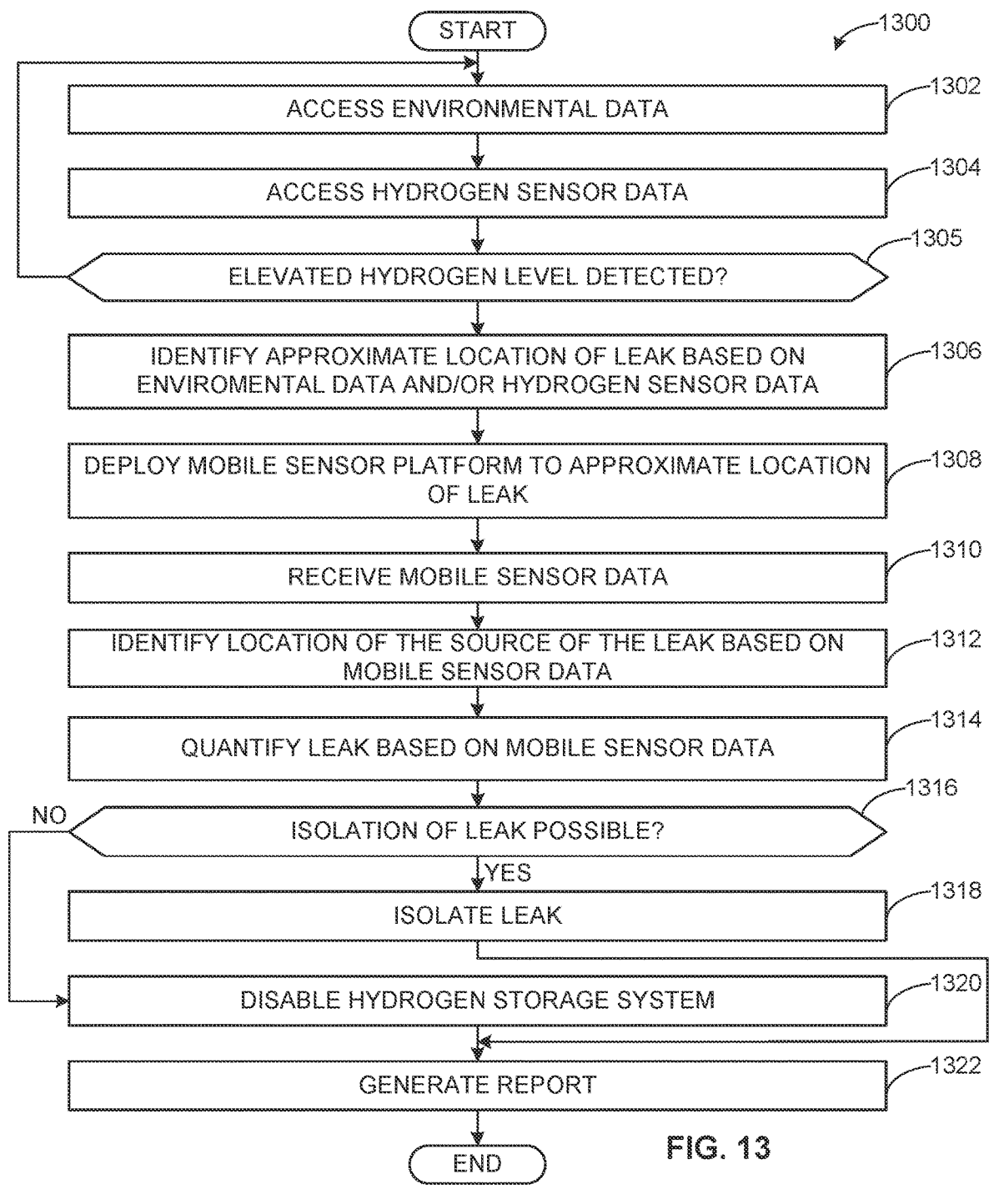
FIG. 13 is a flowchart representative of example machine readable instructions and/or example operations that may be executed by example processor circuitry to implement the leak management system of FIG. 12.

FIG. 13 is a flowchart representative of example machine readable instructions and/or example operations 1300 that may be executed and/or instantiated by processor circuitry to identify the location and the severity of a leak in the hydrogen storage system 100. The machine readable instructions and/or the operations 1300 of FIG. 13 begin at block 1302, at which the sensor interface circuitry 1202 accesses environmental data. For example, the sensor interface circuitry 1202 can access data from the temperature sensor 450, the humidity sensor 452, the anemometer 454 of FIG. 10A. Additionally or alternatively, the sensor interface circuitry 1202 can interface with external sensors (e.g., other sensors at the facility housing the hydrogen storage system 100 and/or a weather service to determine the environmental data). In some examples, the sensor interface circuitry 602 can transform the received sensor data from a machine-readable format (e.g., a voltage, a current, etc.) to a human-readable format (e.g., a string, a floating-point number, an integer, etc.).

At block 1304, the sensor interface circuitry 1202 accesses hydrogen sensor data. For example, the sensor interface circuitry 1202 can access data from the hydrogen sensor(s) 1005 of FIG. 10A. In other examples, the sensor interface circuitry 1202 can receive the hydrogen sensor data from any other suitable source. In some examples, the sensor interface circuitry 602 can transform the received sensor data from a machine-readable format (e.g., a voltage, a current, etc.) to a human-readable format (e.g., a string, a floating-point number, an integer, etc.).

At block 1305, the sensor interface circuitry 1202 determines if an elevated hydrogen concentration data is detected. For example, the sensor interface circuitry 1202 can determine if one or more of the hydrogen sensors 1005 are outputting an above-nominal hydrogen concentration output (e.g., a hydrogen concentration above the expected ambient hydrogen concentration, etc.). If the sensor interface circuitry 1202 detects an elevated hydrogen concentration level, the operations 1300 advance to block 1306. If the sensor interface circuitry 1202 does not detect an elevated hydrogen concentration level, the operations 1300 return to block 1302.

At block 1306, the leak region identifier circuitry 1204 identifies the approximate location of the source of the leak based on the environmental data and/or the hydrogen sensor data. For example, the leak region identifier circuitry 1204 can identify ones of the sensors associated with the hydrogen sensor data (e.g., the hydrogen presence data 902 of FIG. 9, etc.) that indicate elevated hydrogen concentrations. In some examples, the leak region identifier circuitry 1204 can use the environmental data (e.g., the anemometer data 308 of FIG. 9, the temperature and humidity data 310 of FIG. 9, etc.) to generate a region that may contain the potential leak. For example, the leak region identifier circuitry 1204 can use the anemometer data 308 to create a leak region (e.g., the leak region 1002 of FIGS. 10A-10C, etc.) upwind of the sensors indicating elevated hydrogen levels. In some examples, the leak region identifier circuitry 1204 can similarly make inferences about the leak region 1002 based on the hydrogen flow effects caused by the temperature and humidity data 310, etc.). In some examples, the leak region identifier circuitry 1204 can determine the leak region 1002 by executing the operations associated with blocks 706, 708, 710 of FIG. 7. In some such examples, the leak region identifier circuitry 1204 can compare the received hydrogen presence data to modeled hydrogen concentrations stored by the model data set management circuitry 600. In other examples, the leak region identifier circuitry 1204 can generate the leak region 1002 in any other suitable manner.

At block 1308, the mobile sensor deployer circuitry 1206 deploys the mobile sensor platform 1006 to approximate location of the source of the leak. For example, the mobile sensor deployer circuitry 1206 can transmit the leak region 1002 and/or a predetermined route 1008 to the mobile sensor platform 1006 of FIGS. 10B and 10C. In some examples, the mobile sensor deployer circuitry 1206 can send a deployment command to a standby location 1009 to deploy the mobile sensor platform 1006. In some examples, the mobile sensor deployer circuitry 1206 can cause a technician to begin remotely operating the mobile sensor platform 1006. Additionally or alternatively, the mobile sensor deployer circuitry 1206 can cause the mobile sensor platform 1006 to deploy in any other suitable manner. At block 1310, the mobile sensor interface circuitry 1208 receives mobile sensor data. For example, the sensor interface circuitry 1202 can access data from the mobile sensors 1007 of the mobile sensor platform 1006. In some examples, the mobile sensor deployer circuitry 1206 can transform the received sensor data from a machine-readable format (e.g., a voltage, a current, etc.) to a human-readable format (e.g., a number, etc.).

At block 1312, the leak identifier circuitry 1209 identifies the location of the source of the leak based on the mobile sensors 1007. For example, the leak identifier circuitry 1209 can identify the location of the source of the leak based on the data received from the mobile sensors 1007. For example, the leak identifier circuitry 1209 can identify a potential leak location within the identified region having the highest hydrogen concentration. In other examples, the leak identifier circuitry 1209 can use data from the mobile sensors 1007 (e.g., the mobile hydrogen sensor data 908 of FIG. 9, etc.) to detect the leak in any other suitable matter (e.g., listening for a leak, optically scanning for a leak, etc.). At block 1314, the leak identifier circuitry 1209 identifies the severity of the leak based on the instance of the mobile sensor data. For example, the leak identifier circuitry 1209 can take hydrogen concentration measurements for a plurality of points (e.g., array of data collection points 1104 of FIGS. 11A and 11B, etc.) and perform an analysis to determine a flow rate of hydrogen from the simulated hydrogen leak 1100. In other examples, the leak identifier circuitry 1209 can determine the severity of the leak in any other suitable manner.

At block 1316, the leak mitigation circuitry 1210 determines if the isolation of the leak is possible. For example, the leak mitigation circuitry 1210 can determine if the leak can be isolated based on the location of the source of the leak identified during the execution of block 1312. In some examples, the leak mitigation circuitry 1210 can determine the ability to isolate the leak is based on the availability of alternative routes to route the hydrogen through. If the leak mitigation circuitry 1210 determines the leak can be isolated, the operations 1300 advance to block 1318. If the leak mitigation circuitry 1210 determines the leak cannot be isolated, the operations 1300 advance to block 1320.

At block 1318, the leak mitigation circuitry 1210 isolates the leak. For example, the leak mitigation circuitry 1210 can interface with one or more components of the hydrogen storage system 100 to prevent hydrogen from flowing through the part of the hydrogen storage system 100 with the identified leak. In some examples, the leak mitigation circuitry 1210 can send a signal to disable a pump (e.g., one of the pumps 106A, 106B, etc.), close a valve upstream of the leak location, and/or any other suitable controllable feature of the hydrogen storage system 100. For example, if a leak is identified at potential leak location 208, the leak mitigation circuitry 1210 can isolate the leak (e.g., by routing hydrogen flowing from the hydrogen tank 104 through the pipe defined by the potential leak locations 202, 206, by routing hydrogen entirely through the second pump 106B, etc.). In other examples, the leak mitigation circuitry 1210 can isolate the leak by any other suitable means.

At block 1320, the leak mitigation circuitry 1210 disables the hydrogen storage system. For example, the leak mitigation circuitry 1210 can turn off all power components of the hydrogen storage system 100 (e.g., the pumps 106A, 106B, the heat exchangers 108A, 108B, the vaporizer 110, etc.) and close all valves of the hydrogen storage system 100. In other examples, the leak mitigation circuitry 1210 can disable the hydrogen storage system 100 in any other suitable manner.

At block 1322, the report generator circuitry 1212 generates a report. For example, the report generator circuitry 1212 can generate a report including the location of the identified leak, the severity of the identified leak, the operations of the mobile sensor platform 1006, and/or the mitigation actions taken by the leak mitigation circuitry 1210 during the execution of blocks 1316, 1318, 1320. In some examples, the report generator circuitry 1212 can, via the sensor interface circuitry 1202, include current hydrogen concentration data (e.g., taken after the mitigation actions by the hydrogen sensor(s) 1005, etc.) in the generated report (e.g., to allow operators of the hydrogen storage system 100 to determine if it is safe to have a technician service the leak location, etc.). In other examples, the report generator circuitry 1212 can include any other suitable information in the generated report. The operations 1300 then end.

Figure 14:
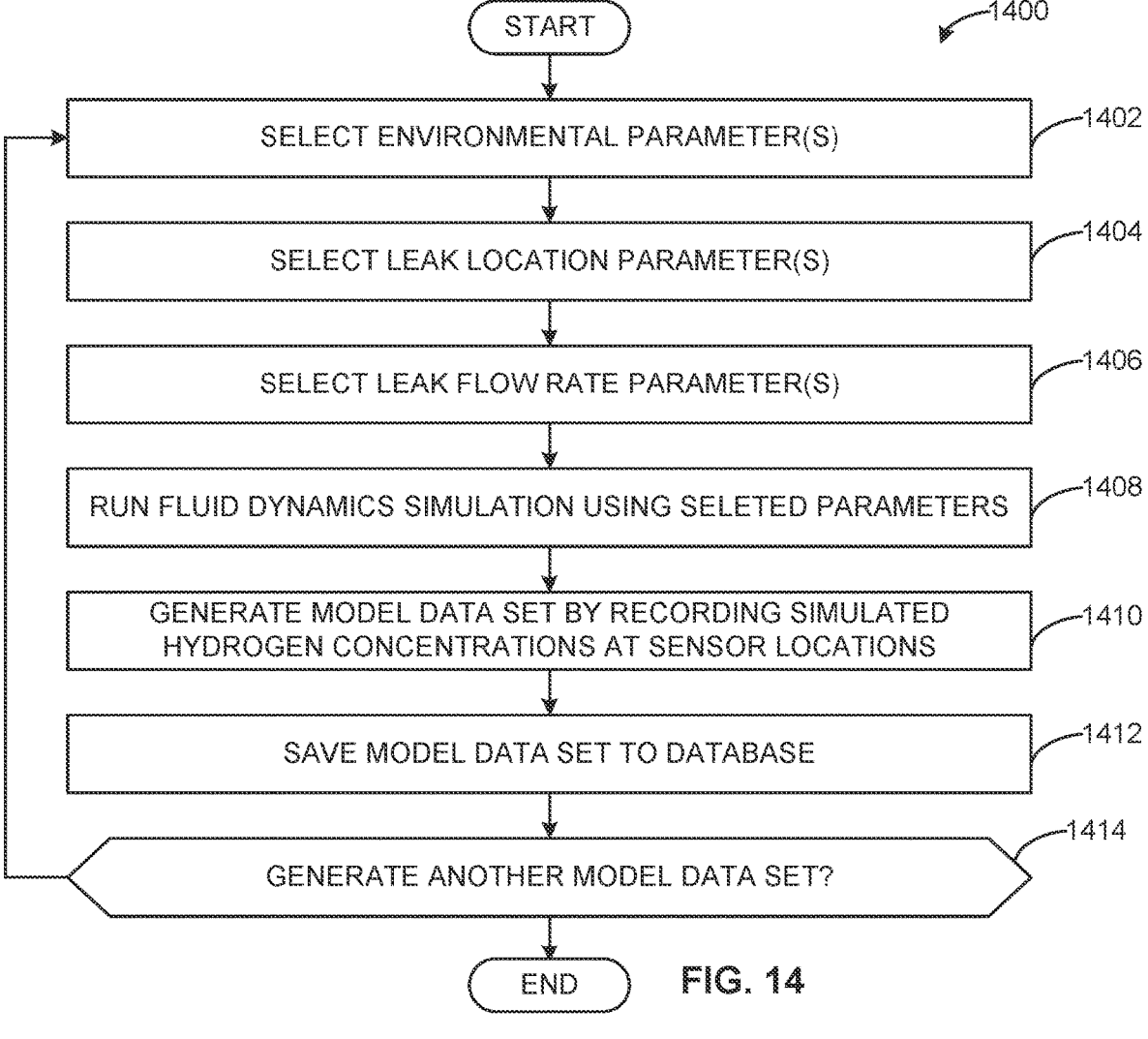
FIG. 14 is a flowchart representative of example machine readable instructions and/or example operations that may be executed by example processor circuitry to implement the model data set management circuitry of FIGS. 6 and 11.

A flowchart representative of example machine readable instructions, which may be executed to configure processor circuitry to implement the model data set management circuitry 600 of FIGS. 6 and 11, is shown in FIG. 14. The machine readable instructions may be one or more executable programs or portion(s) of an executable program for execution by processor circuitry, such as the processor circuitry 1512 and/or the processor circuitry 1612 shown in the example processor platform 1500 and the example processor platform 1600, respectively discussed below in connection with FIGS. 14 and 15 and/or the example processor circuitry discussed below in connection with FIGS. 16 and/or 17. The program may be embodied in software stored on one or more non-transitory computer readable storage media such as a compact disk (CD), a floppy disk, a hard disk drive (HDD), a solid-state drive (SSD), a digital versatile disk (DVD), a Blu-ray disk, a volatile memory (e.g., Random Access Memory (RAM) of any type, etc.), or a non-volatile memory (e.g., electrically erasable programmable read-only memory (EEPROM), FLASH memory, an HDD, an SSD, etc.) associated with processor circuitry located in one or more hardware devices, but the entire program and/or parts thereof could alternatively be executed by one or more hardware devices other than the processor circuitry and/or embodied in firmware or dedicated hardware. The machine readable instructions may be distributed across multiple hardware devices and/or executed by two or more hardware devices (e.g., a server and a client hardware device). For example, the client hardware device may be implemented by an endpoint client hardware device (e.g., a hardware device associated with a user) or an intermediate client hardware device (e.g., a radio access network (RAN)) gateway that may facilitate communication between a server and an endpoint client hardware device). Similarly, the non-transitory computer readable storage media may include one or more mediums located in one or more hardware devices. Further, although the example program is described with reference to the flowchart illustrated in FIG. 14, many other methods of implementing the example model data set management circuitry 600 may alternatively be used. For example, the order of execution of the blocks may be changed, and/or some of the blocks described may be changed, eliminated, or combined. Additionally or alternatively, any or all of the blocks may be implemented by one or more hardware circuits (e.g., processor circuitry, discrete and/or integrated analog and/or digital circuitry, an FPGA, an ASIC, a comparator, an operational-amplifier (op-amp), a logic circuit, etc.) structured to perform the corresponding operation without executing software or firmware. The processor circuitry may be distributed in different network locations and/or local to one or more hardware devices (e.g., a single-core processor (e.g., a single core central processor unit (CPU)), a multi-core processor (e.g., a multi-core CPU, an XPU, etc.) in a single machine, multiple processors distributed across multiple servers of a server rack, multiple processors distributed across one or more server racks, a CPU and/or a FPGA located in the same package (e.g., the same integrated circuit (IC) package or in two or more separate housings, etc.).

FIG. 14 is a flowchart representative of example machine readable instructions and/or example operations 1400 that may be executed and/or instantiated by processor circuitry to generate an instance of the hydrogen leak model data for use by the leak management circuitry 102 and/or the leak management circuitry 1004 of FIGS. 10A-10C. The machine readable instructions and/or the operations 1400 of FIG. 14 begin at block 1402, the parameter selector circuitry 616 selects environmental parameters to use in the simulation. For example, the parameter selector circuitry 616 can select a wind speed, a wind direction, a temperature and/or a humidity to use in the simulation. In some examples, the parameter selector circuitry 616 can select any other suitable parameters. At block 1404, the parameter selector circuitry 616 selects a leak location parameter. For example, the parameter selector circuitry 616 can select a leak location on a simulated recreation of the hydrogen storage system 100 to simulate the hydrogen leak. For example, the parameter selector circuitry 616 can select one of the potential leak locations 202-246. In other examples, the parameter selector circuitry 616 can select any other location on the hydrogen storage system 100 to simulate a leak. At block 1406, the parameter selector circuitry 616 selects a leak severity parameter(s). For example, the parameter selector circuitry 616 can select a flow rate (e.g., a volume flow rate, a mass flow rate, etc.) of the hydrogen through the hydrogen leak. In other examples, the parameter selector circuitry 616 can select any other suitable severity parameter.

At block 1408, the leak simulator circuitry 618 runs a fluid dynamics simulation using the selected parameters. For example, the leak simulator circuitry 618 can, via a computational fluid dynamics simulation, generate a fluid model of the leak using the selected environmental parameters, the selected leak location parameters, and the leak severity parameters. In other examples, the leak simulator circuitry 618 can generate fluid dynamics model in any other suitable manner. In some such examples, the leak simulator circuitry 618 can run a simulation that simulates the hydrogen concentration throughout the model of the hydrogen storage system 100.

At block 1410, the leak simulator circuitry 618 generates a model data set by recording the simulated hydrogen concentration at the sensor locations throughout the simulation of the hydrogen storage system 100 using the leak. For example, the leak simulator circuitry 618 can record the hydrogen concentrations at the points of the model corresponding to the location of the hydrogen concentration sensors 402-448 of FIGS. 4A and 4B. At block 1412, the leak simulator circuitry 618 saves the model data set to the simulation database 614. For example, the leak simulator circuitry 618 can save the simulated hydrogen concentrations and the selected parameters to the simulation database 614. At block 1414, the parameter selector circuitry 616 determines if another simulation is to be run. For example, the parameter selector circuitry 616 can determine to a run another simulation if there are simulations including a parameter that has not been run yet. In other examples, the parameter selector circuitry 616 can determine if another simulation is to be run by any other suitable means. If the parameter selector circuitry 616 determines another simulation is to be run, the operations 1400 return to block 1402. If the parameter selector circuitry 616 determines another simulation is not be run, the operations 1400 end.

As mentioned above, the example operations of FIGS. 7, 8, 13, and 14 may be implemented using executable instructions (e.g., computer and/or machine readable instructions) stored on one or more non-transitory computer and/or machine readable media such as optical storage devices, magnetic storage devices, an HDD, a flash memory, a read-only memory (ROM), a CD, a DVD, a cache, a RAM of any type, a register, and/or any other storage device or storage disk in which information is stored for any duration (e.g., for extended time periods, permanently, for brief instances, for temporarily buffering, and/or for caching of the information). As used herein, the terms non-transitory computer readable medium, non-transitory computer readable storage medium, non-transitory machine readable medium, and non-transitory machine readable storage medium are expressly defined to include any type of computer readable storage device and/or storage disk and to exclude propagating signals and to exclude transmission media. As used herein, the terms "computer readable storage device" and "machine readable storage device" are defined to include any physical (mechanical and/or electrical) structure to store information, but to exclude propagating signals and to exclude transmission media. Examples of computer readable storage devices and machine readable storage devices include random access memory of any type, read only memory of any type, solid state memory, flash memory, optical discs, magnetic disks, disk drives, and/or redundant array of independent disks (RAID) systems. As used herein, the term "device" refers to physical structure such as mechanical and/or electrical equipment, hardware, and/or circuitry that may or may not be configured by computer readable instructions, machine readable instructions, etc., and/or manufactured to execute computer readable instructions, machine readable instructions, etc.

Figure 15:
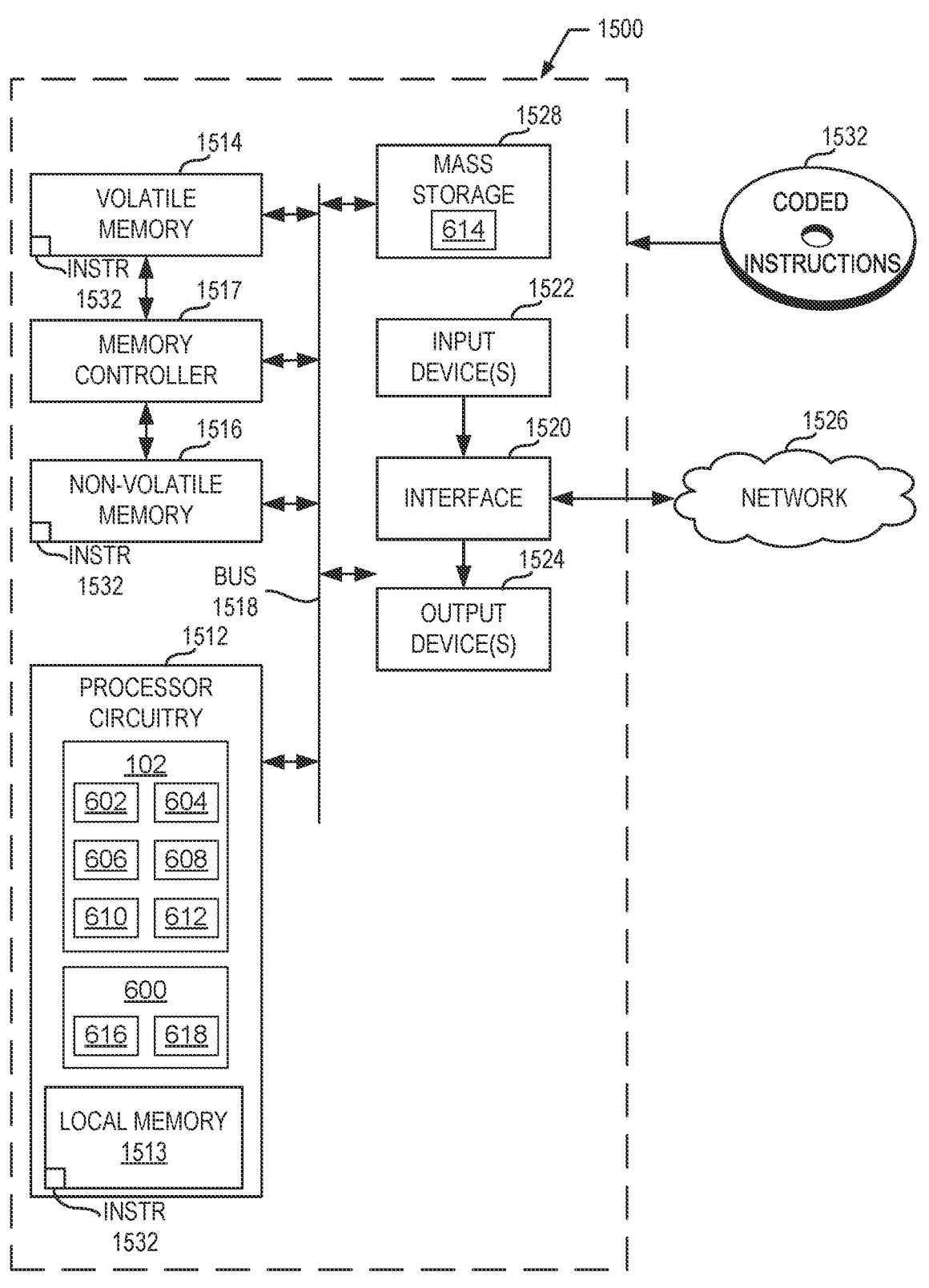
FIG. 15 is a block diagram of an example processing platform including processor circuitry structured to execute the example machine readable instructions and/or the example operations of FIGS. 7, 8, and/or 14 to implement the leak management system and/or the model data set management circuitry of FIG. 6.

FIG. 15 is a block diagram of an example processor platform 1500 structured to execute and/or instantiate the machine readable instructions and/or the operations of FIG. 7 to implement the leak management circuitry 102 of FIGS. 1A, 1B, and 6. The processor platform 1500 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a headset (e.g., an augmented reality (AR) headset, a virtual reality (VR) headset, etc.) or other wearable device, or any other type of computing device.

The processor platform 1500 of the illustrated example includes processor circuitry 1512. The processor circuitry 1512 of the illustrated example is hardware. For example, the processor circuitry 1512 can be implemented by one or more integrated circuits, logic circuits, FPGAs, microprocessors, CPUs, GPUs, DSPs, and/or microcontrollers from any desired family or manufacturer. The processor circuitry 1512 may be implemented by one or more semiconductor-based (e.g., silicon based) devices. In this example, the processor circuitry 1512 implements the example sensor interface circuitry 602, the example model data set filterer circuitry 604, the data comparator circuitry 606, the leak identifier circuitry 608, the leak mitigation circuitry 610, the report generator circuitry 612, the parameter selector circuitry 616, and the leak simulator circuitry 618.

The processor circuitry 1512 of the illustrated example includes a local memory 1513 (e.g., a cache, registers, etc.). The processor circuitry 1512 of the illustrated example is in communication with a main memory including a volatile memory 1514 and a non-volatile memory 1516 by a bus 1518. The volatile memory 1514 may be implemented by Synchronous Dynamic Random Access Memory (SDRAM), Dynamic Random Access Memory (DRAM), RAMBUS® Dynamic Random Access Memory (RDRAM®), and/or any other type of RAM device. The non-volatile memory 1516 may be implemented by flash memory and/or any other desired type of memory device. Access to the main memory 1514, 1516 of the illustrated example is controlled by a memory controller 1517.

The processor platform 1500 of the illustrated example also includes interface circuitry 1520. The interface circuitry 1520 may be implemented by hardware in accordance with any type of interface standard, such as an Ethernet interface, a universal serial bus (USB) interface, a Bluetooth® interface, a near field communication (NFC) interface, a Peripheral Component Interconnect (PCI) interface, and/or a Peripheral Component Interconnect Express (PCIe) interface.

In the illustrated example, one or more input devices 1522 are connected to the interface circuitry 1520. The input device(s) 1522 permit(s) a user to enter data and/or commands into the processor circuitry 1512. The input device(s) 1522 can be implemented by, for example, an audio sensor, a microphone, a camera (still or video), a keyboard, a button, a mouse, a touchscreen, a track-pad, a trackball, an isopoint device, and/or a voice recognition system.

One or more output devices 1524 are also connected to the interface circuitry 1520 of the illustrated example. The output device(s) 1524 can be implemented, for example, by display devices (e.g., a light emitting diode (LED), an organic light emitting diode (OLED), a liquid crystal display (LCD), a cathode ray tube (CRT) display, an in-place switching (IPS) display, a touchscreen, etc.), a tactile output device, a printer, and/or speaker. The interface circuitry 1520 of the illustrated example, thus, typically includes a graphics driver card, a graphics driver chip, and/or graphics processor circuitry such as a GPU.

The interface circuitry 1520 of the illustrated example also includes a communication device such as a transmitter, a receiver, a transceiver, a modem, a residential gateway, a wireless access point, and/or a network interface to facilitate exchange of data with external machines (e.g., computing devices of any kind) by a network 1526. The communication can be by, for example, an Ethernet connection, a digital subscriber line (DSL) connection, a telephone line connection, a coaxial cable system, a satellite system, a line-of-site wireless system, a cellular telephone system, an optical connection, etc.

The processor platform 1500 of the illustrated example also includes one or more mass storage devices 1528 to store software and/or data. Examples of such mass storage devices 1528 include magnetic storage devices, optical storage devices, floppy disk drives, HDDs, CDs, Blu-ray disk drives, redundant array of independent disks (RAID) systems, solid state storage devices such as flash memory devices and/or SSDs, and DVD drives.

The machine readable instructions 1532, which may be implemented by the machine readable instructions of FIGS. 7 and 8, may be stored in the mass storage device 1528, in the volatile memory 1514, in the non-volatile memory 1516, and/or on a removable non-transitory computer readable storage medium such as a CD or DVD.

Figure 16:
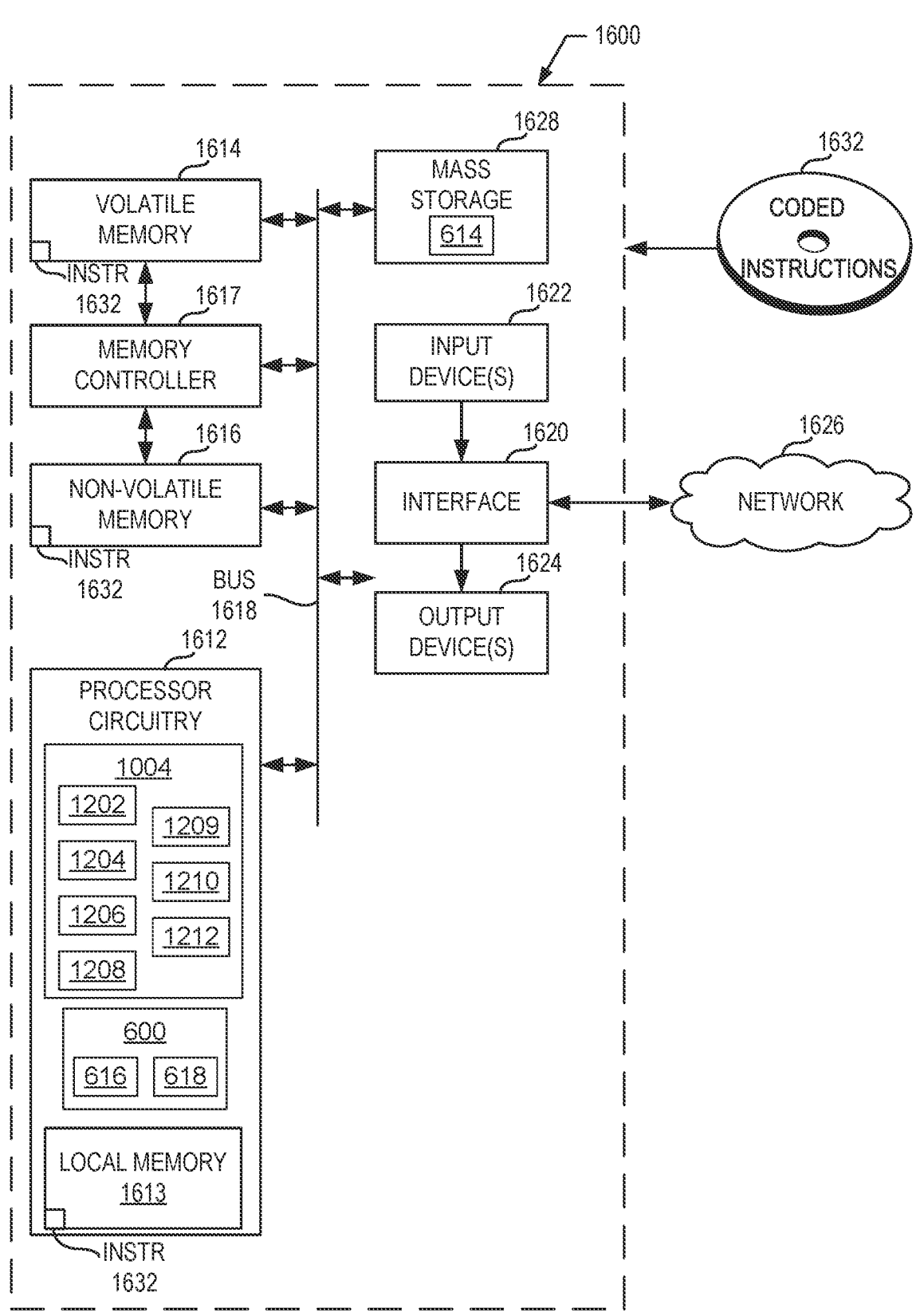
FIG. 16 is a block diagram of an example processing platform including processor circuitry structured to execute the example machine readable instructions and/or the example operations of FIGS. 13 and/or 14 to implement the leak management system and/or the model data set management circuitry of FIG. 12.

FIG. 16 is a block diagram of an example processor platform 1600 structured to execute and/or instantiate the machine readable instructions and/or the operations of FIGS. 13 and 14 to implement the leak management circuitry 1004 of FIGS. 10A, 10B, 10C, and 12. The processor platform 1600 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a headset (e.g., an augmented reality (AR) headset, a virtual reality (VR) headset, etc.) or other wearable device, or any other type of computing device.

The processor platform 1600 of the illustrated example includes processor circuitry 1612. The processor circuitry 1612 of the illustrated example is hardware. For example, the processor circuitry 1612 can be implemented by one or more integrated circuits, logic circuits, FPGAs, microprocessors, CPUs, GPUs, DSPs, and/or microcontrollers from any desired family or manufacturer. The processor circuitry

1612 may be implemented by one or more semiconductor-based (e.g., silicon based) devices. In this example, the processor circuitry 1612 implements the example sensor interface circuitry 1202, the leak region identifier circuitry 1204, the mobile sensor deployer circuitry 1206, the mobile sensor interface circuitry 1208, the leak identifier circuitry 1209, the leak mitigation circuitry 1210, the report generator circuitry 1212, the parameter selector circuitry 616, and the leak simulator circuitry 618.

The processor circuitry 1612 of the illustrated example includes a local memory 1613 (e.g., a cache, registers, etc.). The processor circuitry 1612 of the illustrated example is in communication with a main memory including a volatile memory 1614 and a non-volatile memory 1616 by a bus 1618. The volatile memory 1614 may be implemented by Synchronous Dynamic Random Access Memory (SDRAM), Dynamic Random Access Memory (DRAM), RAMBUS® Dynamic Random Access Memory (RDRAM®), and/or any other type of RAM device. The non-volatile memory 1616 may be implemented by flash memory and/or any other desired type of memory device. Access to the main memory 1614, 1616 of the illustrated example is controlled by a memory controller 1617.

The processor platform 1600 of the illustrated example also includes interface circuitry 1620. The interface circuitry 1620 may be implemented by hardware in accordance with any type of interface standard, such as an Ethernet interface, a universal serial bus (USB) interface, a Bluetooth® interface, a near field communication (NFC) interface, a Peripheral Component Interconnect (PCI) interface, and/or a Peripheral Component Interconnect Express (PCIe) interface.

In the illustrated example, one or more input devices 1622 are connected to the interface circuitry 1620. The input device(s) 1622 permit(s) a user to enter data and/or commands into the processor circuitry 1612. The input device(s) 1622 can be implemented by, for example, an audio sensor, a microphone, a camera (still or video), a keyboard, a button, a mouse, a touchscreen, a track-pad, a trackball, an isopoint device, and/or a voice recognition system.

One or more output devices 1624 are also connected to the interface circuitry 1620 of the illustrated example. The output device(s) 1624 can be implemented, for example, by display devices (e.g., a light emitting diode (LED), an organic light emitting diode (OLED), a liquid crystal display (LCD), a cathode ray tube (CRT) display, an in-place switching (IPS) display, a touchscreen, etc.), a tactile output device, a printer, and/or speaker. The interface circuitry 1620 of the illustrated example, thus, typically includes a graphics driver card, a graphics driver chip, and/or graphics processor circuitry such as a GPU.

The interface circuitry 1620 of the illustrated example also includes a communication device such as a transmitter, a receiver, a transceiver, a modem, a residential gateway, a wireless access point, and/or a network interface to facilitate exchange of data with external machines (e.g., computing devices of any kind) by a network 1626. The communication can be by, for example, an Ethernet connection, a digital subscriber line (DSL) connection, a telephone line connection, a coaxial cable system, a satellite system, a line-of-site wireless system, a cellular telephone system, an optical connection, etc.

The processor platform 1600 of the illustrated example also includes one or more mass storage devices 1628 to store software and/or data. Examples of such mass storage devices 1628 include magnetic storage devices, optical storage devices, floppy disk drives, HDDs, CDs, Blu-ray disk drives, redundant array of independent disks (RAID) systems, solid state storage devices such as flash memory devices and/or SSDs, and DVD drives.

The machine readable instructions 1632, which may be implemented by the machine readable instructions of FIGS. 13 and 14, may be stored in the mass storage device 1628, in the volatile memory 1614, in the non-volatile memory 1616, and/or on a removable non-transitory computer readable storage medium such as a CD or DVD.

Figure 17:
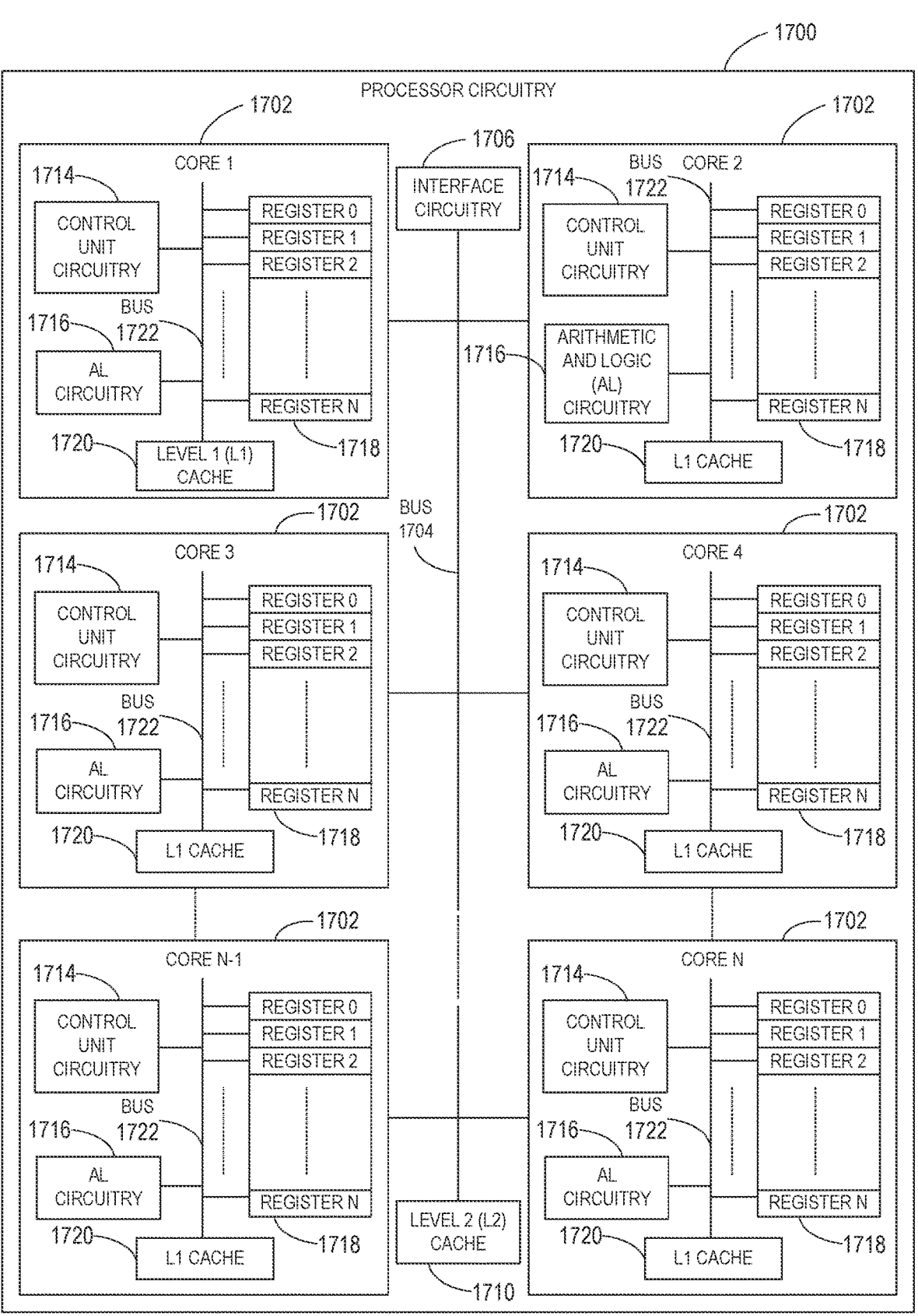
FIG. 17 is a block diagram of an example implementation of the processor circuitry of FIG. 15 and/or the processor circuitry of FIG. 16.

FIG. 17 is a block diagram of an example implementation of the processor circuitry 1512 of FIG. 15 and/or the processor circuitry 1612 of FIG. 16. In this example, the processor circuitry 1512 of FIG. 15 and/or the processor circuitry 1612 of FIG. 16 is/are implemented by a microprocessor 1700. For example, the microprocessor 1700 may be a general purpose microprocessor (e.g., general purpose microprocessor circuitry). The microprocessor 1700 executes some or all of the machine readable instructions of the flowcharts of FIGS. 7, 8, 13, and/or 14 to effectively instantiate the circuitry of FIGS. 6 and/or 12 as logic circuits to perform the operations corresponding to those machine readable instructions. In some such examples, the circuitry of FIGS. 6 and/or 12 is instantiated by the hardware circuits of the microprocessor 1700 in combination with the instructions. For example, the microprocessor 1700 may be implemented by multi-core hardware circuitry such as a CPU, a DSP, a GPU, an XPU, etc. Although it may include any number of example cores 1702 (e.g., 1 core), the microprocessor 1700 of this example is a multi-core semiconductor device including N cores. The cores 1702 of the microprocessor 1700 may operate independently or may cooperate to execute machine readable instructions. For example, machine code corresponding to a firmware program, an embedded software program, or a software program may be executed by one of the cores 1702 or may be executed by multiple ones of the cores 1702 at the same or different times. In some examples, the machine code corresponding to the firmware program, the embedded software program, or the software program is split into threads and executed in parallel by two or more of the cores 1702. The software program may correspond to a portion or all of the machine readable instructions and/or operations represented by the flowcharts of FIGS. 7, 8, 13, and/or 14.

The cores 1702 may communicate by an example first bus 1704. In some examples, the first bus 1704 may be implemented by a communication bus to effectuate communication associated with one(s) of the cores 1702. For example, the first bus 1704 may be implemented by at least one of an Inter-Integrated Circuit (I2C) bus, a Serial Peripheral Interface (SPI) bus, a PCI bus, or a PCIe bus. Additionally or alternatively, the first bus 1704 may be implemented by any other type of computing or electrical bus. The cores 1702 may obtain data, instructions, and/or signals from one or more external devices by example interface circuitry 1706. The cores 1702 may output data, instructions, and/or signals to the one or more external devices by the interface circuitry 1706. Although the cores 1702 of this example include example local memory 1720 (e.g., Level 1 (L1) cache that may be split into an L1 data cache and an L1 instruction cache), the microprocessor 1700 also includes example shared memory 1710 that may be shared by the cores (e.g., Level 2 (L2 cache)) for high-speed access to data and/or instructions. Data and/or instructions may be transferred (e.g., shared) by writing to and/or reading from the shared memory 1710. The local memory 1720 of each of the cores 1702 and the shared memory 1710 may be part of a hierarchy of storage devices including multiple levels of cache memory and the main memory (e.g., the main memory 1514, 1516 of FIG. 15, the main memory 1614, 1616 of FIG. 16). Typically, higher levels of memory in the hierarchy exhibit lower access time and have smaller storage capacity than lower levels of memory. Changes in the various levels of the cache hierarchy are managed (e.g., coordinated) by a cache coherency policy.

Each core 1702 may be referred to as a CPU, DSP, GPU, etc., or any other type of hardware circuitry. Each core 1702 includes control unit circuitry 1714, arithmetic and logic (AL) circuitry (sometimes referred to as an ALU) 1716, a plurality of registers 1718, the local memory 1720, and an example second bus 1722. Other structures may be present. For example, each core 1702 may include vector unit circuitry, single instruction multiple data (SIMD) unit circuitry, load/store unit (LSU) circuitry, branch/jump unit circuitry, floating-point unit (FPU) circuitry, etc. The control unit circuitry 1714 includes semiconductor-based circuits structured to control (e.g., coordinate) data movement within the corresponding core 1702. The AL circuitry 1716 includes semiconductor-based circuits structured to perform one or more mathematic and/or logic operations on the data within the corresponding core 1702. The AL circuitry 1716 of some examples performs integer based operations. In other examples, the AL circuitry 1716 also performs floating point operations. In yet other examples, the AL circuitry 1716 may include first AL circuitry that performs integer based operations and second AL circuitry that performs floating point operations. In some examples, the AL circuitry 1716 may be referred to as an Arithmetic Logic Unit (ALU). The registers 1718 are semiconductor-based structures to store data and/or instructions such as results of one or more of the operations performed by the AL circuitry 1716 of the corresponding core 1702. For example, the registers 1718 may include vector register(s), SIMD register(s), general purpose register(s), flag register(s), segment register(s), machine specific register(s), instruction pointer register(s), control register(s), debug register(s), memory management register(s), machine check register(s), etc. The registers 1718 may be arranged in a bank as shown in FIG. 17. Alternatively, the registers 1718 may be organized in any other arrangement, format, or structure including distributed throughout the core 1702 to shorten access time. The second bus 1722 may be implemented by at least one of an I2C bus, a SPI bus, a PCI bus, or a PCIe bus.

Each core 1702 and/or, more generally, the microprocessor 1700 may include additional and/or alternate structures to those shown and described above. For example, one or more clock circuits, one or more power supplies, one or more power gates, one or more cache home agents (CHAs), one or more converged/common mesh stops (CMSs), one or more shifters (e.g., barrel shifter(s)) and/or other circuitry may be present. The microprocessor 1700 is a semiconductor device fabricated to include many transistors interconnected to implement the structures described above in one or more integrated circuits (ICs) contained in one or more packages. The processor circuitry may include and/or cooperate with one or more accelerators. In some examples, accelerators are implemented by logic circuitry to perform certain tasks more quickly and/or efficiently than can be done by a general purpose processor. Examples of accelerators include ASICs and FPGAs such as those discussed herein. A GPU or other programmable device can also be an accelerator. Accelerators may be on-board the processor circuitry, in the same chip package as the processor circuitry and/or in one or more separate packages from the processor circuitry.

Figure 18:
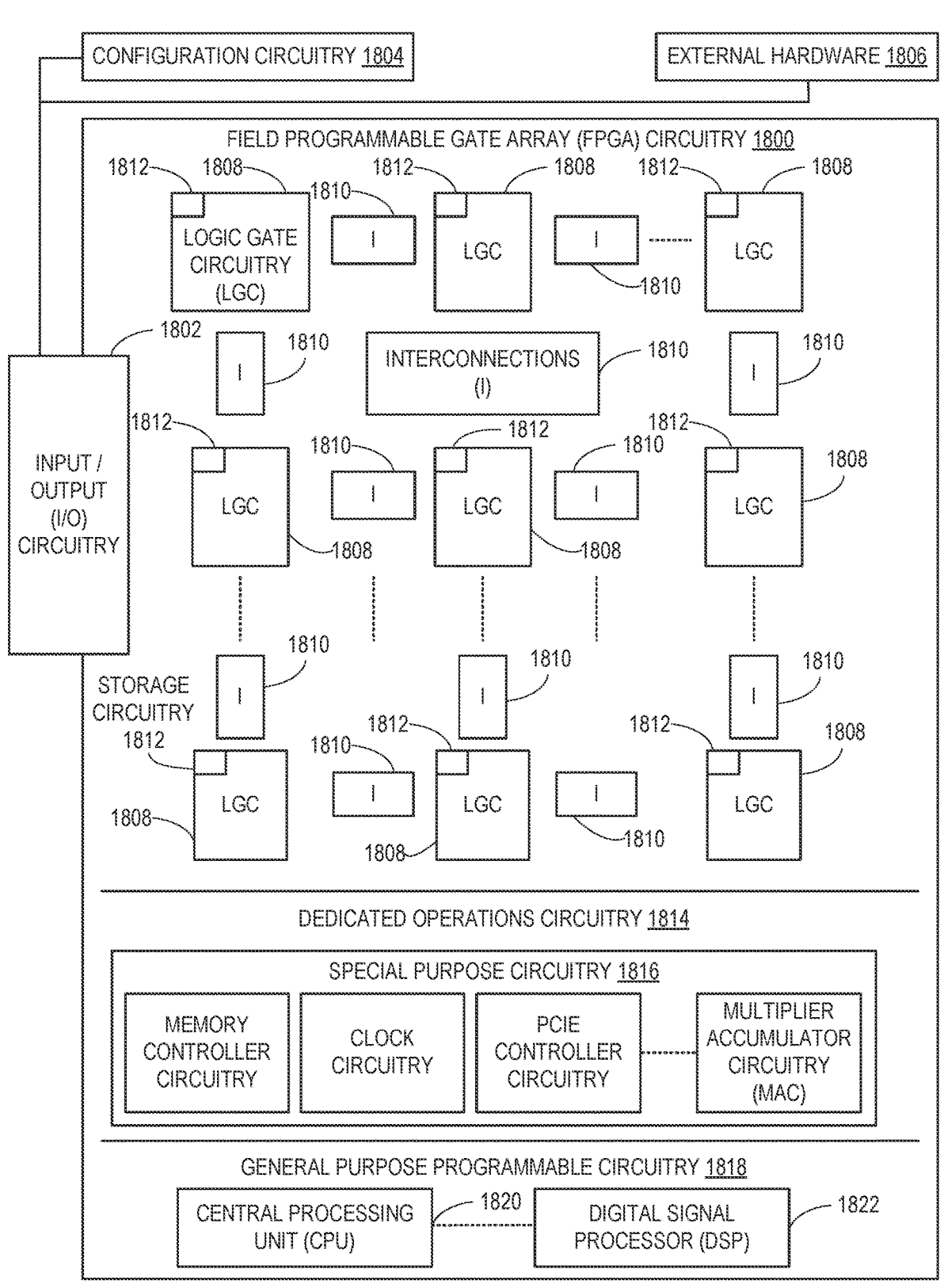
FIG. 18 is a block diagram of another example implementation of the processor circuitry of FIG. 15 and/or the processor circuitry of FIG. 16.

FIG. 18 is a block diagram of another example implementation of the processor circuitry 1512 of FIG. 15 and/or the processor circuitry 1612 of FIG. 16. In this example, the processor circuitry 1512 is implemented by FPGA circuitry 1800. For example, the FPGA circuitry 1800 may be implemented by an FPGA. The FPGA circuitry 1800 can be used, for example, to perform operations that could otherwise be performed by the example microprocessor 1700 of FIG. 17 executing corresponding machine readable instructions. However, once configured, the FPGA circuitry 1800 instantiates the machine readable instructions in hardware and, thus, can often execute the operations faster than they could be performed by a general purpose microprocessor executing the corresponding software.

More specifically, in contrast to the microprocessor 1700 of FIG. 17 described above (which is a general purpose device that may be programmed to execute some or all of the machine readable instructions represented by the flowcharts of FIGS. 7, 8, 13 and 14 but whose interconnections and logic circuitry are fixed once fabricated), the FPGA circuitry 1800 of the example of FIG. 18 includes interconnections and logic circuitry that may be configured and/or interconnected in different ways after fabrication to instantiate, for example, some or all of the machine readable instructions represented by the flowcharts of FIGS. 7, 8, 13 and 14. In particular, the FPGA circuitry 1800 may be thought of as an array of logic gates, interconnections, and switches. The switches can be programmed to change how the logic gates are interconnected by the interconnections, effectively forming one or more dedicated logic circuits (unless and until the FPGA circuitry 1800 is reprogrammed). The configured logic circuits enable the logic gates to cooperate in different ways to perform different operations on data received by input circuitry. Those operations may correspond to some or all of the software represented by the flowcharts of FIGS. 7, 8, 13 and 14. As such, the FPGA circuitry 1800 may be structured to effectively instantiate some or all of the machine readable instructions of the flowcharts of FIGS. 7, 8, 13 and 14 as dedicated logic circuits to perform the operations corresponding to those software instructions in a dedicated manner analogous to an ASIC. Therefore, the FPGA circuitry 1800 may perform the operations corresponding to the some or all of the machine readable instructions of FIGS. 7, 8, 13 and 14 faster than the general purpose microprocessor can execute the same.

In the example of FIG. 18, the FPGA circuitry 1800 is structured to be programmed (and/or reprogrammed one or more times) by an end user by a hardware description language (HDL) such as Verilog. The FPGA circuitry 1800 of FIG. 18, includes example input/output (I/O) circuitry 1802 to obtain and/or output data to/from example configuration circuitry 1804 and/or external hardware 1806. For example, the configuration circuitry 1804 may be implemented by interface circuitry that may obtain machine readable instructions to configure the FPGA circuitry 1800, or portion(s) thereof. In some such examples, the configuration circuitry 1804 may obtain the machine readable instructions from a user, a machine (e.g., hardware circuitry (e.g., programmed or dedicated circuitry) that may implement an Artificial Intelligence/Machine Learning (AI/ML) model to generate the instructions), etc. In some examples, the external hardware 1806 may be implemented by external hardware circuitry. For example, the external hardware 1806 may be implemented by the microprocessor 1700 of FIG. 17. The FPGA circuitry 1800 also includes an array of example logic gate circuitry 1808, a plurality of example configurable interconnections 1810, and example storage circuitry 1812. The logic gate circuitry 1808 and the configurable interconnections 1810 are configurable to instantiate one or more operations that may correspond to at least some of the machine readable instructions of FIGS. 7, 8, 13 and 14 and/or other desired operations. The logic gate circuitry 1808 shown in FIG. 18 is fabricated in groups or blocks. Each block includes semiconductor-based electrical structures that may be configured into logic circuits. In some examples, the electrical structures include logic gates (e.g., And gates, Or gates, Nor gates, etc.) that provide basic building blocks for logic circuits. Electrically controllable switches (e.g., transistors) are present within each of the logic gate circuitry 1808 to enable configuration of the electrical structures and/or the logic gates to form circuits to perform desired operations. The logic gate circuitry 1808 may include other electrical structures such as look-up tables (LUTs), registers (e.g., flip-flops or latches), multiplexers, etc.

The configurable interconnections 1810 of the illustrated example are conductive pathways, traces, vias, or the like that may include electrically controllable switches (e.g., transistors) whose state can be changed by programming (e.g., using an HDL instruction language) to activate or deactivate one or more connections between one or more of the logic gate circuitry 1808 to program desired logic circuits.

The storage circuitry 1812 of the illustrated example is structured to store result(s) of the one or more of the operations performed by corresponding logic gates. The storage circuitry 1812 may be implemented by registers or the like. In the illustrated example, the storage circuitry 1812 is distributed amongst the logic gate circuitry 1808 to facilitate access and increase execution speed.

The example FPGA circuitry 1800 of FIG. 18 also includes example Dedicated Operations Circuitry 1814. In this example, the Dedicated Operations Circuitry 1814 includes special purpose circuitry 1816 that may be invoked to implement commonly used functions to avoid the need to program those functions in the field. Examples of such special purpose circuitry 1816 include memory (e.g., DRAM) controller circuitry, PCIe controller circuitry, clock circuitry, transceiver circuitry, memory, and multiplier-accumulator circuitry. Other types of special purpose circuitry may be present. In some examples, the FPGA circuitry 1800 may also include example general purpose programmable circuitry 1818 such as an example CPU 1820 and/or an example DSP 1822. Other general purpose programmable circuitry 1818 may additionally or alternatively be present such as a GPU, an XPU, etc., that can be programmed to perform other operations.

Although FIGS. 17 and 18 illustrate two example implementations of the processor circuitry 1512 of FIG. 15 and/or the processor circuitry 1612 of FIG. 16, many other approaches are contemplated. For example, as mentioned above, modern FPGA circuitry may include an on-board CPU, such as one or more of the example CPU 1820 of FIG. 18. Therefore, the processor circuitry 1512 of FIG. 15 and/or the processor circuitry 1612 of FIG. 16 may additionally be implemented by combining the example microprocessor 1700 of FIG. 17 and the example FPGA circuitry 1800 of FIG. 18. In some such hybrid examples, a first portion of the machine readable instructions represented by the flowcharts of FIGS. 7, 8, 13 and 14 may be executed by one or more of the cores 1702 of FIG. 17, a second portion of the machine readable instructions represented by the flowcharts of FIGS. 7, 8, 13 and 14 may be executed by the FPGA circuitry 1800 of FIG. 18, and/or a third portion of the machine readable instructions represented by the FIGS. 7, 8, 13 and 14 may be executed by an ASIC. It should be understood that some or all of the circuitry of FIG. 6 or 12 may, thus, be instantiated at the same or different times. Some or all of the circuitry may be instantiated, for example, in one or more threads executing concurrently and/or in series. Moreover, in some examples, some or all of the circuitry of FIG. 6 or 12 may be implemented within one or more virtual machines and/or containers executing on the microprocessor.

In some examples, the processor circuitry 1512 of FIG. 15 may be in one or more packages. For example, the micro-processor 1700 of FIG. 17 and/or the FPGA circuitry 1800 of FIG. 18 may be in one or more packages. In some examples, an XPU may be implemented by the processor circuitry 1512 of FIG. 15 and/or the processor circuitry 1612 of FIG. 16, which may be in one or more packages. For example, the XPU may include a CPU in one package, a DSP in another package, a GPU in yet another package, and an FPGA in still yet another package.

From the foregoing, it will be appreciated that example systems, methods, apparatus, and articles of manufacture have been disclosed that identify leaks in hydrogen storage systems. Examples disclosed herein can identify if a leak is present in the fuel distribution system using hydrogen concentration data and identify if a leak has occurred by comparing the collected data to model hydrogen leaks. The example systems disclosed herein can identify the location in the system including the leak and isolate the section to prevent additional hydrogen leaking. Examples disclosed herein enable the location of a leak to be identified without manual inspection.

Further aspects of the present disclosure are provided by the subject matter of the following clauses:

Further examples and combinations thereof include the following:

Example 1 includes an apparatus comprising memory, and one or more processors to execute instructions to detect, via hydrogen concentration data, an elevated hydrogen concentration at a hydrogen storage system, determine a mass flow rate of a leak associated with the elevated hydrogen concentration based on the hydrogen concentration data and a location of a sensor associated with the hydrogen concentration data, and mitigate the leak by sending a signal to one or more controllable features of the hydrogen storage system based on the determined mass flow rate.

Example 2 includes the apparatus of any preceding clause, one or more processors further execute instructions to determine the mass flow rate by executing instructions to identify a first model data set of a plurality of model data sets based on a similarity of the first model data set with the hydrogen concentration data, and determine the mass flow rate based on the first model data set.

Example 3 includes the apparatus of any preceding clause, wherein the plurality of model data sets is a first plurality of model data sets, the hydrogen concentration data is collected via a grid of hydrogen concentration sensors, and the one or more processors further execute instructions to access ambient environment data from the hydrogen storage system, and filter a second plurality of model data sets based on the ambient environment data to generate the first plurality of model data sets.

Example 4 includes the apparatus of any preceding clause, wherein the one or more processors further execute instructions to identify a location of the leak based on the first model data set.

Example 5 includes the apparatus of any preceding clause, wherein the hydrogen concentration data is first hydrogen concentration data, and the one or more processors further executes instructions to identify a region of the hydrogen storage system including the leak, deploy a mobile sensor to the region to collect second hydrogen concentration data, and determine a leak source within the region based the second hydrogen concentration data.

Example 6 includes the apparatus of any preceding clause, wherein the mobile sensor is a flying drone.

Example 7 includes the apparatus of any preceding clause, wherein the one or more processors further executes instructions to determine a boundary surface of the hydrogen storage system, and determine the mass flow rate by integrating the hydrogen concentration data over the boundary surface.

Example 8 includes a method comprising detecting, via hydrogen concentration data, an elevated hydrogen concentration at a hydrogen storage system, determining a mass flow rate of a leak associated with the elevated hydrogen concentration based on the hydrogen concentration data and a location of a sensor associated with the hydrogen concentration data, and mitigating the leak by sending a signal to one or more controllable features of the hydrogen storage system based on the determined mass flow rate.

Example 9 includes the method of any preceding clause, wherein the determining the mass flow rate includes identifying a first model data set of a plurality of model data sets based on a similarity of the first model data set with the hydrogen concentration data, and determining the mass flow rate based on the first model data set.

Example 10 includes the method of any preceding clause, wherein the plurality of model data sets is a first plurality of model data sets, the hydrogen concentration data is collected via a grid of hydrogen concentration sensors, and further including accessing ambient environment data from the hydrogen storage system, and filtering a second plurality of model data sets based on the ambient environment data to generate the first plurality of model data sets.

Example 11 includes the method of any preceding clause, further including identifying a location of the leak based on the first model data set.

Example 12 includes the method of any preceding clause, wherein the hydrogen concentration data is first hydrogen concentration data, and further including identifying a region of the hydrogen storage system including the leak, deploying a mobile sensor to the region to collect second hydrogen concentration data, and determining a leak source within the region based the second hydrogen concentration data.

Example 13 includes the method of any preceding clause, further including determining a boundary surface of the hydrogen storage system, and determining the mass flow rate by integrating the hydrogen concentration data over the boundary surface.

Example 14 includes a non-transitory computer readable medium comprising instructions, which, when executed, cause one or more processors to detect, via hydrogen concentration data, an elevated hydrogen concentration at a hydrogen storage system, determine a mass flow rate of a leak associated with the elevated hydrogen concentration based on the hydrogen concentration data and a location of a sensor associated with the hydrogen concentration data, and mitigate the leak by sending a signal to one or more controllable features of the hydrogen storage system based on the determined mass flow rate.

Example 15 includes the non-transitory computer readable medium of any preceding clause, wherein the instructions when executed further cause the one or more processors to identify a first model data set of a plurality of model data sets based on a similarity of the first model data set with the hydrogen concentration data, and determine the mass flow rate based on the first model data set.

Example 16 includes the non-transitory computer readable medium of any preceding clause, wherein the plurality of model data sets is a first plurality of model data sets, the hydrogen concentration data is collected via a grid of hydrogen concentration sensors, and the instructions, when executed, further cause the one or more processors to access ambient environment data from the hydrogen storage system, and filter a second plurality of model data sets based on the ambient environment data to generate the first plurality of model data sets.

Example 17 includes the non-transitory computer readable medium of any preceding clause, wherein the instructions, when executed, further cause the one or more processors to identify a location of the leak based on the first model data set.

Example 18 includes the non-transitory computer readable medium of any preceding clause, wherein the hydrogen concentration data is first hydrogen concentration data, and the instructions, when executed, further cause the one or more processors to identify a region of the hydrogen storage system including the leak, deploy a mobile sensor to the region to collect second hydrogen concentration data, and determine a leak source within the region based the second hydrogen concentration data.

Example 19 includes the non-transitory computer readable medium of any preceding clause, wherein the mobile sensor is a flying drone.

Example 20 includes the non-transitory computer readable medium of any preceding clause, wherein the instructions, when executed, further cause the one or more processors to determine a boundary surface of the hydrogen storage system, and determine the mass flow rate by integrating the hydrogen concentration data over the boundary surface.

The following claims are hereby incorporated into this Detailed Description by this reference. Although certain example systems, methods, apparatus, and articles of manufacture have been disclosed herein, the scope of coverage of this application is not limited thereto. On the contrary, this application covers all systems, methods, apparatus, and articles of manufacture fairly falling within the scope of the claims of this application.

What is claimed is:

1. An apparatus comprising:
memory; and
one or more processors to execute instructions to:
    detect, via hydrogen concentration data, an elevated hydrogen concentration at a hydrogen storage system;
    determine a mass flow rate of a leak associated with the elevated hydrogen concentration based on the hydrogen concentration data and a location of a sensor associated with the hydrogen concentration data, the one or more processors further execute instructions to determine the mass flow rate by executing instructions to:
        identify a first model data set of a plurality of model data sets based on a similarity of the first model data set with the hydrogen concentration data, each of the plurality of model data sets associated with a corresponding simulated leak in the hydrogen storage system; and
        determine the mass flow rate based on a simulated mass flow rate of the first model data set; and
    mitigate the leak by sending a signal to one or more controllable features of the hydrogen storage system based on the determined mass flow rate.

2. The apparatus of claim 1, wherein the plurality of model data sets is a first plurality of model data sets, the hydrogen concentration data is collected via a grid of hydrogen concentration sensors, and the one or more processors further execute instructions to:
    access ambient environment data from the hydrogen storage system; and
    filter a second plurality of model data sets based on the ambient environment data to generate the first plurality of model data sets.

3. The apparatus of claim 1, wherein the one or more processors further execute instructions to identify a leak location of the leak based on the first model data set.

4. The apparatus of claim 1, wherein the hydrogen concentration data is first hydrogen concentration data, and the one or more processors further executes instructions to:
    identify a region of the hydrogen storage system including the leak;
    deploy a mobile sensor to the region to collect second hydrogen concentration data; and
    determine a leak source within the region based the second hydrogen concentration data.

5. The apparatus of claim 4, wherein the mobile sensor is a flying drone.

6. The apparatus of claim 1, wherein the one or more processors further executes instructions to:
    determine a boundary surface of the hydrogen storage system; and
    determine the mass flow rate by integrating the hydrogen concentration data over the boundary surface.

7. A method comprising:
    detecting, via hydrogen concentration data, an elevated hydrogen concentration at a hydrogen storage system;
    determining a mass flow rate of a leak associated with the elevated hydrogen concentration based on the hydrogen concentration data and a location of a sensor associated with the hydrogen concentration data, the determining the mass flow rate including:
        identifying a first model data set of a plurality of model data sets based on a similarity of the first model data set with the hydrogen concentration data, each of the plurality of model data sets associated with a corresponding simulated leak in the hydrogen storage system; and
        determining the mass flow rate based on a simulated mass flow rate of the first model data set; and
    mitigating the leak by sending a signal to one or more controllable features of the hydrogen storage system based on the determined mass flow rate.

8. The method of claim 7, wherein the plurality of model data sets is a first plurality of model data sets, the hydrogen concentration data is collected via a grid of hydrogen concentration sensors, and further including:
    accessing ambient environment data from the hydrogen storage system; and
    filtering a second plurality of model data sets based on the ambient environment data to generate the first plurality of model data sets.

9. The method of claim 7, further including identifying a leak location of the leak based on the first model data set.

10. The method of claim 7, wherein the hydrogen concentration data is first hydrogen concentration data, and further including:

identifying a region of the hydrogen storage system including the leak;

deploying a mobile sensor to the region to collect second hydrogen concentration data; and determining a leak source within the region based the second hydrogen concentration data.

11. The method of claim 7, further including:

determining a boundary surface of the hydrogen storage system; and determining the mass flow rate by integrating the hydrogen concentration data over the boundary surface.

12. A non-transitory computer readable medium comprising instructions, which, when executed, cause one or more processors to:

detect, via hydrogen concentration data, an elevated hydrogen concentration at a hydrogen storage system;

determine a mass flow rate of a leak associated with the elevated hydrogen concentration based on the hydrogen concentration data and a location of a sensor associated with the hydrogen concentration data, the determination of the mass flow rate to include:

identify a first model data set of a plurality of model data sets based on a similarity of the first model data set with the hydrogen concentration data, each of the plurality of model data sets associated with a corresponding simulated leak in the hydrogen storage system; and determine the mass flow rate based on a simulated mass flow rate of the first model data set; and mitigate the leak by sending a signal to one or more controllable features of the hydrogen storage system based on the determined mass flow rate.

13. The non-transitory computer readable medium of claim 12, wherein the plurality of model data sets is a first plurality of model data sets, the hydrogen concentration data is collected via a grid of hydrogen concentration sensors, and the instructions, when executed, further cause the one or more processors to:

access ambient environment data from the hydrogen storage system; and filter a second plurality of model data sets based on the ambient environment data to generate the first plurality of model data sets.

14. The non-transitory computer readable medium of claim 12, wherein the instructions, when executed, further cause the one or more processors to identify a leak location of the leak based on the first model data set.

15. The non-transitory computer readable medium of claim 12, wherein the hydrogen concentration data is first hydrogen concentration data, and the instructions, when executed, further cause the one or more processors to:

identify a region of the hydrogen storage system including the leak;

deploy a mobile sensor to the region to collect second hydrogen concentration data; and determine a leak source within the region based the second hydrogen concentration data.

16. The non-transitory computer readable medium of claim 15, wherein the mobile sensor is a flying drone.

17. The non-transitory computer readable medium of claim 12, wherein the instructions, when executed, further cause the one or more processors to:

determine a boundary surface of the hydrogen storage system; and determine the mass flow rate by integrating the hydrogen concentration data over the boundary surface.

\* \* \* \* \*